(12) United States Patent
Guan

(10) Patent No.: US 9,238,697 B2
(45) Date of Patent: Jan. 19, 2016

(54) POLYMERIC MATERIALS AND METHODS

(75) Inventor: Zhibin Guan, Irvine, CA (US)

(73) Assignee: The Regents of the University of California, Oakland, CA (US)

(*) Notice: Subject to any disclaimer, the term of this patent is extended or adjusted under 35 U.S.C. 154(b) by 1677 days.

(21) Appl. No.: 11/817,051

(22) PCT Filed: Feb. 24, 2006

(86) PCT No.: PCT/US2006/006743
§ 371 (c)(1),
(2), (4) Date: Jul. 30, 2008

(87) PCT Pub. No.: WO2006/091894
PCT Pub. Date: Aug. 31, 2006

(65) Prior Publication Data
US 2008/0317861 A1    Dec. 25, 2008

Related U.S. Application Data

(60) Provisional application No. 60/656,743, filed on Feb. 25, 2005.

(51) Int. Cl.
*A61K 38/00* (2006.01)
*C07K 7/04* (2006.01)
*C08B 37/00* (2006.01)
*C12N 11/10* (2006.01)

(52) U.S. Cl.
CPC .............. *C08B 37/006* (2013.01); *C12N 11/10* (2013.01)

(58) Field of Classification Search
None
See application file for complete search history.

(56) References Cited

U.S. PATENT DOCUMENTS

| 6,696,089 | B2 | 2/2004 | Kabanov et al. |
| 6,740,310 | B2 | 5/2004 | Edwards et al. |
| 2004/0142856 | A1* | 7/2004 | DeFrees et al. ............... 514/8 |
| 2005/0084537 | A1 | 4/2005 | Martyn et al. |

OTHER PUBLICATIONS

Wibullucksanakul, 1997, Macromol. Chem. Phys., 198, 305-319.*
Edwards, 1987, Synthesis and Chemistry of Agrochemicals, ACS Symposium Series, vol. 355, Chapter 14, pp. 151-160.*
Misra, 1998, Biochemistry, 37, 1917-1925.*
Hashimoto, 1995, Journal of Polymer Science, 33, 1495-1503.*
Suhara, Tetrahedron Letters, vol. 38, No. 41, pp. 7167-7170, 1997.*
Gruner, Chem. Rev. 2002, 102, 491-514.*
Gruner, 2002, Chem . Rev., 102, 491-514.*
Kiely, Polymer Chemistry, vol. 38, 594-603 (2000).*
Bachmann, Journal of Polymer Science: Part A Polymer Chemistry, vol. 30, 2059-2062 (1992).*

* cited by examiner

*Primary Examiner* — Satyanarayana R Gudibande
(74) *Attorney, Agent, or Firm* — Mintz Levin Cohn Ferris Glovsky and Popeo, P.C.; Shovon Ashraf

(57) ABSTRACT

Chimeric polymer compositions and methods are provided in which a plurality of carbohydrate moieties and amino acids form the backbone of a polymer. Most preferably, the polymer includes alternating saccharide and peptide portions to form the chimeric polymer.

15 Claims, 4 Drawing Sheets

POLYMERIC MATERIALS AND METHODS

This application claims priority to our U.S. provisional patent application with the Ser. No. 60/656,743, which was filed Feb. 25, 2005.

FIELD OF THE INVENTION

The field of the invention is heteropolymers, and especially heteropolymers in which a peptide and a saccharide form the backbone.

BACKGROUND OF THE INVENTION

Numerous natural and synthetic heteropolymeric compounds are known in the art. For example, glycopeptides are commonly found in most eukaryotic cells and on cell membranes. In most cases, glycopeptides are enzymatically and post-translationally synthesized in a cell. Therefore, and from a structural perspective, the backbone of such molecules is a polypeptide with glycosyl side chains covalently attached to pendant R-groups of polypeptide backbone. Likewise, numerous natural polysaccharides are known to carry one or more amino acids. For example, murein (which is a polymer comprising N-acetylglucosamine and N-acetylmuramic acid) is typically derivatized with a pentapeptide that is covalently coupled to the N-acetyl muramic acid in the murein to act as crosslinker between two or more polysaccharide chains. Once again, from a structural perspective, the backbone of such molecules is a polysaccharide to which oligopeptides are covalently bound as pendant groups.

Remarkably, and despite the availability of numerous carbohydrate and amino acid building blocks, heteropolymers in which carbohydrates and peptides form the backbone of a heteropolymer have generally not been reported, with the exception of relatively few and selected molecules. For example, a mixed backbone heteropolymer consisting of DNA and PNA portions was reported in Biochem Pharmacol. 2005 Nov. 1; 70(9):1277-87. In this paper, a sugar-phosphate backbone of two DNA portions was linked to a peptide backbone of a PNA portion. Similarly, certain chimeric molecules in which a PNA (peptide nucleic acid) and lactose form a backbone were described by Zhang et al. in Bioorg Med Chem Lett. 2001 May 21; 11(10):1269-72. While such polymers have desirable properties with respect to nucleic acid hybridization, various drawbacks may remain. Among other things, where the backbone includes a DNA portion, negative charges are typically present at physiological pH due to the phosphate groups in the backbone.

Other functionalized polyester graft copolymers consisting of a linear α-hydroxy-acid polyester backbone having at least one amino acid group incorporated therein and at least one poly(amino acid) side chain extending from an amino acid group in the polyester have been described in U.S. Pat. No. 6,740,310. In still further examples, a polymer of hyaluronic acid and a second polymer of either a non-ionic polymer, a polymeric gum, or a combination thereof are combined to form certain heteropolymers as previously described in U.S. Pat App. No. 2005/0084537. While such polymers may provide certain advantages, controlled and high yield synthesis is often difficult. Moreover, many of such synthetic polymers may elicit an immune response in an animal when implanted.

Therefore, while numerous compositions and methods for heteropolymers are known in the art, all or almost all of them suffer from one or more disadvantages. Most significantly, heteropolymers with mixed backbones in which amino acids and sugars form the backbone in compounds other than PNA-containing compounds are not known. Thus, there is still a need to provide improved heteropolymers, and especially those with an amino acid-carbohydrate mixed backbone.

SUMMARY OF THE INVENTION

The present invention is directed to heteropolymeric compositions and methods in which at least one carbohydrate moiety and at least one amino acid moiety form the backbone of the heteropolymer.

In one aspect of the inventive subject matter, a chimeric polymer has a structure according to the formula: $[(M)_{x1}(N)_{y1}]_{z1}[(M)_{x2}(N)_{y2}]_{z2}$, wherein M is independently a carbohydrate moiety, and N is independently an amino acid, wherein x1, x2, y1, y2, z1, and z2 are independently an integer between 1 and 10000, inclusive, wherein x1 is optionally null when y2 is greater or equal to 1, and wherein y2 is optionally null when x1 is greater or equal to 1, and wherein the carbohydrate moiety and the amino acid are coupled to each other such that the carbohydrate moiety and the amino acid unit form a backbone of the polymer.

Most preferably, at least one of x1 and x2 is an integer between 2 and 20, and/or at least one of y1 and y2 is an integer between 2 and 20. Typically, the amino acid is part of the backbone via a covalent bond between the alpha amino group and the alpha carboxyl group, and/or the carbohydrate is covalently coupled to the amino acid via an amide bond. In still further contemplated aspects, at least one of the carbohydrate moieties comprises a cyclic saccharide, and/or comprises at least one non-naturally occurring saccharide. Where desirable, at least one of M and N in contemplated polymers may comprise a crosslinking functionality, wherein the crosslinking functionality is preferably covalently bound to another crosslinking functionality of another chimeric polymer to thereby form a crosslinked polymer. In still further preferred aspects, the crosslinked polymer is a hydrogel that optionally includes at least one of a pharmaceutical agent and a cell, and the polymer is formulated in a formulation suitable for at least one of implantation, injection, and oral administration.

Thus, in another aspect of the inventive subject matter, pharmaceutical compositions are contemplated that comprise the chimeric polymer of claim 1 and a pharmaceutically active agent. Where desirable, the pharmaceutically active agent is encapsulated in the biodegradable polymer or attached covalently to the polymer. Alternatively, or additionally, the pharmaceutically active agent is a polypeptide, and at least one of (N)y1 and (N)y2 comprises the pharmaceutically active agent. In at least some cases, it is preferred that the polymer has a composition that is suitable for degradation to thereby release the pharmacologically active agent. In alternative aspects, contemplated polymers may also have a structure that allows for bioerosion and/or controlled release.

In yet another aspect of the inventive subject matter, a cell-containing structure may include, or may be built from contemplated chimeric polymers. Preferably, the chimeric polymer in such structures is crosslinked with at least one other chimeric polymer, and most preferably forms a hydrogel with other chimeric polymers. Among other configurations, such structures are especially suitable for in vitro cell growth, and even for in vivo cell growth (e.g., in the form of a cell-containing implant). For example, such polymers may be employed to grow and/or expand stem cells, which may or may not be inducted to differentiation in or on that polymer.

Additionally, or alternatively, contemplated polymers may be employed as coating for implanted devices (which may or may not include cells).

Various objects, features, aspects and advantages of the present invention will become more apparent from the following detailed description of preferred embodiments of the invention.

DETAILED DESCRIPTION

Figure 1:
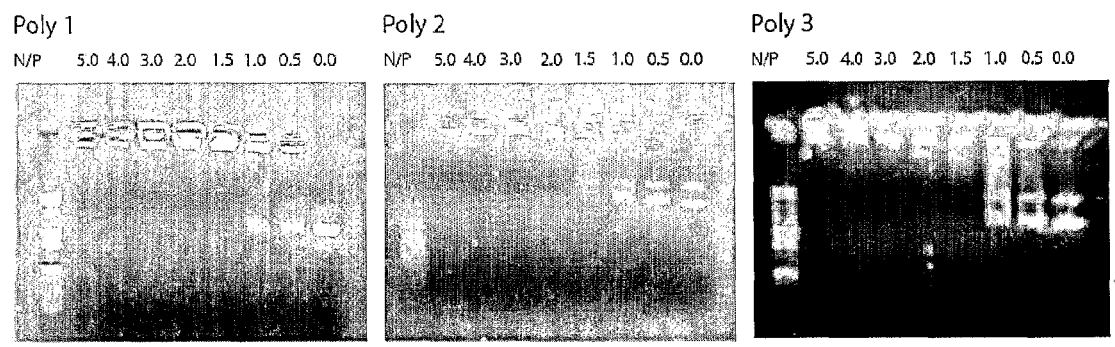
FIG. 1 is a photograph of various agarose gel electrophoreses using DNA polyplexes with control and contemplated compounds.

The inventor generally contemplates compositions and methods for heteropolymers in which at least one carbohydrate moiety and at least one amino acid moiety form the backbone of the heteropolymer. Most preferably, contemplated heteropolymers will include one or more mono-, oligo-, or polysaccharide or substituted polyol (wide supra) portions that are covalently coupled to one or more oligo-, or polypeptide portions. Most typically, it is preferred that contemplated heteropolymers will include multiple and alternating portions of oligo- and/or polysaccharides and oligo- and/or polypeptides as schematically illustrated in Structure I below. However, other permutations are also deemed suitable for use herein.

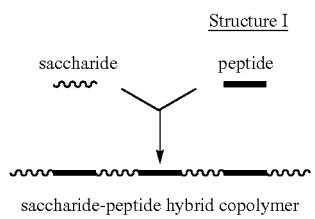

Structure I saccharide-peptide hybrid copolymer

Using such general approach, it should be appreciated that at least one of the amino acid/peptide portion and the saccharide portion may be branched, or provide reactive groups that can be used for branching (e.g., using further peptide and/or saccharide portions, or other groups) or other covalent or non-covalent interaction. Thus, it should be recognized that the heteropolymers according to the inventive subject matter may be prepared as linear, branched, hyperbranched, or dendrimeric molecules as exemplarily depicted in Structure II below.

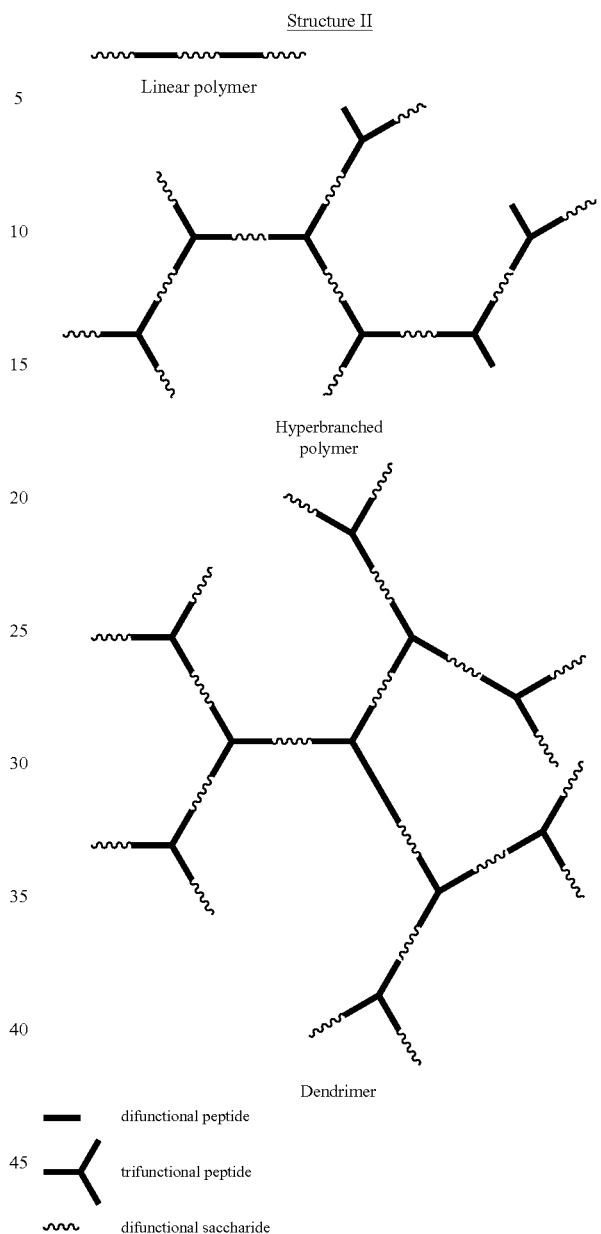

Structure II

Linear polymer

Hyperbranched polymer

Dendrimer

— difunctional peptide

⟨ trifunctional peptide

∿∿ difunctional saccharide

Among other contemplated options, it is generally preferred that the covalent coupling of a saccharide portion with an amino acid and/or peptide portion will be performed via an amide bond formation using synthetic procedures well known in the art, however, numerous other covalent bonds may also be appropriate, including ester bonds, ether bonds, secondary amine bonds, or imide bonds. For example, amide bonds may be formed by reacting activated sugar acid groups of the saccharide portion and an amino group of the amino acid or peptide portion (e.g., using acid chloride and amino group, or using DCCD or other reagents to activate carboxyl group), via ring opening polymerization reactions (e.g., using a sugar lactone and an amino group), via Click-type reaction (e.g., using sugar azide and acetylene-modified peptide), via condensation of N-alkylhydroxylamines and α-ketoacids (e.g., using sugar acid and hydroxylamine peptide), etc. Representative examples of such synthetic paths are provided below in the experimental section.

Alternatively, it is also contemplated that the compounds according to the inventive subject matter can be prepared via crosslinking of the respective termini using a third class of compounds. Such crosslinkers may then react, for example, using reactive groups and in a manner as described above to form the corresponding amide bonds. Regardless of the actual synthetic route taken, it should be recognized that synthesis will generally follow established routes and procedures, and can be easily modularized to arrive at a virtually unlimited number of combinations. Furthermore, these chimeric polymers may crosslink through disulfide bonds, ionic interactions between amino group cations (—$NH_3^+$) and carboxylate anions (—$COO^-$), hydrogen bonding between polar groups (hydroxy, amino, thio, amido, carboxyl etc.) and hydrophobic Van der Waal interactions.

Contemplated Carbohydrates

It is generally contemplated that suitable carbohydrates in the chimeric polymers presented herein include monosaccharides (i.e., single saccharide), oligosaccharides (i.e., between 2 and 20 saccharides that are covalently coupled to each other in linear or branched fashion), and polysaccharides (i.e., between 21 and 100000 saccharides (and even more) that are covalently coupled to each other in linear or branched fashion). Where the carbohydrate is an oligo- or polysaccharide, it should be recognized that the saccharides may be identical or chemically distinct. It is also understood that the terms carbohydrate, sugar and saccharide are used here interchangeably and have the same meaning. Furthermore, the term carbohydrate also include open chain polyols of the formula

$R_B$—[CHOH]n-$R_T$ with up to 12 carbon atoms having terminal groups $R_B$ and $R_T$ selected from CHO, $N_3$, $CH_2OH$, COOH, COCl, CO—O-alkyl (alkenyl) or the terminal carboxyl group may combine with the gamma hydroxy group to form a bis-lactone. The hydroxy groups, for example, of the polyol dicarboxylic acid may be derivatized as acetonide or with various other groups, including alkyl. Also included are molecules where one or more hydroxy groups are replaced by amino or acetylamino groups. Furthermore, it should be recognized that the open-chain carbohydrate may be in the aldose or ketose form.

Moreover, with respect to the origin of the carbohydrates it is contemplated that the carbohydrates may be naturally occurring or synthetic carbohydrates, which may be further processed or otherwise chemically modified to a predetermined structure and/or molecular weight. For example, naturally occurring carbohydrates include starch, glycogen, amylose, beta glucans, etc., which may be enzymatically, chemically, and/or mechanically processed to a particular size. Additionally, or alternatively, the carbohydrates may be chemically or enzymatically modified to include one or more desirable side groups and/or substituents. Synthetic carbohydrates useful for polymers of the present inventive subject matter may be prepared using enzymatic or synthetic procedures, and it is especially preferred that such synthetic carbohydrates will already include reactive groups and protective groups required for subsequent coupling with an amino acid and/or peptide. However, and regardless of the origin of the carbohydrate, it should be recognized that reactive groups and/or protecting groups may be introduced into the carbohydrate using methods and protocols well known in the art.

Further contemplated exemplary carbohydrates include those in which the heteroatom in the cyclic portion of the sugar is an atom other than oxygen (e.g., sulfur, carbon, or nitrogen) analogs, while other alternative sugars may not be cyclic but may be in a linear (open-chain) form. Contemplated sugars may be oxidized or reduced carbohydrates. Suitable sugars may also include one or more double bonds. Still further specifically contemplated alternative sugars include those with one or more non-hydroxyl substituents, and particularly contemplated substituents include mono-, di-, and triphosphates (preferably as $C_5'$ esters), alkyl groups, alkoxygroups, halogens, amino groups acyl- and alkylamino groups, sulfur-containing substituents, etc. It is still further contemplated that all contemplated substituents (hydroxyl substituents and non-hydroxyl substituents) in a carbohydrate having a cyclic structure may be directed in the alpha or beta configuration.

Numerous of the contemplated sugars and sugar analogs are commercially available. However, where contemplated sugars are not commercially available, it should be recognized that there are various methods known in the art to synthesize such sugars. For example, suitable protocols can be found in "Modem Methods in Carbohydrate Synthesis" by Shaheer H. Khan (Gordon & Breach Science Pub; ISBN: 3718659212), in U.S. Pat. Nos. 4,880,782 and 3,817,982, in WO88/00050, or in EP199,451. An exemplary collection of further contemplated sugars and sugar analogs is depicted below, wherein all of the exemplary sugars may be in D- or L-configuration, and wherein at least one of the substituents on anomeric carbon may further be in either alpha or beta orientation. The mono-. oligo. and polysaccharides are mostly represented as a five-membered ring (furanose sugars) or six-membered rings (pyranoses). An exemplary pyranose sugar is depicted below, wherein R is independently defined as above. Most preferably, at least one of R is OH, $NH_2$, NH-Acyl or H, and the heteroatom X is selected from the group consisting of O, S, Se, and N—R. With respect to the stereochemistry of suitable six-membered ring sugars, the same considerations as above for five-membered-ring sugars apply.

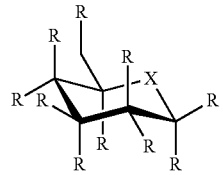

An especially contemplated class of sugars comprises oligomeric forms of the sugars above in which the number of sugar molecules forming part of the backbone is between 1 and 100, and more typically between 2 and 50. Where the sugar is in cyclic form, it should be recognized that the coupling may employ any available group on the sugar, including the anomeric carbon atom (e.g., to form 1,6 or 1,4 linked molecule). The coupling at the anomeric carbon may be α or β. However, other covalent couplings are also deemed suitable.

Similarly, contemplated linear sugars most preferably are coupled to the adjacent molecule (e.g., sugar and/or amino acid) via respective terminal functional groups. For example, where the sugar is in an aldose form, coupling with the adjacent molecules typically employs the terminal/primary hydroxyl groups. Oxidation of one or more of the hydroxy groups to the corresponding aldehyde, keto or carboxylic acid group is also contemplated, and coupling may therefore also include acetals, ketals, esters, thiol esters, imines, amines, and amides, etc.

Contemplated Peptides and Amino Acids

It is generally contemplated that the amino acids and peptides for use in the chimeric polymers presented herein may be independently present in numerous forms and structural permutations. For example, contemplated polymers include single amino acids (e.g., naturally occurring, proteinogenic, or otherwise), oligopeptides (i.e., between 2 and 20 amino acids that are covalently coupled to each other in linear or branched fashion), and polypeptides (i.e., between 20 and 100000 amino acids (and even more) that are covalently coupled to each other in linear or branched fashion). Of course, where the peptide is an oligopeptide or a polypeptide, it should be recognized that the amino acids may be identical or chemically distinct, and/or that the peptide may be linear or branched. With respect to the origin of the peptides and/or amino acids, it is contemplated that these compounds may be naturally occurring or synthetic, and that they may be further processed or otherwise chemically modified to a predetermined structure and/or molecular weight. For example, naturally occurring amino acids and peptides include all proteinogenic amino acids, various natural and synthetic α-amino acids in D- and L-configuration (and mixtures thereof), structural polypeptides (e.g., keratin, actin, myosin, collagen, etc.), catalytically active peptides (e.g., oxidoreductases, dehydrogenases, etc.), binding peptides (e.g., albumin, various globulins, etc.), and so on, and each of those may be enzymatically, chemically, and/or mechanically processed to a particular size.

Synthetic peptides useful for polymers of the present inventive subject matter may be prepared using enzymatic, recombinant and/or synthetic procedures (e.g., solid or solution phase), and it is especially preferred that such synthetic peptides will already include reactive groups and/or protective groups required for subsequent coupling with a carbohydrate. However, and regardless of the origin of the amino acid and/or peptide, it should be recognized that reactive groups and/or protecting groups may also be introduced into the compound using methods and protocols well known in the art. Additionally, or alternatively, it should be recognized that suitable peptides may be chemically and/or enzymatically modified to include one or more desirable functional groups or substituents, which may then perform a particular desirable function and/or provide a tailored physico-chemical property. For example, natural and/or synthetic peptides may be enzymatically digested to provide a desired molecular weight (distribution), or a particular chemical composition. In other examples, the peptide may also be glycosylated or otherwise modified, preferably using one or more of the pendant groups off the peptide backbone.

In one aspect of the inventive subject matter, suitable amino acids will preferably have the formula of $CR_1R_2(CO_2^-)(NH_3^+)$, wherein $R_1$ and $R_2$ are independently H, aryl, heteroaryl, aralkyl, alkyl, alkenyl, alkynyl, and cycloalkyl, optionally substituted with OH, SH, $SCH_3$, COOH, $NH_2$, $CONH_2$, imidazolyl, furyl, thienyl, or indolyl (each of the hydrocarbon group above may further include one or more heteroatoms [e.g., O, S, Se, N, P]), and wherein $R_1$ and $R_2$ may also form a ring (optionally with the $NH_2$ group to thereby form a proline or proline-like amino acid). Where $R_1$ and $R_2$ are not the same, it should be recognized that the amino acid will have one or more chiral centers, and all enantiomers, diastereomers, racemates and mixtures thereof are deemed appropriate. Therefore, among contemplated amino acids, all synthetic (non-natural) and naturally occurring amino acids, and particularly proteinogenic amino acids are contemplated for use herein. With respect to the carboxyl group, the amino group can be in alpha, beta, gamma, delta, and epsilon position. In less preferred aspects, the amino acid is modified to include a heterocyclic base. Thus, and at least in some instances, compounds are excluded from the scope of this inventive subject matter where the amino acid is modified to include adenine, guanine, cytosine, thymidine, and/or uracil (or other nucleobase that is capable of Watson-Crick hybridization).

In preferred aspects, contemplated amino acids are coupled to each other to form an oligopeptide or polypeptide, most preferably by formation of at least one amide bond between an amino group of one amino acid and a carboxylate group of a second amino acid. However, it should be appreciated that numerous alternative bonds may also be formed to covalently couple two amino acids, and the particular bond between two amino acids will at least in part depend on the chemical composition of the first and second amino acid. Most typically a backbone portion comprising amino acids will be formed by amide bonds between two or more alpha-amino acids. Alternatively, backbones may also include bonds formed between an alpha-amino acid and a beta- or gamma amino acid, a carboxyl of an alpha-amino acid coupled, for example, to epsilon amino group of lysine or non-amide bonds (e.g., ester bond, imide bond, thioester bond, ether bond, disulfide bond etc.).

The term "alkyl" as used herein refers to a saturated hydrocarbon group in a straight, branched, chiral or achiral or cyclic configuration (also referred to as cycloalkyl, see below), and particularly contemplated alkyl groups include lower alkyl groups (i.e., those having six or less carbon atoms). Exemplary alkyl groups are methyl, ethyl, propyl, 2-propyl, butyl, 2-butyl, 2-methylpropyl, 2,2-dimethylethyl, pentyl, 2-methylbutyl, hexyl, etc.

The term "alkenyl" as used herein refers to straight or branched, chiral or achiral unsaturated hydrocarbon group having at least one double bond. Thus, particularly contemplated alkenyl groups include straight or branched, groups having two to six carbon atoms (e.g., ethenyl, 1-propenyl, 2-propenyl 1-butenyl, 2-pentenyl, etc.).

Similarly, the term "alkynyl" as used herein refers to an unsaturated hydrocarbon group having at least one triple bond. Especially contemplated alkynyls include straight, branched, alkynes having two to six total carbon atoms (e.g., ethynyl, 1-propynyl (propargyl), 2-butynyl, 2-pentynyl, etc.).

The term "cycloalkyl" as used herein refers to a cyclic hydrocarbon group (i.e., in which a chain of carbon atoms of a hydrocarbon forms a ring), preferably including three to eight carbon atoms. Thus, exemplary cycloalkyls include cyclopropyl, cyclobutyl, cyclopentyl, cyclohexyl, cycloheptyl, and cyclooctyl. It should further be appreciated that a cycloalkyl group may also include a double bond (termed cycloalkenyl), for example, cyclohexenyl.

The term "aryl" as used herein refers to an aromatic hydrocarbon ring, which may further include one or more heteroatoms (then also referred to as heteroaryl). Thus, contemplated aryl groups include phenyl, naphthyl, etc. and contemplated heteroaryl groups include 2- and 3-pyridyl, 2- and 3-thienyl, 3-indolyl, 4-imidazolyl and the like.

The contemplated aralkyl groups include benzyl and phenethyl.

The term "alkoxy" as used herein refers to straight or branched chain alkoxides, wherein the hydrocarbon portion may have any number of carbon atoms (and may further include a double or triple bond). For example, suitable alkoxy groups include methoxy, ethoxy, 2-propoxy, etc.

Similarly, the term "alkylthio" refers to straight or branched alkyl group attached to a sulfur atom, wherein the hydrocarbon portion may have any number of carbon atoms (and may further include a double or triple bond). For example, contemplated alkylthio groups include methylthio (MeS), ethylthio, propylthio, etc.

The term "alkylamino" refers to straight or branched alkyl group attached to a NH group, wherein the hydrocarbon portion may have any number of carbon atoms (and may further include a double or triple bond or may be cyclic). Furthermore, the hydrogen of the NH of the alkylamino group may be substituted with another alkyl group resulting in a dialkylamino group, wherein the two alkyl groups may be same or different. One or both of the alkyl groups may be optionally substituted by a OH group. Therefore, exemplary alkylamino and dialkylamino groups include methylamino, dimethylamino, ethylamino, diethylamino, 2-propylamino, 2-hydroxyethylamino, etc.

The term "halogen" as used herein refers to fluorine, chlorine, bromine, and iodine.

It should also be recognized that all, or almost all of the above-defined groups may be substituted with one or more substituents, which may in turn be substituted as well. For example, where a hydrogen atom in an alkyl is substituted with an amino group, one or both hydrogen atoms in the amino group may be substituted with another group (e.g., alkyl or alkenyl).

The term "substituted" as used herein refers to a replacement of an atom or a functional group (e.g., H, $NH_2$, or OH) with another atom or functional group, and particularly contemplated functional groups include $-NH_2$, $-OH$, $-SH$, COOH, COOR, aryl, aralkyl, alkyl, alkenyl, alkynyl, $-NH_3^+$, halogens, NHCOR, $NHCONH_2$, $NHCSNH_2$, $O(CH_2)_{1-4}COOH$, $OCH_2CONH_2$, $OCH_2CONHR$, $OC(Me)_2COOH$, $OC(Me)_2CONH_2$, $NHCH_2COOH$, $NHCH_2CONH_2$, $NHSO_2R$, $NHSO_2CF_3$, $OCH_2$-heterocycles, $PO_3H$, $SO_3H$, $(CH_2)_{1-3}COOH$, $CH=CHCOOH$, $NHCOCH_2CH(OH)COOH$, $CH(PO_3H)_2$, NHCHO, with R being an alkyl.

Contemplated Backbones and Linkages

It is generally preferred that the backbone of the compounds contemplated herein will include at least one carbohydrate moiety and at least one amino acid moiety, and even more preferred that the two moieties are independently repeated. Therefore, a general structure or substructure of the backbone may be expressed by Formula I

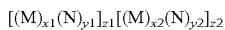   Formula I in which M is independently a carbohydrate moiety (e.g., monosaccharide, or analog), N is independently an amino acid, and x1, x2, y1, y2, and z1, z2, are independently integers between 1 and several 10000, wherein x1 is optionally null when y2 is greater or equal to 1, and wherein y2 is optionally null when x1 is greater or equal to 1. It should be noted that where x1 and/or x2 are greater than 1, the carbohydrate moieties are typically covalently coupled together (e.g., via condensation or glycosidic linkage). Similarly, where y1 and/or y2 are greater than 1, the amino acids are typically covalently coupled together (e.g., via amide bond). As used herein, the term "backbone" refers to a contiguous chain of covalently bound atoms (e.g., carbon, oxygen, or nitrogen atom) or moieties (e.g., amino acid or monosaccharide), in which removal of any of the atoms or moiety would result in interruption of the chain.

Thus, and among various other backbones, especially preferred backbones include those that include multiple, optionally distinct peptide portions that are separated by multiple, optionally distinct carbohydrate portions. Most preferably, the peptide portion will comprise a synthetic or naturally occurring oligopeptide or polypeptide that is prepared or modified such that both ends of the linear sequence of amino acids have at least one amino group available for reaction with the respective reactive groups of the carbohydrate portions. For example, while one end of the peptide may be the N-terminus with an α-amino group, the other end of the peptide (i.e., the C-terminus) may be formed by a basic amino acid (e.g., lysine or arginine) or vice versa, which provides the amino group in a position other than the α-position (e.g., the ε-position for lysine). One exemplary section of a peptide backbone is illustrated in Formula II (e.g., wherein $R_1$, $R_2$, $R_3$, and $R_4$ are independently H, optionally substituted alkyl or aralkyl).

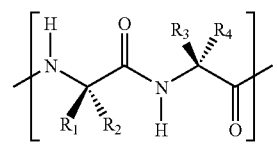

Formula II

Similarly, the carbohydrate portion of contemplated backbones may vary considerably and it is generally contemplated that the carbohydrate portion will include at least one or more monosaccharides or a polyol as defined earlier, which may independently be in an open-chain configuration or in a cyclic form. Most preferably, the carbohydrate portion includes a naturally occurring carbohydrate, but numerous carbohydrate analogs, synthetic carbohydrates, and all reasonable combinations thereof are also contemplated. Furthermore, naturally occurring carbohydrate portions will typically be modified in a manner such as to allow reaction with a reactive group of the peptide portions. Thus, it should be recognized that the terminal groups of the carbohydrate portion may be naturally occurring groups, especially including OH groups, CHO groups, and COOH groups. However, and where needed, it should be appreciated that suitable reactive groups may be introduced into the carbohydrate portion. For example, such reactive groups include specific leaving groups, carbonyl halides, etc. One exemplary section of a carbohydrate portion is depicted in Formula III (e.g., wherein R is independently H, OH, COOH, $CH_2OH$, alkoxy, $NH_2$, NHCO-Alkyl, optionally substituted alkyl or aryl).

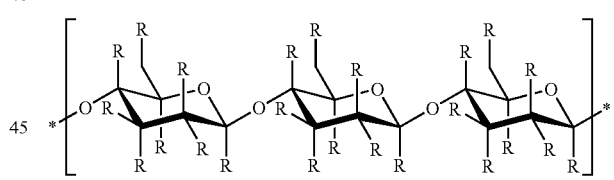

Formula III

Typically, the average molecular weight of contemplated compounds will be between about hundred to several hundred thousand, and even higher. Moreover, and depending on the particular structure of contemplated carbohydrate portions and/or amino acid portions, the backbone of contemplated compounds may be linear, linear with cyclic portions, branched, or cyclic. In still further contemplated aspects, the chimeric polymers according to the inventive subject matter may also include additional moieties/portions that are chemically distinct from the amino acids and/or carbohydrates contemplated herein. For example, suitable polymers may include carbohydrate and/or peptide moieties that are coupled to each other via an alkylene, polyethylene glycol, polyether, or other group or linker moiety. Most typically such an additional moiety/portion is covalently coupled to the amino acids and/or carbohydrates contemplated herein.

Furthermore, the backbone in contemplated compounds may also be branched. In such compounds, at least one of the carbohydrate and the amino acid will include one or more functional groups that can be coupled to another carbohydrate and/or amino acid. Most typically, the number of branches in contemplated compounds will depend on the particular structure of the carbohydrate and/or amino acid, and the desired use. Depending on the specific structures, branches may be used for crosslinking two or more backbones, and contemplated compounds may therefore also be viewed as three-dimensional networks. Alternatively, or additionally, branched polymers may also be synthesized by addition of multi-functional co-monomers, which may be coupled between the carbohydrate and/or amino acid moieties.

Of course, it should be appreciated that the carbohydrate moieties and/or the amino acid moieties can be prepared separately, and then coupled to each other to form a backbone. Such coupling may be directly (e.g., via an ester bond between a hydroxyl group of a sugar and a carboxylate group of an amino acid, or via an amide bond between a carboxylate group of a sugar and an amino group of a peptide) or indirectly via linker, which may be different from the carbohydrate and/or amino acid moieties (e.g., glycol linker). Alternatively, or additionally, cross linkers between two or more backbones comprising a sugar portion and an amino acid portion may be employed to increase structural complexity. Such cross linkers may comprise one or more carbohydrate moieties and/or amino acid moieties, or may be entirely different.

In additional aspects of the inventive subject matter, it is also contemplated that at least one end of the backbone is covalently coupled to a position in the backbone to form a cyclic structure. For example, where both ends of the backbone are covalently coupled to each other an entirely cyclic backbone is formed. Such cyclic backbones may be especially advantageous for providing improved resistance against exo-acting peptidases, esterases and glycosidases. In another example, one end of the backbone may also be coupled to a pendant functional group of the backbone to form a lariat-type structure (where such coupling occurs, double-lariats are also contemplated). In case of two cysteine residues within amino acid portions of such polymer, a cyclic structure with a disulfide (—S—S—) bond is also expected.

With respect to the sequence of the carbohydrate portion and/or the amino acid portion, it should be recognized that the sequences may be designed to a specific purpose or may also be a random sequence. For example, existing carbohydrate preparations (e.g., cell wall preparations from a plant cell) with uncharacterized chemical composition and structure may be coupled to characterized oligopeptides to form a hybrid substrate. Similarly, a peptide moiety may be isolated or synthetically prepared that includes a motif with a known function (e.g., Leucin-zipper, or helix-turn-helix structure, or cell surface binding epitopes such as RGD, etc.), and that moiety may then be coupled to a carbohydrate of characterized or uncharacterized origin. In yet further contemplated aspects, it should be recognized that at least one of the carbohydrate moiety and the peptide moiety may include at least a portion of a molecule with a known function. For example, carbohydrate moieties may include portions associated with cell-recognition, cell adhesion, small-molecule binding (e.g., lectin-type or ion-binding). Similarly, peptide moieties may include portions associated with catalytic function (oxidoreductase, hydrolase, lyase, ligase, etc.), chemical function (e.g., hydrolytic, proteolytic by certain enzymes, etc.), cell recognition function (e.g., RGD for integrin binding, etc.), structural function (e.g., collagen, myosin, tubulin, etc), or other function (e.g., growth factor, transcription factor, cytokine, chemokine, etc.). Furthermore, at least one of the carbohydrate and peptide moieties may function as pharmacologically active agents when they are degraded from their parent polymers. For example, one or more peptide moieties could have pharmaceutical activity (e.g., GnRH) once released from the adjacent carbohydrate moieties.

It should further be recognized that where the carbohydrate moiety and/or amino acid moiety has a known ligand, such ligands may be included in contemplated compositions. For example, where the amino acid moiety has a polyaspartic acid chain, cations (and especially $Ca^{2+}$ or $Mg^{2+}$) can be coupled (bound) to such moieties. Similarly, where the carbohydrate moiety has a known affinity to other carbohydrates (e.g., lectin), suitable ligands may be included in the composition. It should be particularly pointed out that further derivatizations, or deliberate use of amino acids and/or monosaccharides in the backbone may provide desirable properties to the chimeric polymer. For example, heteropolymers may be designed to have a specific net charge, charge ratio, or to be entirely neutral as depicted in the exemplary structures of Structure III below Structure III

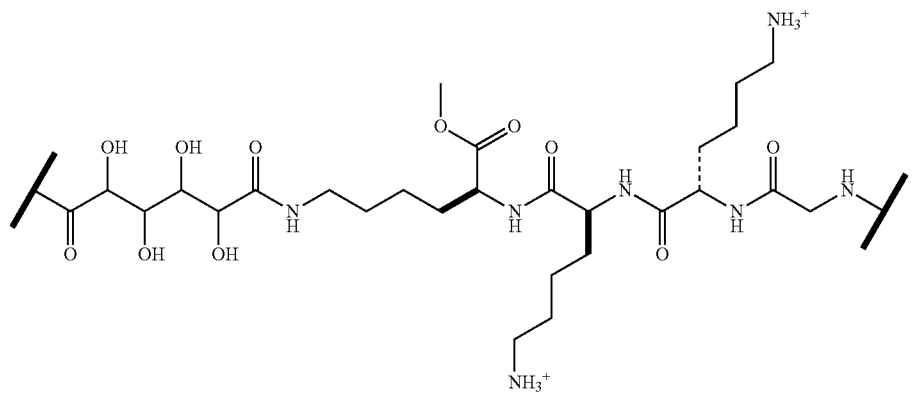

Polymer A: cationic

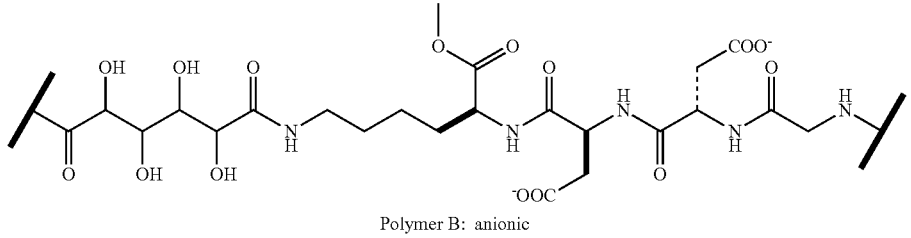
Polymer B: anionic
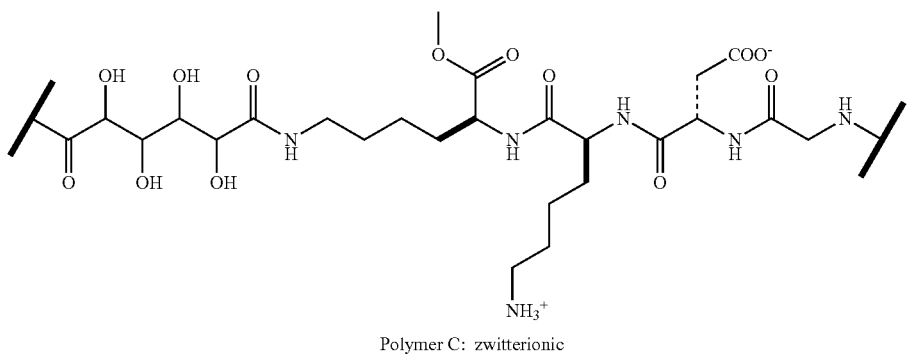
Polymer C: zwitterionic
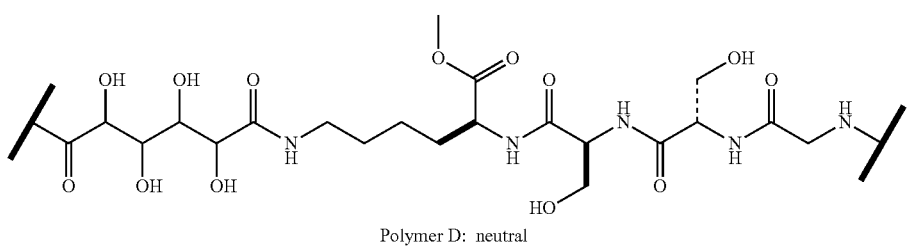
Polymer D: neutral
Similarly, heteropolymers may also be designed to have a specific interaction with aqueous solutions (e.g., to be hydrophilic, amphiphilic, or hydrophobic) as depicted in the exemplary structures of Structure IV below.
Structure IV
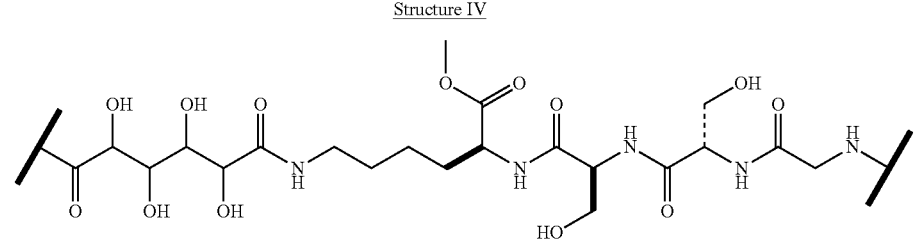
Polymer D: hydrophilic
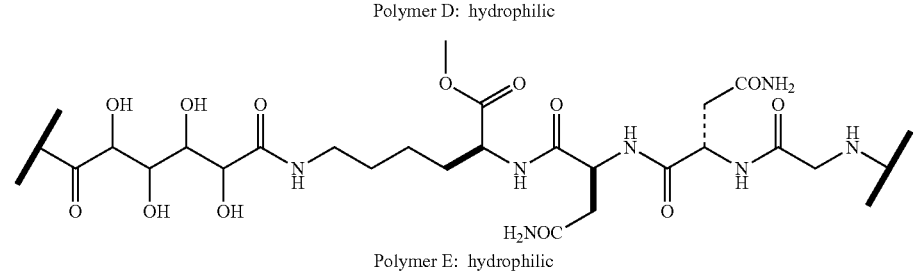
Polymer E: hydrophilic

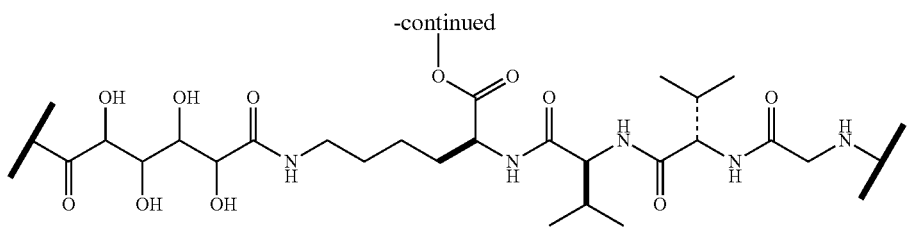

Polymer F: hydrophobic

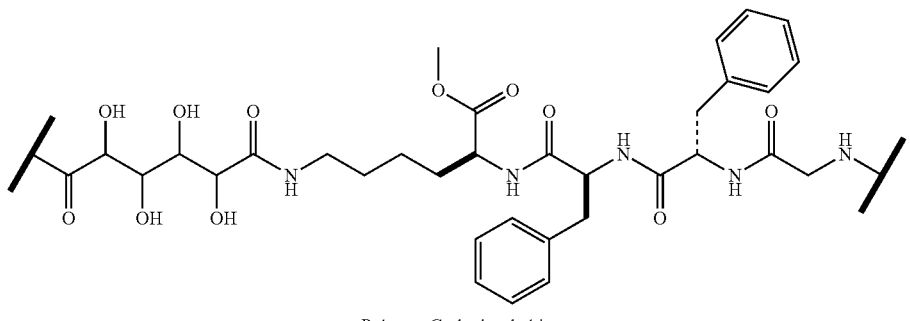

Polymer G: hydrophobic

Alternatively, or additionally, functional groups or other molecular entities may be added to the carbohydrate portion and/or the peptide portion to achieve a specific function of the chimeric polymer. For example, where contemplated materials are in contact with cells, it is contemplated that the peptide portion may include adhesion factors or other peptides that interact with surface components of a cell. Similarly, the carbohydrate portion may include lectins (e.g., as side chains) or antennary carbohydrates that interact with one or more surface components of a cell. Further contemplated modifications include one or more catalytic moieties, binding moieties, signal generating moieties, and/or crosslinking moieties that are attached to the backbone (either directly to an atom of the backbone, or via a pendant group off the backbone, or via externally added linker).

Thus, it should be appreciated that formation of a two- or three-dimensional network of contemplated compounds may be formed concurrent with the formation of the backbones, but also separately in a reaction in which crosslinking backbones (or other structures, see below) are added to a plurality of prefabricated backbones. For example, where reactive pendant groups are attached to the backbone (e.g., phenolic groups of tyrosine from peptide portion), such groups may be employed as crosslinking targets using one or more crosslinking agents.

Contemplated Uses

The inventor unexpectedly discovered that at least some of (and most likely many of) contemplated compounds are low- to non-toxic in an in vitro and even in vivo system, and that such compounds exhibit superior biocompatibility. Thus, the compositions and methods presented herein are thought to be especially valuable in in vivo and/or in vitro applications where the chimeric polymers play a structural, physiological, and/or pharmacological role. Among other exemplary uses, contemplated heteropolymers may act as a coating material for medical devices (e.g., for temporary or permanent implants), as a drug delivery vehicle (e.g., for interferon, insulin, etc., with or without time release properties), as a resorbable or permanent scaffold for cell cultures (e.g., in tissue culture or for culturing stem cells), as food and nutraceutical components and additives, as topical and internal non-toxic excipients for cosmetic applications, and/or as a bulk implant material. It should be recognized that, depending on the peptide structure, contemplated polymers may undergo a sol-gel transition with a change in pH, temperature, and/or ionic concentration useful for oral, mucosal or topical applications.

It should be recognized that there are numerous uses for contemplated compositions, and that the particular use will determine at least in part the specific structure, and vice versa. Among other uses, especially contemplated uses include those in which the compounds according to the inventive subject matter are employed as biocompatible structural elements or coatings, as carriers of a pharmaceutical agent, as scaffold for other (optionally releasably attached) molecules, as a drug delivery vehicle (with or without time release properties), as resorbable or permanent scaffolds for cell cultures (e.g., in tissue culture), as food and nutraceutical components and additives, as topical and internal non-toxic excipients for cosmetic applications, and/or as implant material. For example, preferred biocompatible structural elements include topical and injectable cosmetic compositions that may support a tissue, wherein the composition may include collagen or collagen fragments, and wherein the collagen is coupled to another collagen via an 1-4-alpha-glycosidic oligosaccharide. Alternatively, the structural element may act as a support for a cell culture to assist in the formation of a specific tissue and/or organ. In such examples, it is preferred that contemplated compounds are relatively hydrophilic and will have a gel-like consistency. Furthermore, such compounds are preferably biocompatible for growing stem cells.

Biocompatible coatings may include those in which a (metal) implant is covered with contemplated compounds to reduce implant/tissue rejection. Where contemplated compounds are utilized as drug carriers, it should be recognized that the release of the drug may be controlled in numerous manners. For example, the drug may be encapsulated by the biocompatible biopolymer, and biodegradation and/or erosion may liberate the drug in a predetermined manner. Alternatively, or additionally, the drug may be covalently, ionically, or otherwise coupled to the carbohydrate and/or peptide moiety such that an enzymatic (e.g., an esterase or peptidase) or non-enzymatic reaction (e.g., via oxido-reduction) will liberate the drug. For example, positively charged polymers may be employed as gene delivery vehicles in which the positive charges of amino acids in the polymer interact with the negatively charged phosphate groups of the nucleic acid. In yet further contemplated aspects, the compounds according to the inventive subject matter will act as a scaffolding to attach one or more molecular entities in a predetermined or random fashion. Such compounds may serve, for example, as carriers for combinatorial libraries and the macromolecular scaffolding will act as a derivatizable solid phase.

In yet further contemplated aspects, the materials according to the inventive subject matter may be employed as a layered coating on a desired biological structure (e.g., intima layer of a blood vessel) or non-biological structure (e.g., stent). Most preferably, layered coatings may comprise alternating layers in which one layer has a positive net charge at a pH, while the other layer has a negative net charge at the same pH. Such multi-layered coatings can be prepared by the well-documented layer-by-layer deposition method. Such layers will strongly adhere to each other, predominantly due to Coulomb interactions. Moreover, and especially where the layers are formed on a stent, it is contemplated that at least one of the layers may include a cell and/or a NO-releasing compound, and most preferably endothelial cells and nitroprusside.

EXPERIMENTS

General Considerations

Contemplated Synthetic Routes

Based on the relatively simple chemistry and numerous well-known procedures for same, many of the permutations can be produced in a conceptually undemanding manner. Most preferably, synthesis of the chimeric polymers is performed using preformed peptide portions and preformed carbohydrate portions. For example, peptide portions and carbohydrate portions can be covalently coupled to each other through amide bond formation between carboxyl and amino end groups from the peptide and carbohydrate monomers. In another route, peptide portions and carbohydrate portions can be covalently coupled to each other using a ring-opening polymerization of a dilactone with a peptide having two terminal amino groups as shown below in Scheme I.

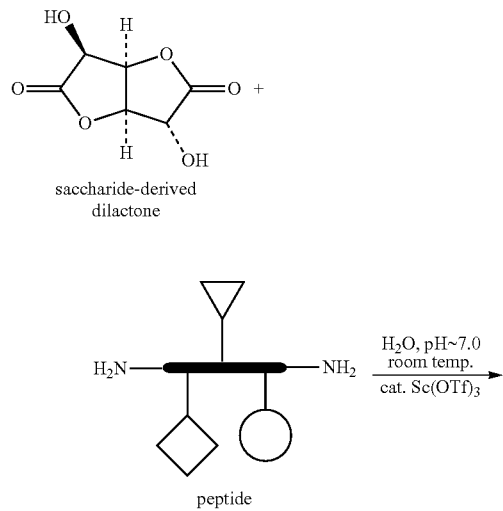

-continued

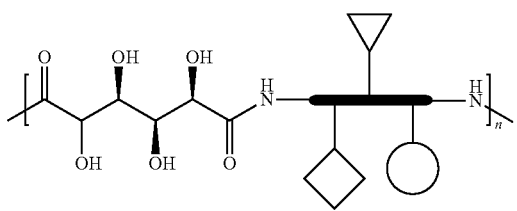

Alternatively, the carbohydrate portion may be modified to have terminal azido groups that are then reacted with a peptide having terminal acetylene groups using Click chemistry to form the chimeric polymer as exemplarily depicted in Scheme II below.

Scheme II

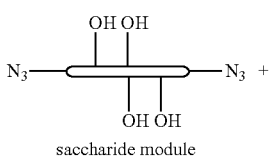

saccharide module

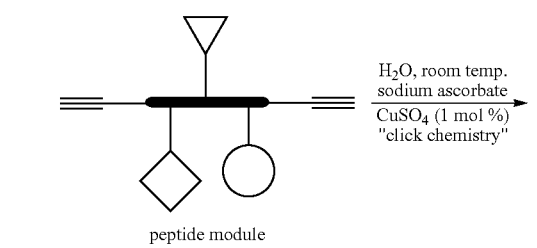

peptide module

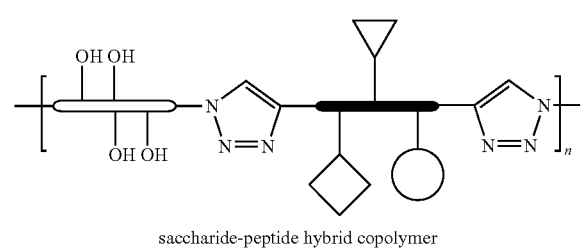

saccharide-peptide hybrid copolymer

In yet another contemplated approach, the peptide portion is modified to include terminal hydroxylamine groups, while the saccharide portion is modified to include terminal α-ketoacids groups. Polymerization to the chimeric molecule is then effected by condensation of the N-alkylhydroxylamines with the α-ketoacids as depicted in the example of Scheme III below.

Scheme III

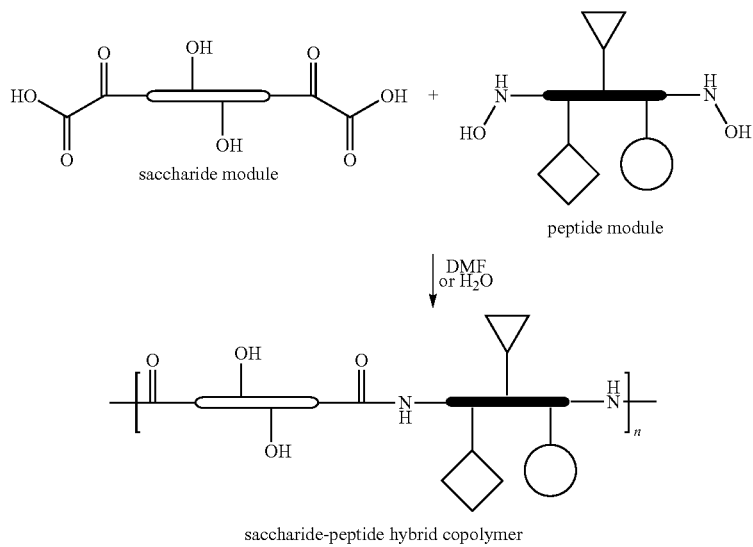

saccharide-peptide hybrid copolymer

Crosslinking of Contemplated Polymers

Crosslinking of the so prepared chimeric polymers can be performed in numerous and relatively simple manners. Most typically, crosslinking can be performed using addition of exogenously added crosslinkers that form (covalent) bonds with pendant groups of the backbone, and/or may be performed using chemistry already present in the backbone and/or pendant groups. For example, as depicted in Scheme IV below, a chimeric polymer is prepared from a tyrosine-containing tripeptide having terminal amino groups and a saccharide portion having activated terminal acid groups as acid chlorides. The so formed chimeric polymer is then crosslinked either in a peroxidase-initiated reaction or in a photo-catalyzed oxidation reaction to form the phenyl linkage between the backbones. Additional and/or alternative manners of crosslinking, for example disulfide (—S—S—) linkage resulting from cysteine residues in the backbone are also contemplated and especially include those in which the interaction between the polymers is a non-covalent interaction. For example, suitable crosslinking interactions include ionic ($NH_3^+$ and $COO^-$), hydrogen bonding interactions between OH, $NH_2$, COOH, SH, $CONH_2$), and hydrophobic interactions resulting from Van der Waal forces.

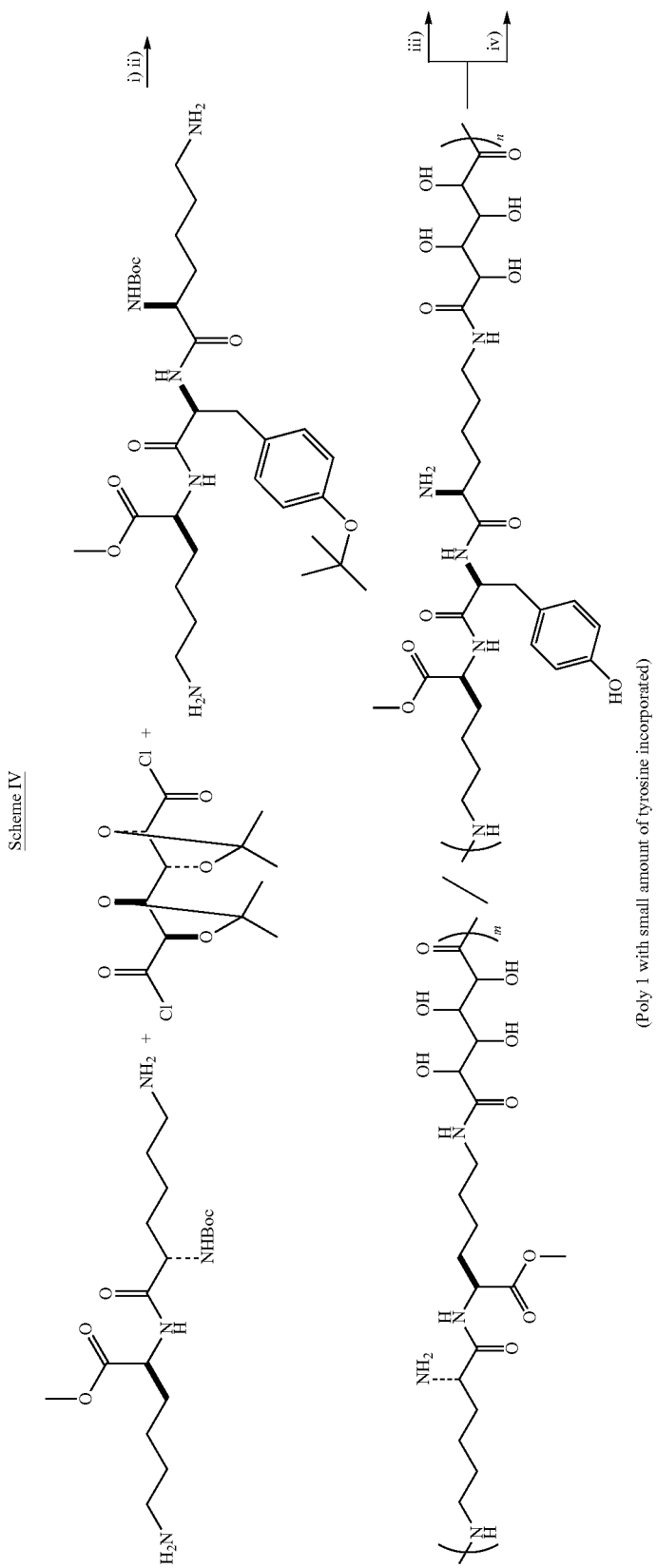

-continued
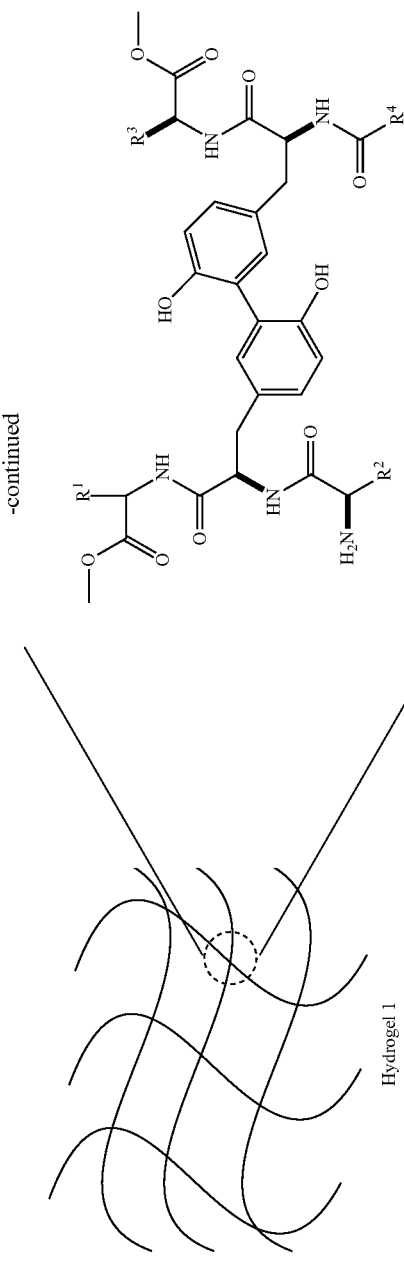
Hydrogel 1
Reaction conditions:
i) Interfaciatl polymer, H$_2$O/CCl$_4$;
ii) 50% TFA/H$_2$O
iii) Horse radish peroxidase (HRP), HOOH;
iv) Ru(II) and ammonium persulfate (APS)

Preparation of Functionalized Chimeric Polymers

Similar to crosslinking, functionalization can be carried out in numerous manners and may be employed by adding exogenous functional groups (e.g., labels, binding portions, catalytic portions, pharmaceutically active portions, etc.), and/or by inclusion of functional groups in the pendant groups of the backbone and/or the backbone itself. The functionalization can be either done through copolymerization of functional comonomers or through post-polymerization functionalization. One exemplary manner of functionalization is provided in Scheme V below in which an RGD peptide modified peptide portion is combined with other non-modified peptide portions using ring-opening polymerization chemistry as depicted above.

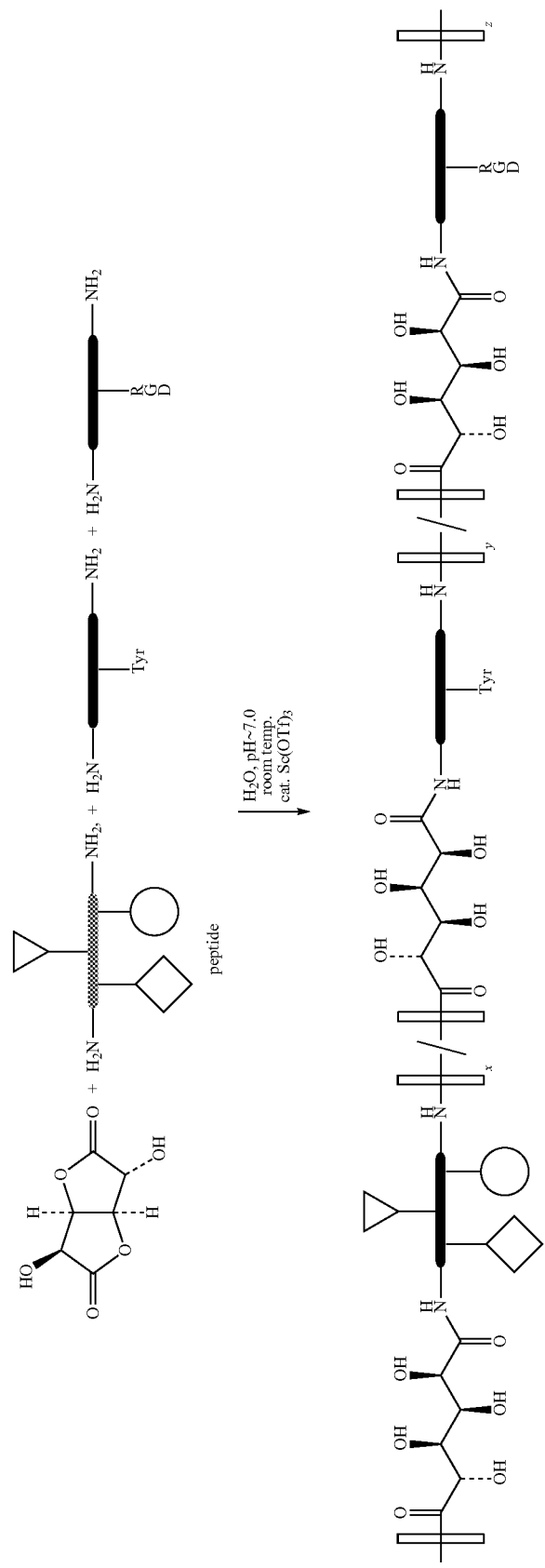

Synthetic Examples

The following protocols and procedures are provided as an exemplary guidance for a person of ordinary skill in the art. However, they should not be considered limiting to the inventive subject matter as the amino acid/peptide component and/or the carbohydrate component may be easily replaced by equivalent components without departing from the inventive concept presented herein. Exemplary variations are presented in, among other places, the contemplated carbohydrate and contemplated peptides and amino acid sections above. Some of the exemplary chimeric polymers (see Structure V: dilysine, trilysine, and tetralysine-derived galactara copolymers) were tested in an in vitro and in vivo environment as described below.

As described further below, Poly 1-3 were tested for gene delivery applications. As contemplated structures are highly adaptable, structural variations can be made with relative ease to optimize gene transfection levels while maintaining relatively low levels of cytotoxicity. Initial manipulations were performed involving lengthening the peptidyl monomer sequence with additional L-lysine residues to thereby increase the charge density of the polymer overall and to thereby offer stronger DNA binding. It should be recognized that where increased charge density improves the gene transfectability of the polymer system, more residues can be added until an optimal length is found. The pentalysine monomer was found to be insoluble in water, or water/solvent mixtures. For this reason, solution phase polymerizations were attempted to yield small polymer chains and cyclic structures. One example of cyclic structures is given in Structure VI below.

Structure V

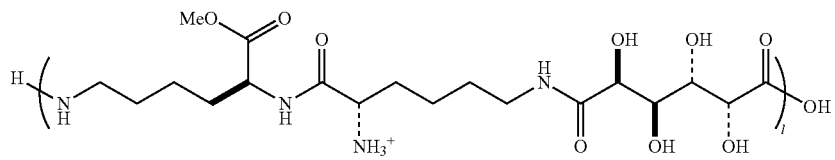

Poly 1

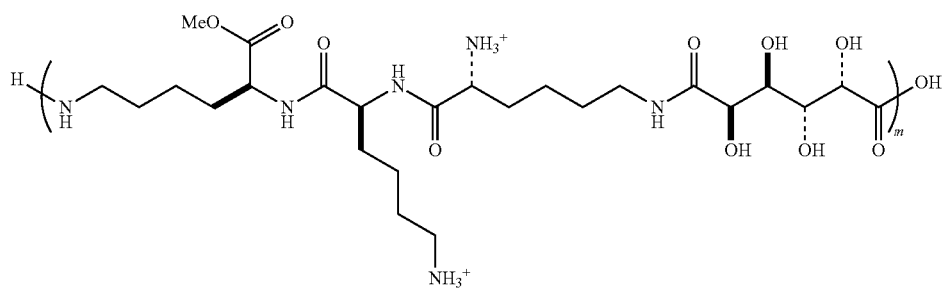

Poly 2

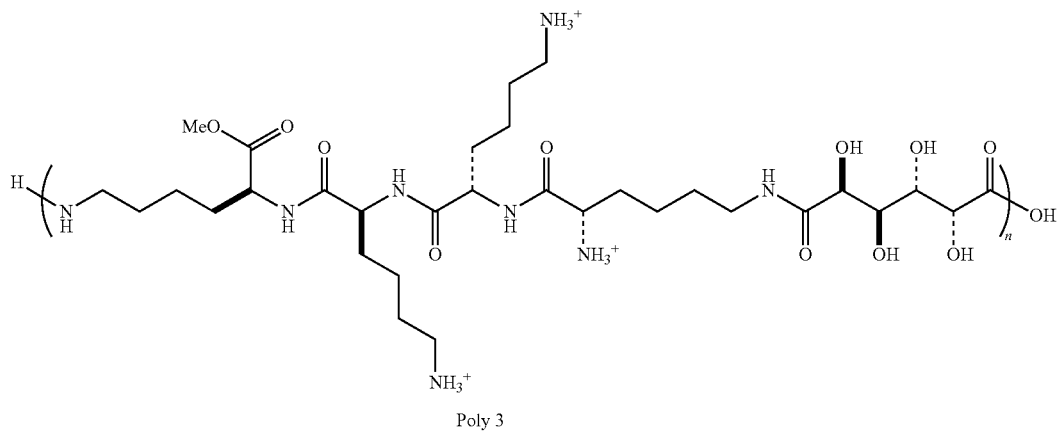

Poly 3

Structure VI

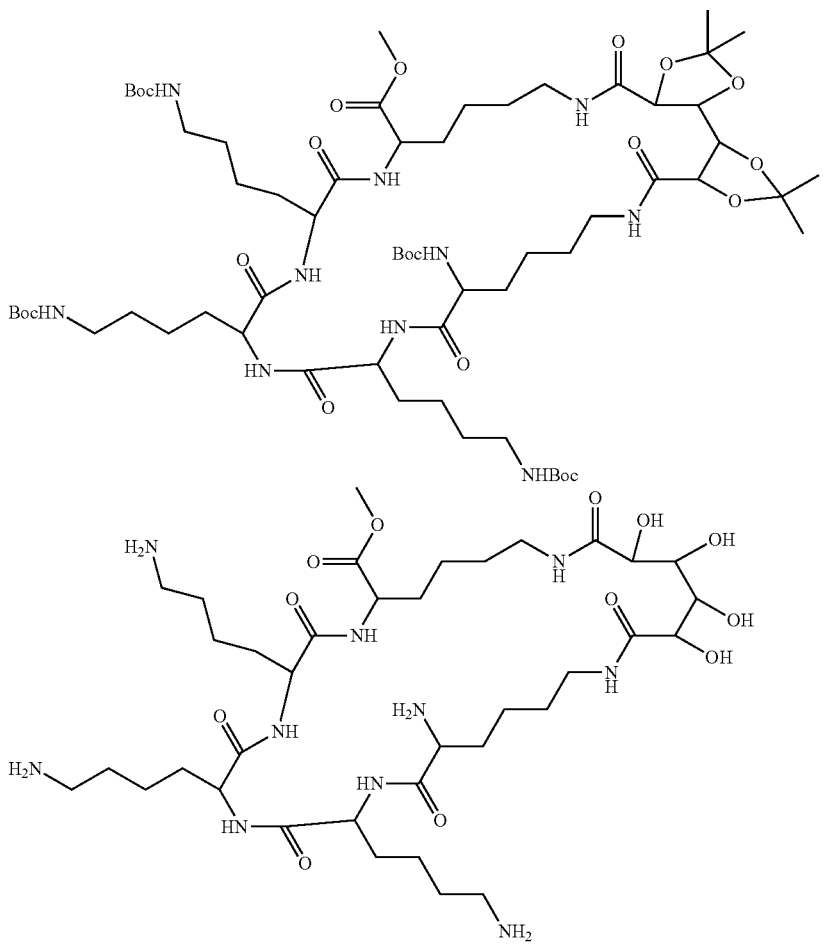

(top: protected form; bottom: after deprotection)

Further synthetic routes were attempted to form the hexalysine polymer in solution phase. Using such approach, the polymer chains did form, however, with some cycle formation. The Mn for the above polymerizations was around 70,000 and the Mw was upwards of 2,000,000. The multimodal MW distribution of the above polymers (as evidenced in HPLC elution) indicates that there may be several different polymerization mechanisms at work. Scheme VI depicts Polymerization of the heptalysine monomer using coupling reagents (Reaction conditions: 10:1 DMF/water, EDC 4.4 eq., DMAP catalytic, TEA 2.2 eq.).

Scheme VI

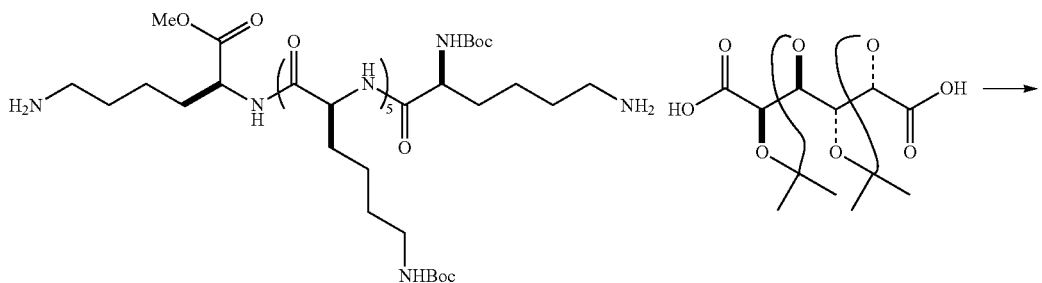

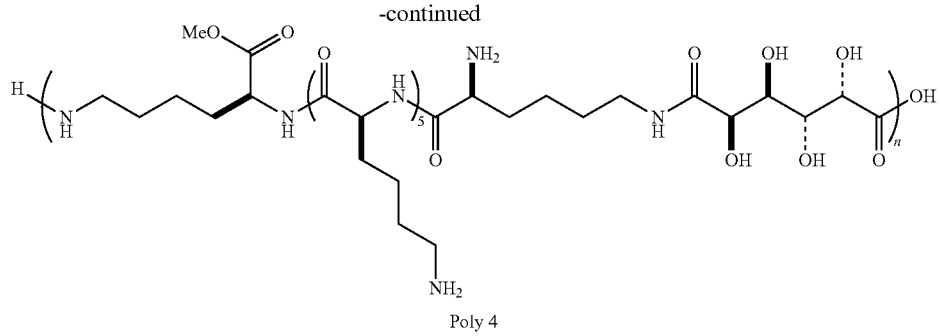

Poly 4

In a different approach the inventor noted that by adding a histidine residue, a proton sponge effect could be achieved while the polymer is inside the cell, allowing endosomal escape. As a potential consequence, chloroquine addition in heretofore known transfections escape. As a potential consequence, chloroquine addition in heretofore known transfections would no longer be needed as an additive for healthy transfection of DNA to the cell nuclei. Structure VII depicts exemplary polymers with histidyl linkers, and Structure VIII depicts an exemplary histidine monomer that was synthesized for use in polymerizations.

Structure VII

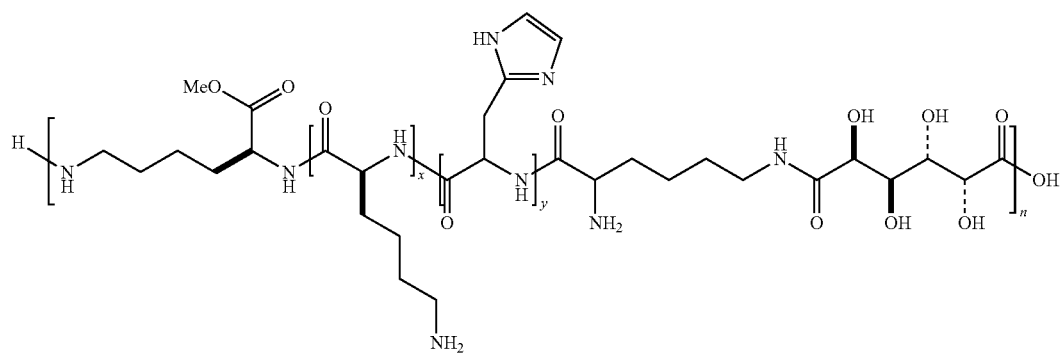

Structure VIII

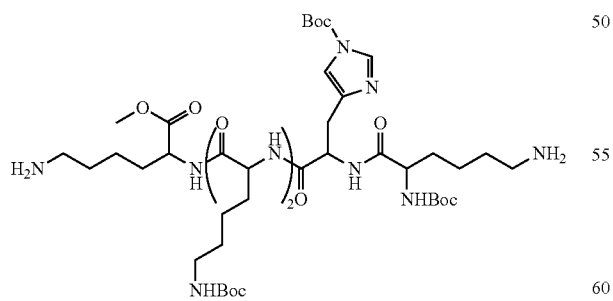

Scheme VII below illustrates an exemplary scheme for polymerization of the histidine containing monomer (Reaction conditions: Water, MeOH, $Na_2CO_3$, $CCl_4$). As is shown by the Mn, the polymerization conditions may be further optimized.

Scheme VII
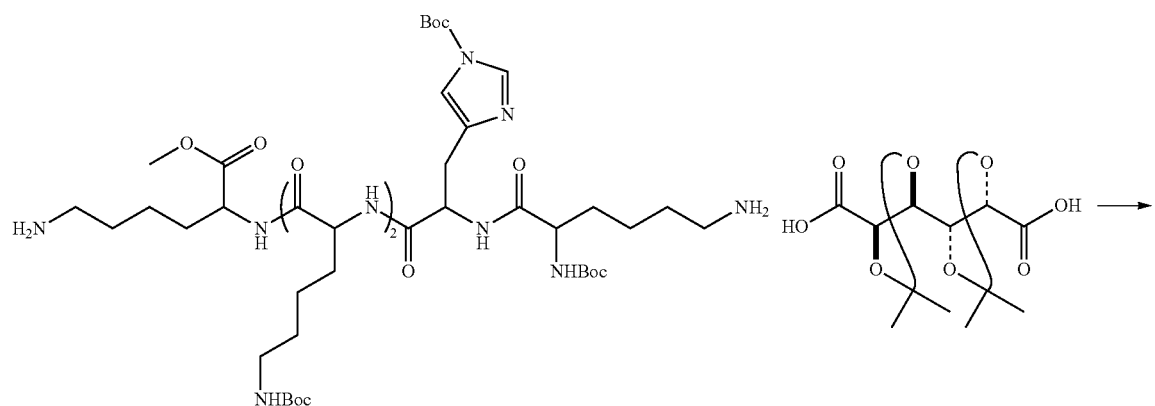
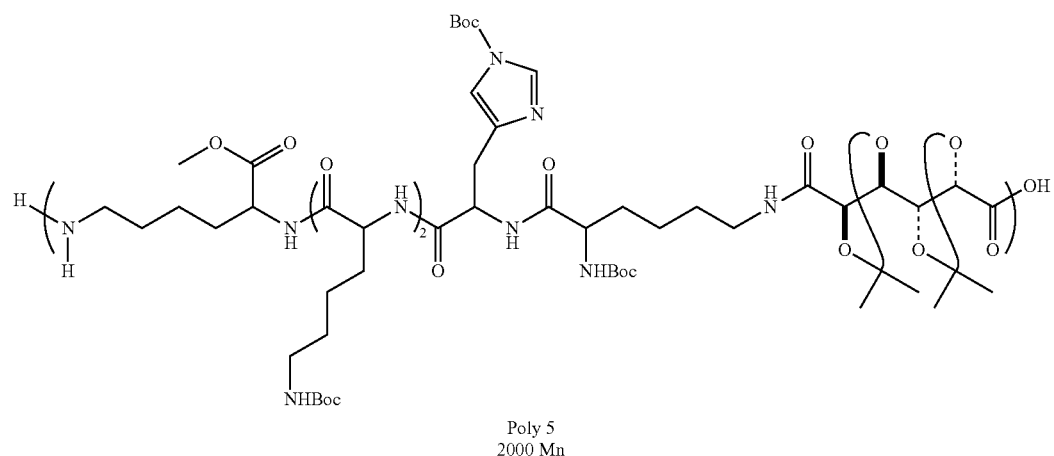
Poly 5
2000 Mn
Improved Carbohydrate-Peptide Copolymer Synthesis Results
The synthesis of the histidine monomer was completed at large scale to test further polymerization conditions. One exemplary route for the synthesis of the histidine-containing peptide portion is illustrated in Scheme VIII
Scheme VIII
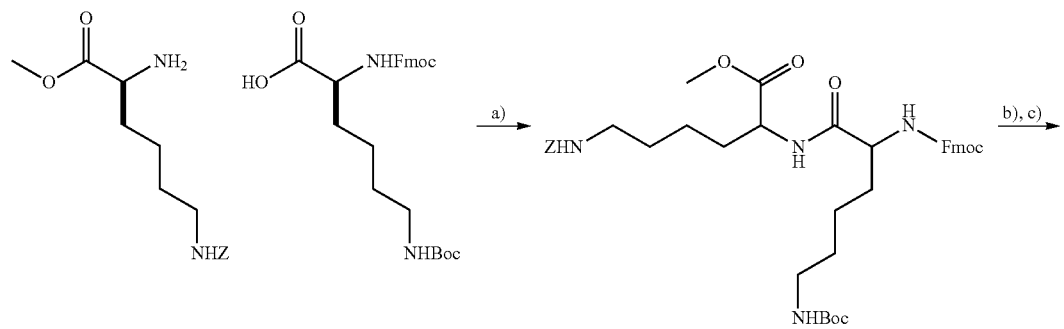

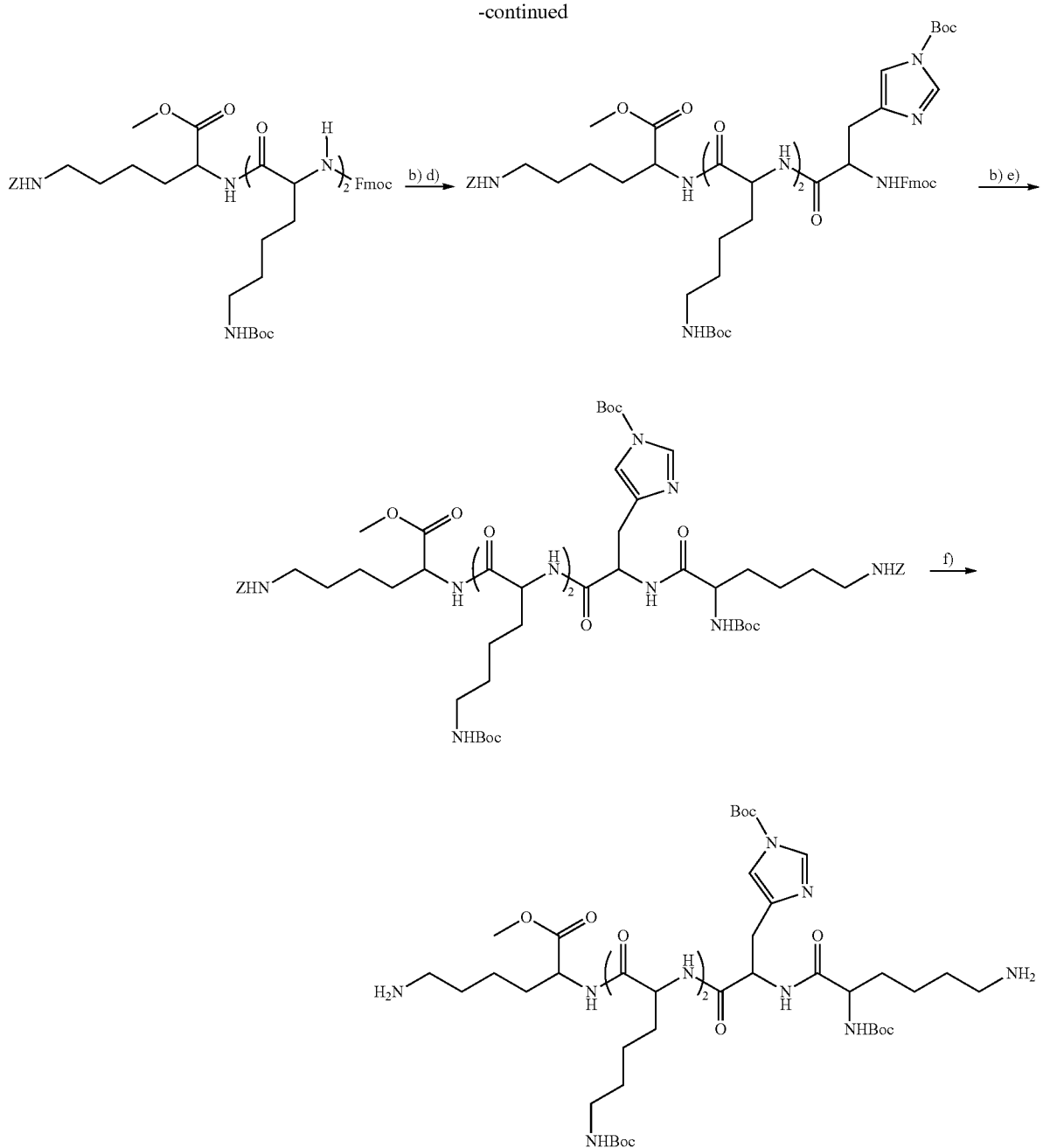

Figure 5:
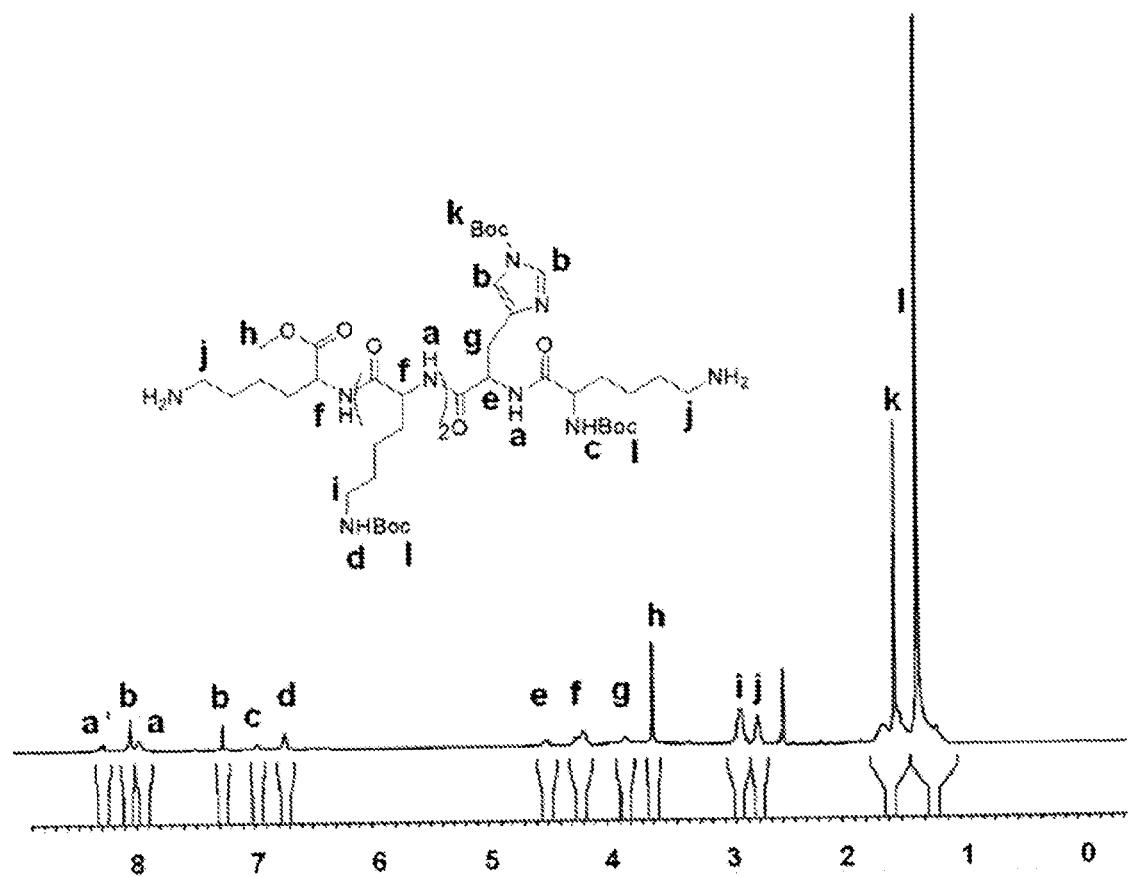
FIG. 5 depicts a $^1$H NMR spectrum obtained during synthesis of the histidine monomer as set forth in Scheme VIII.

Reaction conditions were: a) coupling with EDC/HOBt, b) deprotection with dimethyl amine (DMA) in THF, c) coupling with EDC/HOBt/FmocHis(Boc)OH, d) coupling with EDC/HOBt/FmocLys(Boc)OH, e) deprotection using $H_2$ Pd/C. This synthesis was brought to compound prior to the final monomer, and upon hydrogenation and isolation of the final monomer, it was noted by $^1$H NMR and ESMS that the compound had lost some Boc protecting group (Peak "k" disappeared during deprotection) as shown in the spectrum provided in FIG. 5.

Such event is likely at the z-nitrogen as evidenced by NMR. The protecting group in this position is more labile than typical Boc groups because it is located on an imidazole ring. To overcome potential problems in subsequent steps, alternative routes to varying polymers were explored. Structure IX shows exemplary penta, hexa, and hepta monomers.

Structure IX

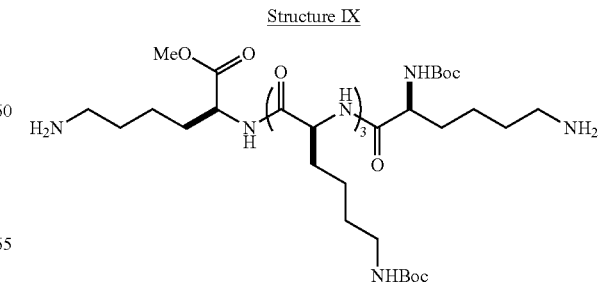

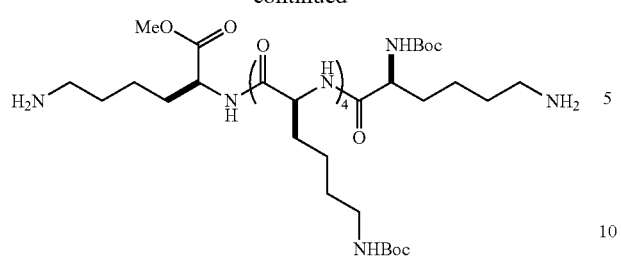

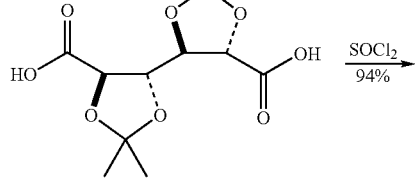

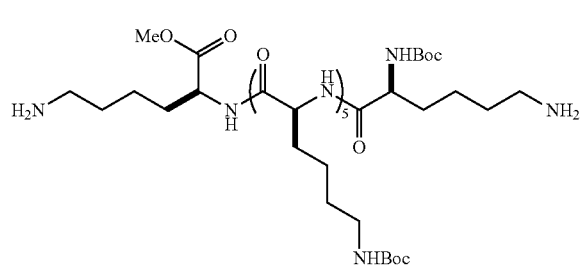

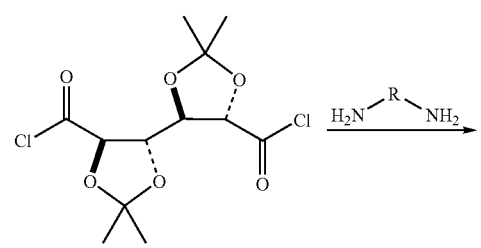

Carbohydrate Monomer Simplification

Based on initial experiments, it appeared that the sugar monomer synthesis can be shortened to a one step esterification, to yield a compound that can undergo condensation reactions with a diamine to form amide bonds as shown in Scheme IX. This route is the acid chloride route to form the polyamide vs. condensation reaction to form the polyamide.

Scheme IX
CURRENT ROUTE

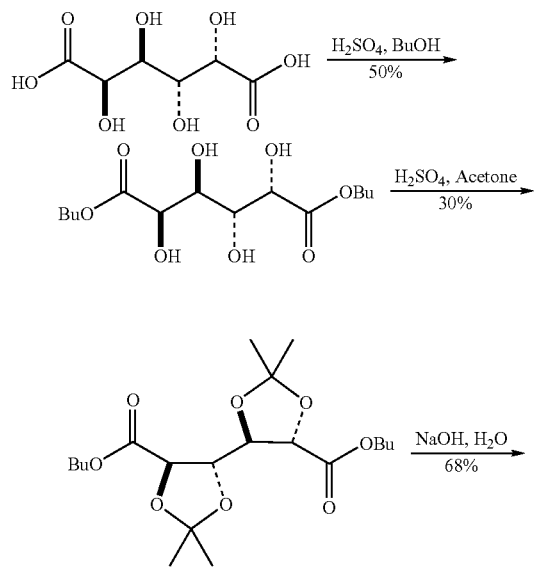

NEW ROUTE

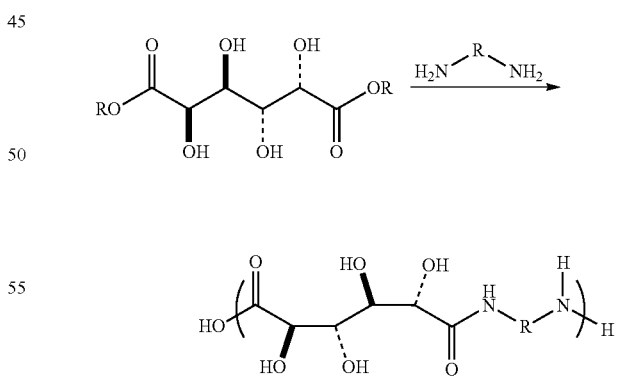

It should be noted that if this route were feasible in forming high Mn polymer, it would cut out three steps in the synthesis. The following Scheme X (condensation reactions with the dilysine monomer and diesters) shows the results of two attempts to form dilysine-sugar copolymers in this fashion. Remarkably, these attempts gave relatively low yields of polymer. However, optimization of reaction conditions is expected to provide improved yields.

Scheme X

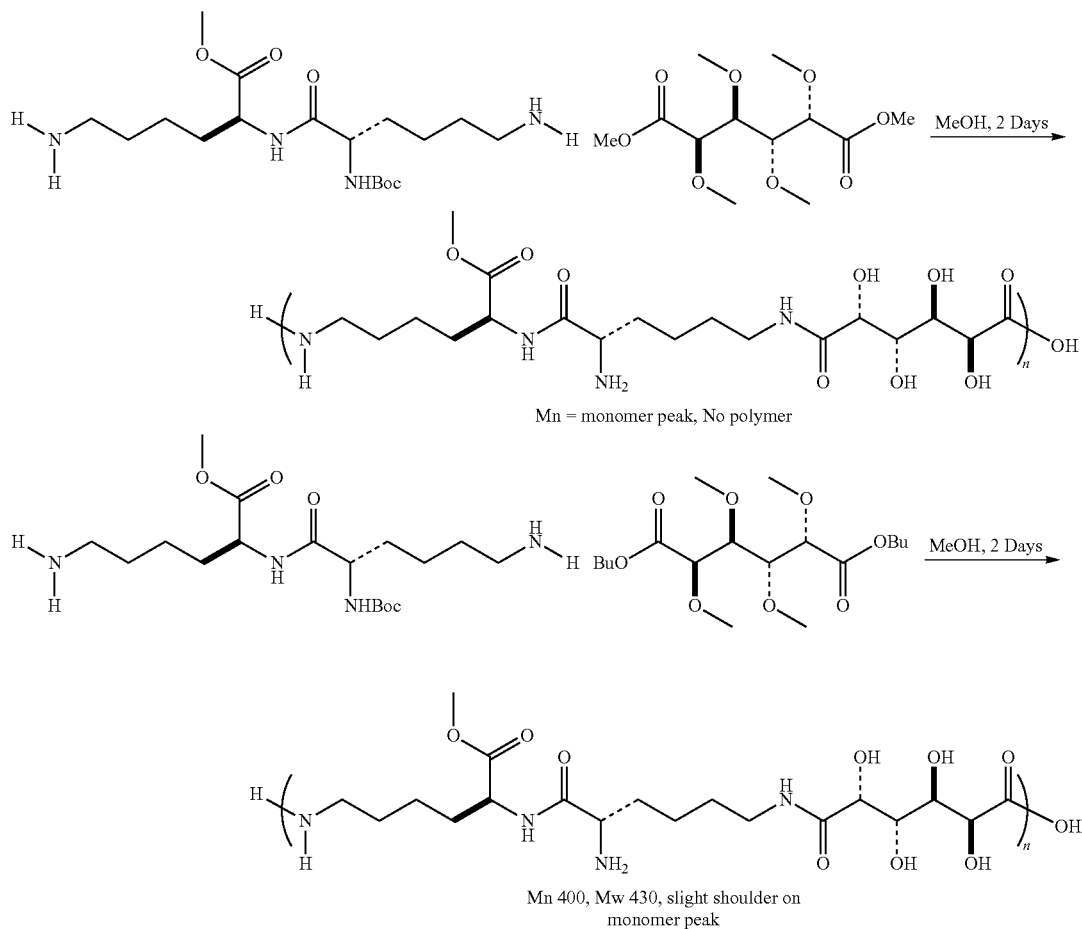

Peptide Monomer Simplification

Based on earlier transfection results, the inventor found that the trilysine polymer gave the highest levels of transfection and that the tetralysine gave comparable results. In a further approach, histidine residues were added. These residues are thought to have a proton sponge effect that could raise the transfection levels of the polymer. It was contemplated that high binding efficiency (from lysine residues) and low pKa moieties (from histidine residues) was needed. Therefore, an ABC copolymer was prepared with a lysine monomer, a histidine monomer and a carbohydrate monomer as depicted in Scheme XI below:

Scheme XI

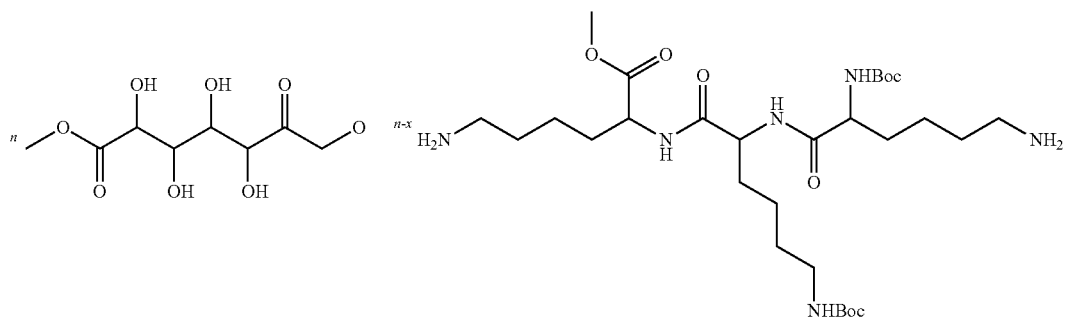

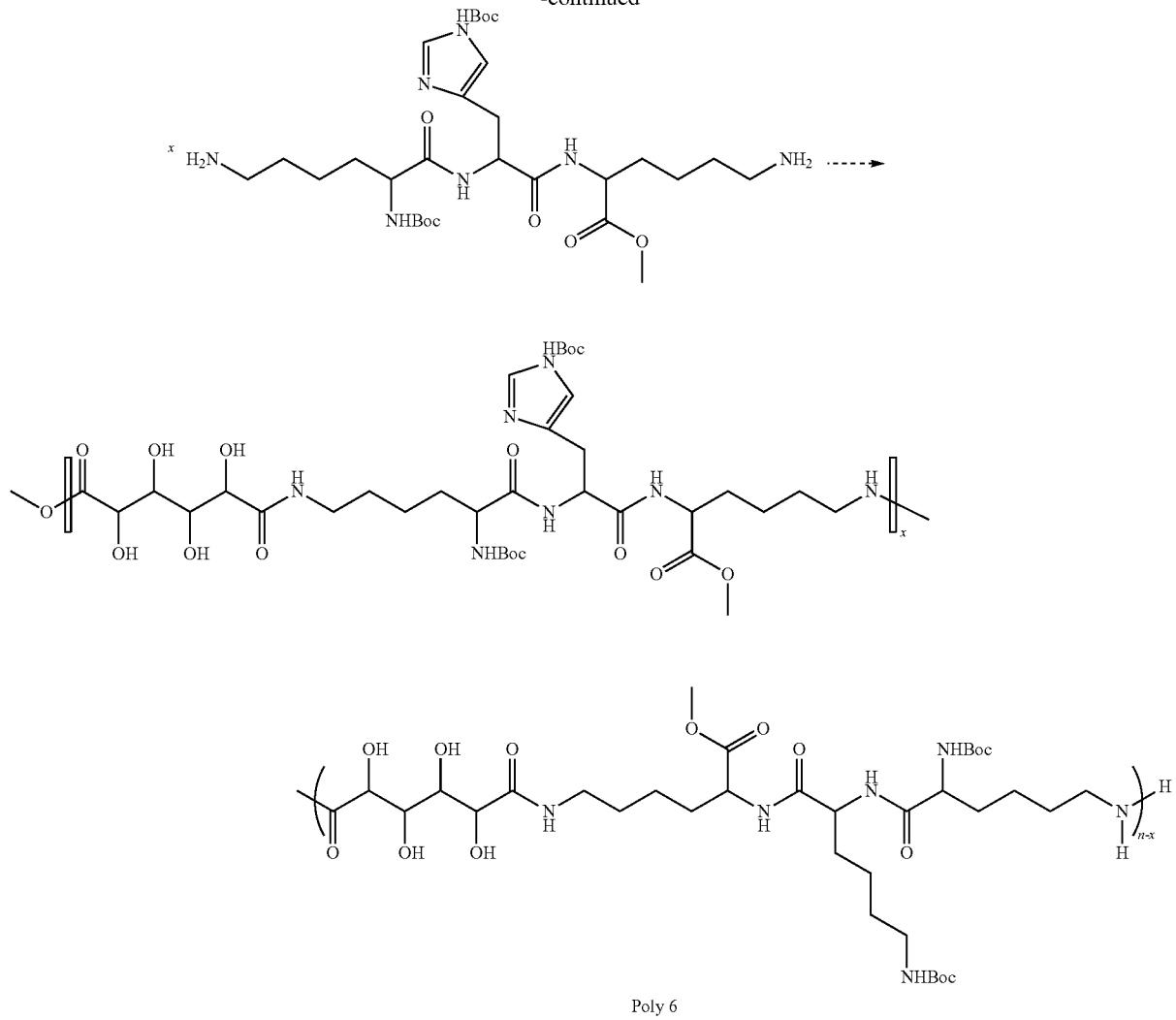

Poly 6

It should be noted that this polymer is not only more easily accessible (as far as a more convergent synthesis), but also that the polymer is highly versatile. Furthermore, different amounts of the histidine and lysine monomer may be added to give different incorporation ratios of the functional groups, leading to different polymers with different properties. Structure X depicts exemplary Z protected monomers.

Structure X

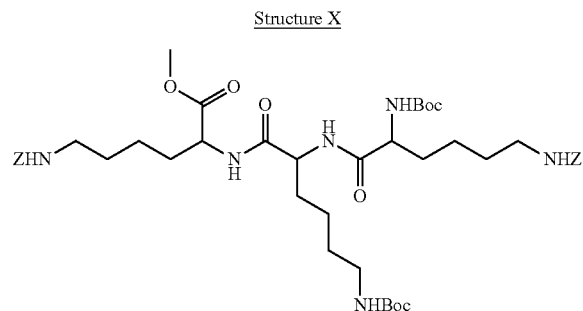

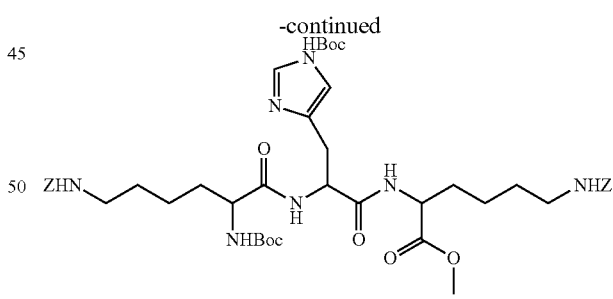

Materials:

Reagents were used as received from Aldrich (Milwaukee, Wis.), with the exception of the amino acids and coupling reagents, which were purchased from NovaBiochem (San Diego, Calif.). All reactions were performed under a nitrogen atmosphere with the use of flame-dried glassware. All solvents used in water-sensitive reactions were dried and purified via distillation or from an alumina filtration system. Extraction solvents were commercial grade. Flash chromatography was performed using forced flow of indicated solvent systems over Fisher silica gel 60 (230-400 mesh).

General Considerations:

Gel Permeation Chromatography (GPC) was carried out using an Agilent 1100 Series GPC-SEC Analysis System along with a mixed bed Plgel Mixed-C column from Polymer Labs. The eluent was THF, and a flow rate of 0.5 mL/min was used. The calibration was performed using Aldrich polystyrenes as standards. $^1$H NMR spectra were acquired using 500 MHz Bruker instruments and $^{13}$C NMR with 125 MHz Bruker instruments. NMR chemical shifts were reported as δ values in ppm relative to TMS or deuterated solvent. Data are presented as follows: chemical shift, multiplicity (s=singlet, d=doublet, t=triplet, q=quartet, m=multiplet), coupling constant(s) in Hz and integrations. Multiplets are reported over the range (in ppm) in which they appear. Carbon NMR data were recorded relative to solvent signals. Mass spectral data was obtained on a Micromass autospec spectrometer. Combustion analyses were performed by Atlantic Microlab (Norcross, Ga.).

1

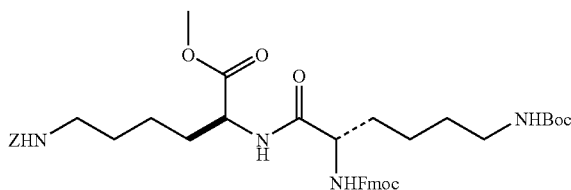

Synthesis of Fmoc-Lys(Boc)-Lys(Z)-OMe.

To a solution of diisopropylethyl amine (2.8 mL, 16.1 mmol) in DCM (100 mL) at 0° C., was added Lys(Z)OMe (5.0 g, 15.1 mmol). To this solution was added FmocLys(Boc) OH (7.08 g, 15.1 mmol), then HOBt (2.04 g, 15.1 mmol), and finally EDC.HCl (2.90 g, 15.1 mmol). This solution was allowed to stir for 8 h at which time the organic solution was washed with 1N HCl (3×20 mL), then saturated NaHCO$_3$ (3×20 mL), and finally H$_2$O (3×20 mL). The organic layer was concentrated in vacuo to yield a white solid (1) (9.81 g, 87% yield): $^1$H NMR (500 MHz, CDCl$_3$) δ 7.79 (d, J=7.51, 2H), 7.63 (d, J=7.23, 2H), 7.42-7.32 (m, 9H), 7.20 (s, 1H), 5.95 (s, 1H), 5.70 (s, 1H), 5.25 (s, 1H), 5.15 (m, 1H), 5.05 (s, 1H), 4.92 (s, 1H), 4.60-4.21 (m, 6H), 3.75 (s, 3H), 3.18-3.09 (m, 5H), 2.00-1.65 (m, 6H), 1.47 (br s, 27H), 1.40-1.25 (m, 6H); $^{13}$C NMR (125 MHz, CDCl$_3$) δ 173.1, 172.0, 157.1, 156.7, 156.6, 144.2, 141.7, 137.17, 128.9, 128.6, 128.5, 128.3, 128.2, 127.6, 125.6, 125.5, 120.4, 79.5, 67.5, 67.2, 66.9, 55.2, 54.0, 53.7, 52.8, 52.5, 47.5, 40.8, 40.4, 40.3 (2), 32.6 (2), 31.8 (2), 29.9 (3), 29.6, 28.9, 28.8, 23.0, 22.8; HRMS (FAB) m/z calcd for C$_{41}$H$_{52}$N$_4$O$_9$ (M+Na)$^+$ 767.3632, found 767.3645.

2

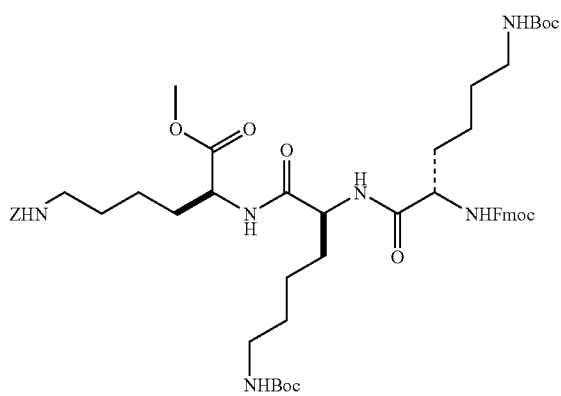

Synthesis of Fmoc-Lys(Boc)-Lys(Boc)-Lys(Z)-OMe (2).

To a solution of 1 (4.16 g, 5.58 mmol) in THF (55 mL), was added dimethyl amine (28 mL, 2M, 56.0 mmol) at 0 OC. This reaction was allowed to reach room temperature and was stirred for 2 h. At this time, the reaction mixture was concentrated in vacuo. To the yellowish solid, was added DCM (75 mL) and DMF (25 mL). To this solution, was added Fmoc-Lys(Boc)-OH (2.18 g, 4.64 mmol), then HOBt (0.627 g, 4.64 mmol), then EDC.HCl (0.890 g, 4.64 mmol). This solution was allowed to stir for 8 h at which time the organic solution was washed with 1N HCl (3×15 mL), then saturated NaHCO$_3$ (3×15 mL), and finally H$_2$O (3×15 mL). The organic layer was dried over MgSO$_4$ and concentrated in vacuo to yield a white solid. Column chromatography (2% MeOH, CHCl$_3$) afforded the product 2, (3.42 g, 63% yield): $^1$H NMR (500 MHz, CDCl$_3$) δ 7.74 (d, J=7.55, 2H), 7.58 (d, J=7.35, 2H), 7.38-7.25 (m, 15H), 7.00 (br d, 2H), 5.50 (br, s, 1H), 5.16-5.09 (m, 5H), 4.55 (br s, 1H), 4.36 (m, 3H), 4.25-4.10 (m, 2H), 3.61 (s, 3H), 3.16-3.10 (m, 6H), 1.81-1.39 (m, 23H); $^{13}$C NMR (125 MHz, CDCl$_3$) δ 173.1, 172.0, 157.1, 156.74, 156.6, 144.2, 141.7, 137.2, 128.9, 128.6, 128.5, 128.3, 128.2, 127.6, 125.6, 125.5, 120.4, 79.5, 67.5, 66.9, 55.2, 52.8, 52.5, 47.5, 40.8, 40.4, 40.3, 32.6, 31.8, 29.9, 29.6, 28.9, 28.8, 23.0, 22.8; HRMS (FAB) m/z calcd for C$_{52}$H$_{72}$N$_6$O$_8$ (M+Na)$^+$ 995.5106, found 995.5132.

3

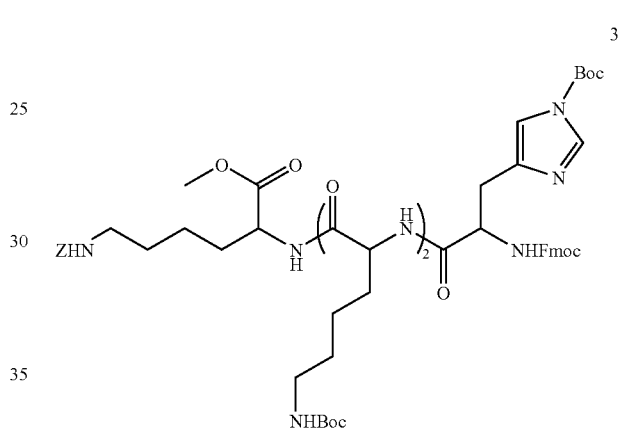

Synthesis of FmocHis(Tr)-Lys(Boc)-Lys(Boc)-BocLys (Z):

To a solution of Fmoc-Lys(Boc)-Lys(Boc)-BocLys(Z) (4.83 g, 4.97 mmol) in THF (100 mL), was added dimethyl amine (38 mL, 2M, 64 mmol) at 0° C. This reaction was allowed to reach room temperature and stirred for 2 h. At this time, the reaction mixture was concentrated in vacuo. The solid, was run through a plug of silica, starting with 2% MeOH/CHCl$_3$ then adding 0.5% TEA and increasing the polarity to 5% MeOH and eluting. The product was concentrated in vacuo. To the solid (3.36 g, 4.47 mmol) was added DCM (45 mL) and DMF (20 mL). To this solution, was added Fmoc-His(Boc)-OH (2.24 g, 4.69 mmol), then HOBt (0.634 g, 4.64 mmol), then EDC.HCl (0.899 g, 4.69 mmol). This solution was allowed to stir for 8 h at which time the organic solution was washed with water (1×20 mL), then 1N HCl (3×20 mL), then saturated NaHCO$_3$ (3×20 mL), and finally H$_2$O (3×20 mL). The organic layer was dried over MgSO$_4$ and concentrated in vacuo to yield a white solid. Column chromatography (0-2% MeOH, CHCl$_3$) afforded the product: $^1$H NMR (500 MHz, d$_6$ DMSO) δ 8.30 (s, 2H), 8.18 (m, 1H), 8.09 (s, 1H), 8.04 (br s, 1H), 7.95 (br s, 1H), 7.87 (m, 2H), 7.64 (m, 2H), 7.55 (br m, 1H), 7.41-7.22 (m, 11H), 6.71 (br m, 2H), 5.00 (s, 2H), 4.35-4.16 (m, 7H), 3.60 (s, 3H), 2.98-2.82 (m, 9H), 1.70-1.45 (m, 16H), 1.44-1.28 (m, 35H); $^{13}$C NMR (125 MHz, de DMSO) δ 172.4, 171.7, 171.3, 156.1, 155.8, 155.5, 146.6, 143.7, 143.6, 140.7, 140.6, 139.5, 137.2, 136.6, 128.3, 127.7, 127.6, 127.0, 125.3, 125.2, 120.1, 120.0, 114.4, 85.0, 79.2, 77.3, 65.8, 65.1, 51.9, 51.7, 46.6, 31.8, 30.4, 29.3, 29.2, 29.0, 28.2, 27.3, 22.6, 22.5; ESMS (FAB) m/z calcd for C$_{63}$H$_{87}$N$_9$O$_{15}$ (M+H)$^+$ 1210.64, found 1210.57.

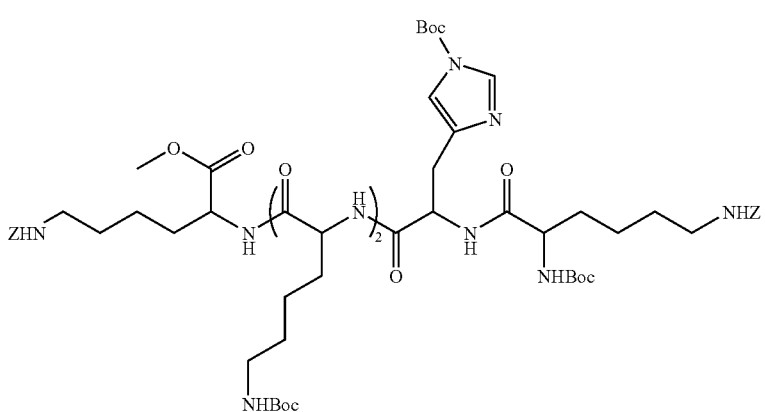

4

Synthesis of Boc-Lys(Z)His(Boc)-Lys(Boc)-Lys(Boc)-BocLys(Z):

To a solution of FmocHis(Boc)-Lys(Boc)-Lys(Boc)-BocLys(Z) (2.32 g, 1.92 mmol) in THF (40 mL), was added dimethyl amine (19.2 mL, 2M, 38.4 mmol) at 0° C. This reaction was allowed to reach room temperature and stirred for 2 h. At this time, the reaction mixture was concentrated in vacuo. The solid, was run through a plug of silica, starting with 2% MeOH/CHCl$_3$ then adding 0.5% TEA and increasing the polarity to 5% MeOH and eluting. The product was concentrated in vacuo. To the solid (0.880 g, 0.891 mmol) was added DCM (20 mL) and DMF (6 mL). To this solution, was added Boc-Lys(Z)—OH (0.4063 g, 1.06 mmol), then HOBt (0.144 g, 1.06 mmol), then EDC.HCl (0.205 g, 1.06 mmol). This solution was allowed to stir for 8 h at which time the organic solution was washed with water (1×10 mL), then 1N HCl (3×10 mL), then saturated NaHCO$_3$ (3×10 mL), and finally H$_2$O (3×10 mL). The organic layer was dried over MgSO$_4$ and concentrated in vacuo to yield a white solid. Column chromatography (0-2% MeOH, CHCl$_3$) afforded the product: $^1$H NMR (500 MHz, d$_6$ DMSO) δ 8.31 (s, 1H), 8.15 (br s, 1H), 8.05 (s, 1H), 7.97 (br m, 2H), 7.83 (br s, 1H), 7.40-7.15 (m, 13H), 6.90 (br s, 1H), 6.65 (br s, 2H), 5.00 (s, 4H), 4.52 (br s, 1H), 4.35-4.15 (m, 3H), 3.80 (br s, 1H), 3.60 (s, 3H), 3.05-2.75 (m, 10H), 1.72-1.40 (m, 18H), 1.39-1.12 (m, 46H); $^{13}$C NMR (125 MHz, d$_6$ DMSO) δ 172.4, 171.7, 171.1, 156.0, 155.5, 146.6, 138.9, 137.3, 136.5, 128.3, 127.7, 114.5, 85.1, 79.2, 78.2, 77.3, 65.1, 51.9, 51.7, 31.3, 30.4, 29.1, 29.0, 28.2, 28.1, 27.3, 22.7, 22.5; ESMS (FAB) m/z calcd for C$_{67}$H$_{103}$N$_{11}$O$_{18}$ (M+H)$^+$ 1350.75, found 1351.6.

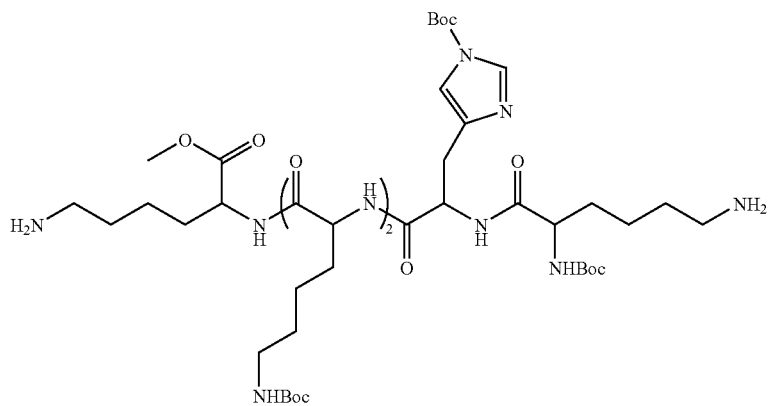

5

Synthesis of (Boc)Lys(Z)-His(Boc)-Lys(Boc)-Lys(Boc)-Lys-OMe:

To a solution of (Boc)Lys(Z)-His(Boc)-Lys(Boc)-Lys-OMe (0.88 g) in MeOH (50 mL) and chloroform (10 mL), was added Pd/C (0.20 g). This solution was flushed with H$_2$ for 30 min. and then fitted with a H$_2$ balloon. The reaction was allowed to proceed for 8 h at which time the mixture was filtered through celite, and conc. in vacuo to yield pure product: $^1$H NMR (500 MHz, d$_6$ DMSO) δ 8.32 (br s, 1H), 8.05 (s, 2H), 7.95 (br s, 2H), 7.28 (s, 1H), 6.95 (br s, 1H), 6.78 (br s, 2H), 4.55 (br s, 2H), 4.35-4.15 (br m, 4H), 3.83 (br s, 2H), 3.61 (s, 3H), 2.95-2.80 (br s, 6H), 2.65-2.75 (br m, 4H), 1.72-1.39 (m, 19H), 1.38-1.15 (m, 36H); $^{13}$C NMR (125 MHz, d$_6$ DMSO) δ 172.3, 171.8, 171.2, 170.8, 155.5, 146.6, 138.8, 136.53, 134.0, 114.5, 85.13, 78.17, 77.3, 54.4, 52.5, 52.3, 51.8, 31.5, 31.0, 29.3, 29.2, 28.3, 28.1, 27.4, 27.0, 22.5, 22.4, 22.3; ESMS (FAB) m/z calcd for C$_{51}$H$_{91}$N$_{11}$O$_4$ (M+H)$^+$ 1082.68, found 1082.85.

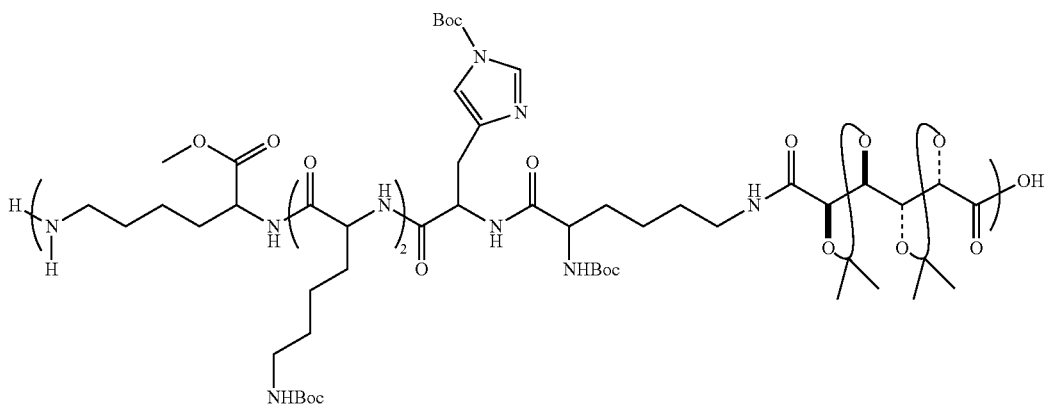

Poly 5

Synthesis of the Histidine Functionalized Polymer.

Compound 5 (0.280 g, 0.259 mmol) along with $Na_2CO_3$ (0.603 g) was stirred in 3 mL of $H_2O$ and 0.5 mL MeOH. To this vigorously stirring solution, was added a solution of galactoryl chloride (0.085 g, 0.259 mmol) in 2.0 mL $CCl_4$. This biphasic mixture was stirred for 30 min at room temperature. The precipitate was collected by filtration and washed with water to yield a white solid. $M_n$=2000 g/mol.

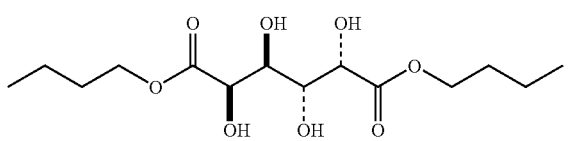

6

Synthesis of 2:3-4:5-Tetrahydroxy-Galactaric Acid Dibutyl Ester (6).

A mixture of galactaric acid (30.0 g, 0.143 mol), 1-butanol (220 mL), and conc. $H_2SO_4$ (6 mL) was heated to reflux for 24 h in a Soxhlet extractor containing 4 Å molecular sieves. The reaction mixture was allowed to cool to room temperature and filtered. The filter cake was washed with saturated $NaHCO_3$ (100 mL) and dried to yield pure diester (1, 32.2 g, 70%): $^1$H NMR (500 MHz, $d_6$ DMSO) δ 4.87 (d, J=9.88, 2H), 4.79 (dd, $J_1$=3.20, $J_2$=7.44, 2H), 4.29 (d, J=9.42, 2H), 4.07 (m, 4H), 3.77 (d, J=7.34, 2H), 1.58 (m, 4H), 1.32 (m, 4H), 0.88 (m, =6H); $^{13}$C NMR (125 MHz, $d_6$ DMSO) δ 174.6, 72.2, 71.1, 64.6, 31.2, 19.5, 14.5; HRMS m/z calcd for $C_{14}H_{26}O_8$ (M+Na)$^+$ 323.1706, found 323.1707. Anal. Calcd for $C_{14}H_{26}O_8$ C, 52.16; H, 8.13. Found: C, 52.15; H, 8.15.

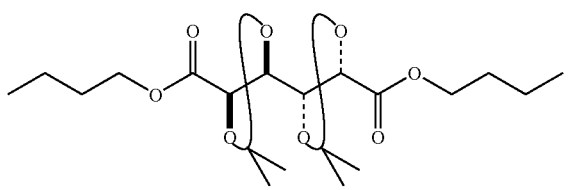

7

Synthesis of 2:3-4:5-Di-O-Isopropylidene Galactaric Acid Dibutyl Ester (7).

To a well stirred solution of 6 (10 g, 31 mmol,) in dry acetone (100 mL) was added concentrated $H_2SO_4$ (3.0 mL) and anhydrous $MgSO_4$ (5.0 g). This was stirred at room temperature for 24 h, at which time the reaction mixture was neutralized with $NaHCO_3$. The reaction mixture was then filtered. Solid product was precipitated from the filtrate by addition of water (100 mL). The precipitate was filtered and dried and recrystallized in ethanol to afford 7 (8 g, 64%) as a white crystalline solid. $^1$H NMR (500 MHz, $CDCl_3$) δ 4.60-4.57 (m, 1H), 4.48-4.45 (m, 1H), 4.20 (t, J=6.7, 2H), 1.68-1.62 (m, 2H), 1.50 (s, 3H), 1.40 (s, 3H), 1.41-1.37 (m, 2H), 0.93 (t, J=7.4, 3H); $^{13}$C NMR (125 MHz, $CDCl_3$) δ 171.0, 12.3, 79.2, 76.0, 65.5, 30.5, 27.0, 26.0, 19.0, 13.6; HRMS m/z calcd for $C_{20}H_{34}O_8$ (M+Na)$^+$ 403.2332, found 403.2332. Anal. Calcd for $C_{20}H_{34}O_8$ C, 59.68; H, 8.5. Found: C, 60.02; H, 8.35.

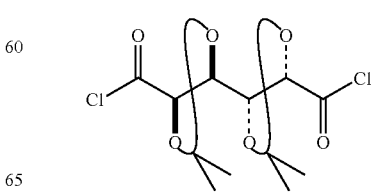

8

Synthesis of 2:3-4:5-Di-O-Isopropylidene Galactaric Acid (8).

2,3-4,5-di-O-isopropylidene ester 7 (2.66 g, 5.38 mmol) was hydrolyzed by heating to reflux in 5 mL aqueous NaOH (0.84 g, 21.6 mmol) for 12 h. The reaction solution was allowed to cool to room temperature and 12 mL of 2 N HCl was then added. This solution was cooled in an ice bath. Upon cooling a white precipitate formed. The solid was filtered and recrystallized from ethanol to afford 8 (1.07 g, 68%): $^1$H NMR (500 MHz, $d_6$ DMSO) δ 13.17 (s, 2H), 4.45 (m, 2H), 4.38 (m, 2H), 1.38 (s, 6H), 1.33 (s, 6H); $^{13}$C NMR (125 MHz, $d_6$ DMSO) δ 172.2, 111.0, 78.5, 74.9, 26.8, 25.8; Anal. Calcd for $C_{12}H_{18}O_8$: C, 49.65; H, 6.25. Found: C, 49.49; H, 5.98.

9

Synthesis of 2:3-4:5-Di-O-Isopropylidene Galactoryl Chloride (9).

To a suspension of acid 8 (0.5 g, 1.72 mmol) in 20 mL CH$_2$Cl$_2$ (DCM) was added freshly distilled thionyl chloride (0.5 mL, 6.38 mmol). After 2 h one drop of DMF was added to this suspension. The reaction mixture was stirred for 12 h at room temperature until a clear solution resulted. The mixture was filtered though a 0.2 μm PTFE filter and concentrated in vacuo providing the diacid chloride 9 (0.53 g, 94%) as a colorless solid: $^1$H NMR (500 MHz, de DMSO) δ 4.82 (m, 2H), 4.58 (m, 2H), 1.53 (s, 6H), 1.44 (s, 6H); $^{13}$C NMR (125 MHz, de DMSO) δ 173.9, 114.7, 83.6, 27.5, 26.3; Anal. Calcd for C$_{12}$H$_{16}$C$_{12}$O$_6$: C, 44.05; H, 4.93. Found: C, 43.75; H, 5.07.

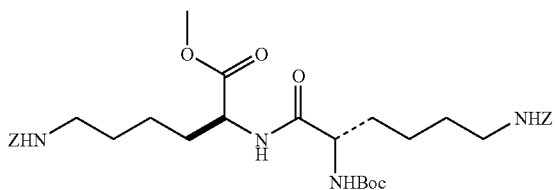

10

Synthesis of Boc-Lys(Z)-Lys(Z)-OMe (10).

To an ice cold cool solution of Z-Lys-OMe·HCl (4.347 g, 13.14 mmol) in dry DCM (75 mL) was added diisopropyl ethyl amine (2.29 mL, 13.14 mmol) followed by Z-Lys(Boc)-OH (5.00 g, 13.14 mmol), HOBt (1.776 g, 13.14 mmol) and EDC.HCl (2.519 g, 13.14 mmol). The reaction mixture was stirred for 8 h at room temperature. The organic solution was then washed with 1 N HCl (3×30 mL) saturated NaHCO$_3$ (3×30 mL) and water (3×30 mL). The organic layer was dried over MgSO$_4$ and concentrated in vacuo to yield a white solid. The crude product was purified by crystallization in 30% EtOAc/hexane. Compound 10 was isolated as a colorless solid (7.123 g, 82.6%): $^1$H NMR (500 MHz, CDCl$_3$) δ 7.36-7.26 (m, 10H), 6.77 (br s, 1H), 5.29 (br s, 1H), 5.12-5.06 (m, 5H), 4.54 (m, 1H), 4.11 (m, 1H), 3.68 (s, 3H), 3.18-3.11 (m, 4H), 1.80-1.45 (m, 8H), 1.42 (s, 9H), 1.31-1.36 (m, 4H); $^{13}$C NMR (125 MHz, CDCl$_3$) δ 172.5, 156.5, 155.8, 136.5, 136.4, 128.4, 128.3, 128.1 (2), 128.0 (2), 127.9 (2), 127.7 (2), 79.9, 66.5, 66.4, 53.9, 52.2, 51.9, 40.3 (2), 31.9, 31.4, 29.2, 29.0, 28.2 (3), 22.3, 22.1, Anal. Calcd for C$_{14}$H$_{26}$; C, 62.18; H, 7.37. Found C, 62.33; H, 7.44.

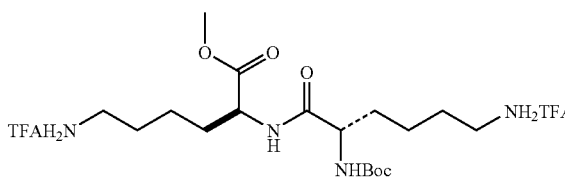

11

Synthesis of Boc-Lys-Lys-OMe (11).

Dilysine 10 (7.43 g, 0.0113 mol) was dissolved in MeOH (100 mL). After being purged with nitrogen, 10% Pd/C (0.30 g) was added. The flask was then purged with hydrogen and the reaction mixture was stirred for overnight. The Pd/C was removed by filtration through a pad of celite. Trifluoroacetic acid (TFA, 1.8 mL, 0.023 mol) was added into the filtrate and then the solvent was removed in vacuo to give viscous oil. A white gluey substance was obtained by triturating with 20 mL diethyl ether. The resulting substance was dried in vacuo to give the glassy solid product 11 (6.4 g, 92%): $^1$H NMR (500 MHz, d$_6$ DMSO) δ 8.19 (d, J=7.5, 1 H), 7.90 (br s, 6H), 6.82 (d, J=8.0, 1 H), 4.23 (m, 1H), 3.91 (m, 1H), 3.61 (s, 3H), 2.75 (m, 4H), 1.36-1.61 (m, 21H); $^{13}$C NMR (125 MHz, d$_6$ DMSO) δ 172.4 (2), 158.4 (q, 2), 155.3, 117.2 (q, 2), 78.0, 53.9, 51.6, 38.7, 38.6, 31.2, 30.3, 28.1 (3), 26.7, 26.5, 22.3, 22.2; HRMS (FAB) m/z calcd for C$_{22}$H$_{38}$F$_6$N$_4$O$_9$ (M+H)$^+$ 389.2764, found 389.2767.

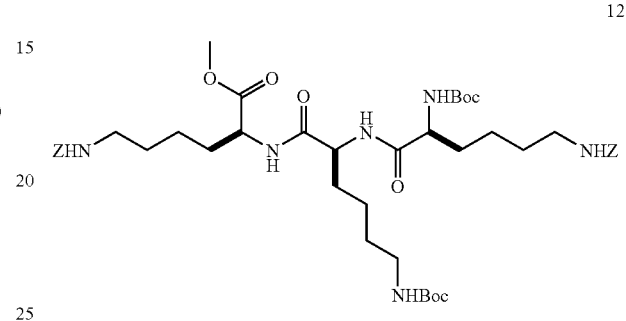

12

Synthesis of Boc-Lys(Z)-Lys(Boc)-Lys(Z)-OMe (12).

To a solution of 1 (2.405 g, 3.23 mmol) in THF (50 mL), was added dimethyl amine (16 mL, 2M, 32.3 mmol) at 0° C. This reaction was allowed to reach room temperature and stirred for 2 h. At this time, the reaction mixture was concentrated in vacuo. To the yellowish solid was added DCM (50 mL) and DMF (10 mL). To this solution, was added Boc-Lys (Z)—OH (1.23 g, 3.23 mmol), then HOBt (0.458 g), then EDC.HCl (0.650 g, 15.1 mmol). This solution was allowed to stir for 8 h at which time the organic solution was washed with 1N HCl (3×15 mL), then saturated NaHCO$_3$ (3×15 mL), and finally H$_2$O (3×15 mL). The organic layer was dried over MgSO$_4$ and concentrated in vacuo to yield a white solid. Column chromatography (2% MeOH, CHCl$_3$) afforded the product 12 (1.86 g, 65% yield): $^1$H NMR (500 MHz, CDCl$_3$) δ 7.74 (d, J=7.55, 2H), 7.58 (d, J=7.35, 2H), 7.38-7.25 (m, 15H), 7.00 (br d, 2H), 5.50 (br, s, 1H), 5.16-5.09 (m, 5H), 4.55 (br s, 1H), 4.36 (m, 3H), 4.25-4.10 (m, 2H), 3.61 (s, 3H), 3.16-3.10 (m, 6H), 1.81-1.39 (m, 23H); $^{13}$C NMR (125 MHz, CDCl$_3$) δ 172.7, 172.2, 156.8, 156.5, 156.2, 143.9, 143.8, 141.4, 141.3, 136.7, 128.5, 128.3, 128.1, 127.8, 125.2 (2), 120.1, 79.9, 67.2, 54.7, 53.6, 52.5, 50.2, 47.2, 40.3, 32.4, 31.4, 29.6, 29.3, 28.6 (3), 22.4; HRMS (FAB) m/z calcd for C$_{45}$H$_{68}$N$_6$O$_{12}$ (M+H)$^+$ 885.4974, found 885.4977.

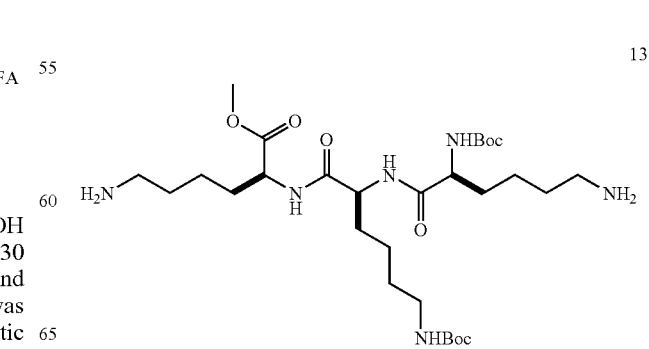

13

Synthesis of Boc-Lys-Lys(Boc)-Lys-OMe (13).

To a solution of 12 (0.88 g, 0.99 mmol) in MeOH (25 mL) and DCM (25 mL), was added Pd/C (0.20 g). This solution was flushed with $H_2$ for 30 min. and then fitted with an $H_2$ balloon. The reaction was allowed to proceed for 8 h at which time the mixture was filtered through celite, and conc. in vacuo to yield pure clear product 13 (0.622 g, quantitative): $^1$H NMR (500 MHz, $d_6$ DMSO) δ 8.42 (br s, 1H), 8.16 (br s, 4H), 7.92 (br s, 1H), 6.92 (br s, 1H), 6.74 (br s, 1H), 4.27 (br s, 1H), 4.20 (br s, 1H), 3.89 (br s, 1H), 3.62 (s, 3H), 3.46 (br s, 3H), 2.87-2.73 (m, 5H), 2.52 (s, 1H), 1.80-1.45 (br s, 10H), 1.45-1.15 (m, 22H); $^{13}$C NMR (125 MHz, $d_6$ DMSO) δ 173.2, 172.8, 156.4, 156.2, 78.94, 78.19, 54.91, 53.1, 52.7, 52.6, 39.3, 39.2, 32.8, 32.0, 30.9, 29.1, 29.1, 27.3, 27.2, 23.2, 23.1. HRMS (FAB) m/z calcd for $C_{29}H_{56}N_6O_8$ (M+H)$^+$ 617.4238, found 617.4236.

was dried over $MgSO_4$ and concentrated in vacuo to yield a white solid. Column chromatography (2% MeOH, $CHCl_3$) afforded the product 14, (3.42 g, 63% yield): $^1$H NMR (500 MHz, $CDCl_3$) δ 7.74 (d, J=7.55, 2H), 7.58 (d, J=7.35, 2H), 7.38-7.25 (m, 15H), 7.00 (br d, 2H), 5.50 (br, s, 1H), 5.16-5.09 (m, 5H), 4.55 (br s, 1H), 4.36 (m, 3H), 4.25-4.10 (m, 2H), 3.61 (s, 3H), 3.16-3.10 (m, 6H), 1.81-1.39 (m, 23H); $^{13}$C NMR (125 MHz, $CDCl_3$) δ 173.1, 172.0, 157.1, 156.74, 156.6, 144.2, 141.7, 137.2, 128.9, 128.6, 128.5, 128.3, 128.2, 127.6, 125.6, 125.5, 120.4, 79.5, 67.5, 66.9, 55.2, 52.8, 52.5, 47.5, 40.8, 40.4, 40.3, 32.6, 31.8, 29.9, 29.6, 28.9, 28.8, 23.0, 22.8; HRMS (FAB) m/z calcd for $C_{52}H_{72}N_6O_8$ (M+Na)$^+$ 995.5106, found 995.5132.

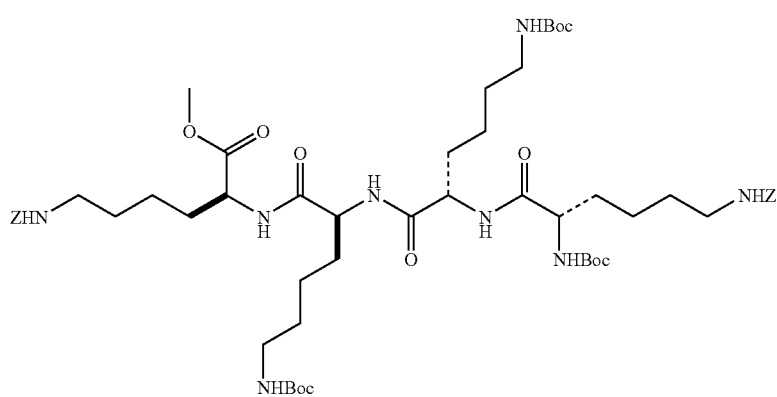

15

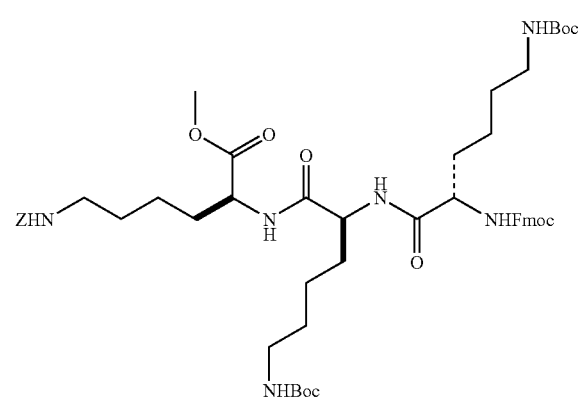

14

Synthesis of Fmoc-Lys(Boc)-Lys(Boc)-Lys(Z)-OMe (14).

To a solution of 1 (4.16 g, 5.58 mmol) in THF (55 mL), was added dimethyl amine (28 mL, 2M, 56.0 mmol) at 0° C. This reaction was allowed to reach room temperature and stirred for 2 h. At this time, the reaction mixture was concentrated in vacuo. To the yellowish solid, was added DCM (75 mL) and DMF (25 mL). To this solution, was added Fmoc-Lys(Boc)-OH (2.18 g, 4.64 mmol), then HOBt (0.627 g, 4.64 mmol), then EDC.HCl (0.890 g, 4.64 mmol). This solution was allowed to stir for 8 h at which time the organic solution was washed with 1N HCl (3×15 mL), then saturated $NaHCO_3$ (3×15 mL), and finally $H_2O$ (3×15 mL). The organic layer Synthesis of Boc-Lys(Z)-Lys(Boc)-Lys(Boc)-Lys(Z)-OMe (15).

To a solution of 14 (1.48 g, 1.52 mmol) in THF (30 mL), was added dimethyl amine (15.2 mL, 2M in THF, 30.4 mmol) at 0° C. This reaction was allowed to reach room temperature and stirred for 2 h. At this time, the reaction mixture was concentrated in vacuo. To the yellowish solid was added DCM (30 mL) and DMF (5 mL). To this solution, was added Boc-Lys(Z)—OH (0.608 g, 1.60 mmol), then HOBt (0.216 g, 1.60 mmol), then EDC.HCl (0.3063 g, 1.60 mmol). This solution was allowed to stir for 8 h at which time the organic solution was washed with 1N HCl (3×15 mL), then saturated $NaHCO_3$ (3×15 mL), and finally $H_2O$ (3×15 mL). The organic layer was dried over $MgSO_4$ and concentrated in vacuo to yield a white solid. Column chromatography (2% MeOH, $CHCl_3$) afforded the product 15 (1.0 g, 59% yield): $^1$H NMR (500 MHz, $CDCl_3$) δ 8.15 (br s, 1H), 8.03 (br s, 1H), 7.88 (br s, 1H), 7.45-7.28 (m, 10H), 7.12 (br s, 1H), 6.65 (br s, 1H), 5.08 (s, 1H), 4.45-4.35 (m, 3H), 4.05 (br s, 1H), 3.67 (s, 3H), 3.11 (br s, 1H), 3.01 (br s, 1H), 1.90-1.60 (m, 8H), 1.60-1.38 (m, 44); $^{13}$C NMR (125 MHz, $CDCl_3$) δ 173.3, 173.2, 172.7, 172.3, 157.2, 156.6, 138.4, 129.0, 128.4, 79.0, 78.1, 66.0, 55.7, 53.8, 53.4, 53.0, 52.2, 41.1, 40.9, 40.8, 32.7, 32.5, 31.6, 29.8, 29.6, 28.6, 23.7, 23.5; ESMS (FAB) m/z calcd for $C_{66}H_{88}N_8O_{15}$ (M+H)$^+$ 1113.65, found 1113.52.

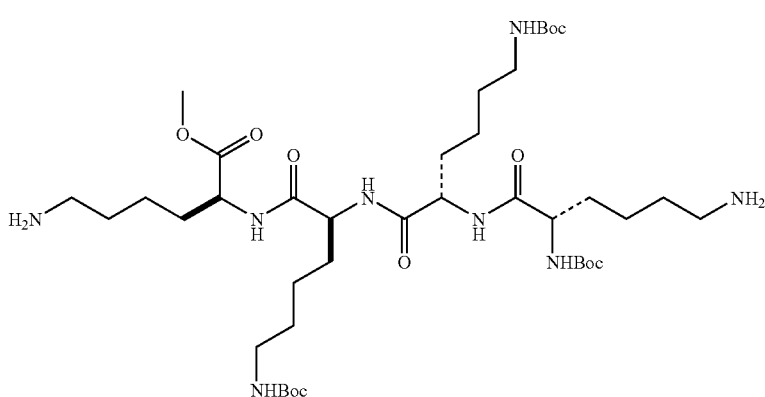

16

Synthesis of Boc-Lys-Lys(Boc)-Lys(Boc)-Lys-OMe (16).

To a solution of 15 (1.0 g, 0.89 mmol) in MeOH (25 mL) and DCM (25 mL), was added Pd/C (0.20 g). This solution was flushed with $H_2$ for 30 min. and then fitted with a $H_2$ balloon. The reaction was allowed to proceed for 8 h at which time the mixture was filtered through celite, and conc. in vacuo to yield pure product (0.75 g, 0.89 mmol): $^1$H NMR (500 MHz, $CDCl_3$) δ 8.04 (br s, 1H), 6.70 (br s, 3H), 4.32 (br s, 4H), 3.69 (s, 3H), 3.05 (m, 8H), 1.85-1.65 (m, 8H), 1.65-1.40 (m, 28); $^{13}$C NMR (125 MHz, $CDCl_3$) δ 173.2, 172.9, 156.7, 78.9, 78.04, 52.2, 40.8, 40.1, 34.9, 34.8, 32.0, 31.1, 30.6, 28.6, 28.5, 23.6, 23.2, 23.1; HRMS (FAB) m/z calcd for $C_{40}H_{76}N_8O_{11}$ (M+H)$^+$ 845.5712, found 845.5699.

B. Polymer Synthesis

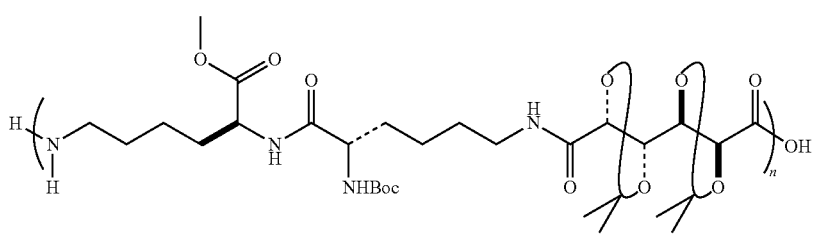

17

Synthesis of the Dilysine/Carbohydrate Copolymer (17).

Dilysine 11 (1.7085 g, 2.77 mmol) along with $Na_2CO_3$ (0.785 g, 7.4 mmol) was stirred in 60 mL of $H_2O$ cooled at 0° C. To this vigorously stirring solution, was added a solution of galactoryl chloride 9 (0.9066 g, 2.77 mmol) in 25 mL $CCl_4$. This biphasic mixture was stirred for 5 min at 0 OC and 30 min at room temperature. The precipitate was collected by filtration and washed with water to yield a white solid (1.1 g): $^1$H NMR (500 MHz, $CD_3OD$) δ 8.25 (m, 1H), 7.94 (m, 2H), 4.56 (m, 2H), 4.38 (m, 2H), 4.32 (m, 1H), 3.95 (m, 1H), 3.62 (s, 3H), 3.12 (m, 4H), 1.74-1.33 (m, 45H); $^{13}$C NMR (125 MHz, $CDCl_3$) δ 172.6, 158.7, 110.9, 80.0, 78.8, 75.1, 54.0, 52.5, 38.7, 34.5, 33.5, 29.3, 29.0, 28.5, 26.9, 26.1, 22.9; $M_n$=15,000 g/mol, $M_w$=27,900 g/mol.

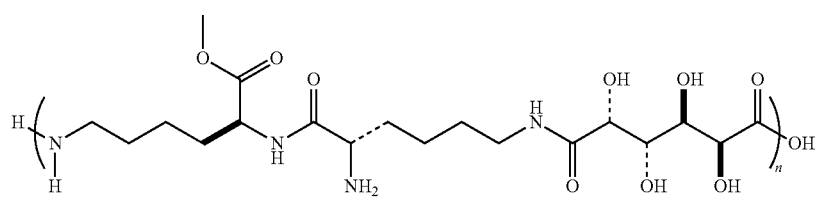

Poly 1

Deprotection of the Dilysine/Carbohydrate Polymer (Poly 1).

A solution of 30% TFA in THF (5.1 mL) was added to protected polymer 17 (0.123 g). After 1 h, water (1.2 mL) was added and the reaction was allowed to proceed for 5 h. At this time the solution was concentrated providing the deprotected polymer Poly 1 (quantitative): $^1$H NMR (500 MHz, CD$_3$OD) δ 4.65 (br d, 1H), 4.45-4.43 (m, 1H), 4.34-4.38 (m, 1H), 4.17 (br s, 1H), 3.95 (br s, 1H), 3.80 (s, 3H), 3.32-3.34 (m, 5H), 2.00-1.80 (m, 4H), 1.70-1.54 (m, 4H), 1.34-1.44 (m, 4H); $^{13}$C NMR (125 MHz, (CDCl$_3$) δ 183.5, 177.6, 177.5, 172.5, 73.2, 56.9, 55.6, 41.2, 33.1, 32.4, 30.6, 30.4, 30.3, 25.7, 24.8, 24.7, 23.8.

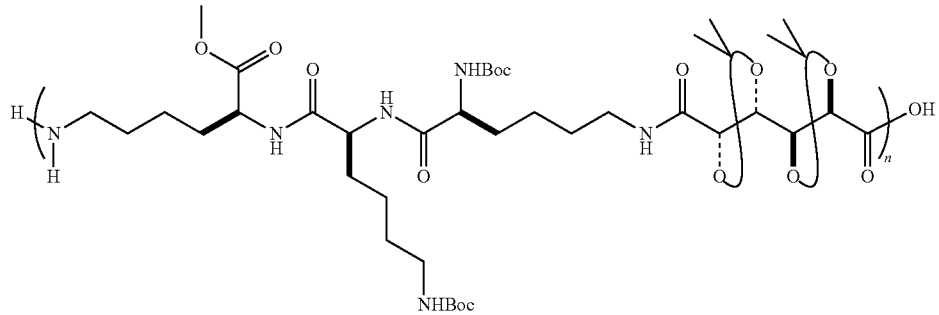

18

Synthesis of the Trilysine/Carbohydrate Polymer (18).

Compound 13 (0.296 g, 0.480 mmol) along with Na$_2$CO$_3$ (0.112 g) was stirred in 2.0 mL of H$_2$O cooled to 0° C. To this vigorously stirring solution, was added a solution of galactoryl chloride 9 (0.157 g, 0.480 mmol) in 4 mL CCl$_4$. This biphasic mixture was stirred for 5 min at 0° C. and 30 min at room temperature. The precipitate was collected by filtration and washed with water to yield a white solid (0.250 g): $^1$H NMR (500 MHz, CD$_3$OD) δ 8.25 (m, 1H), 7.94 (m, 2H), 4.56 (m, 2H), 4.38 (m, 2H), 4.32 (m, 1H), 3.95 (m, 1H), 3.62 (s, 3H), 3.12 (m, 4H), 1.74-1.33 (m, 45H); $^{13}$C NMR 125 MHz, (CDCl$_3$) δ 173.0 (m), 156.63 (m), 111.39 (m), 80.3, 79.39, 75.39, 52.8 (m), 40.6, 39.0, 31.7, 29.8, 28.79-26.4 (m), 22.91 (m); $M_n$=9085 g/mol, $M_w$=26686 g/mol.

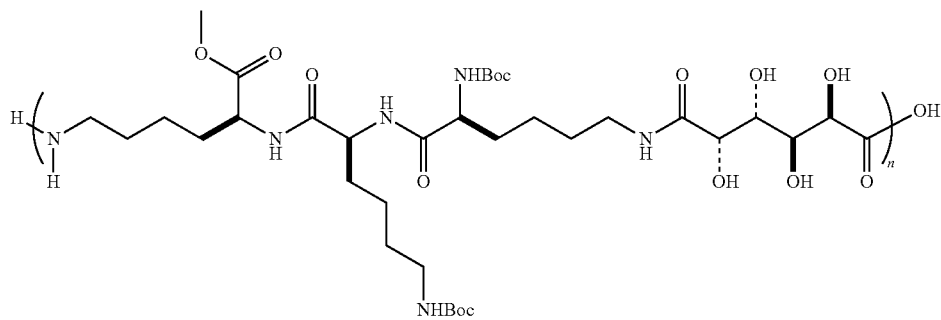

Poly 2

Deprotection of the Trilysine/Carbohydrate Polymer (Poly 2).

A solution of 30% TFA in THF (5.0 mL) was added to protected polymer 18 (0.105 g). After 1 h, water (1.0 mL) was added and the reaction was allowed to proceed for 5 h. At this time the solution was concentrated providing the deprotected polymer (Poly 2, quantitative): $^1$H NMR (500 MHz, CD$_3$OD) δ 4.625 (br s, 5H), 4.41 (br s, 4H), 4.05 (s, 1H), 3.95 (s, 1H), 3.74 (s, 3H), 2.98 (m, 3), 1.85-1.61 (m, 22H); $^{13}$C NMR 125 MHz, (CDCl$_3$) δ 173.2, 162.5-161.7 (m), 120.73, 118.4, 116.1, 113.7, 71.5-71.2 (m), 55.5-51.9 (m), 39.5, 38.5-35.4, 31.3 28.9, 27.1, 23.1, 22.6.

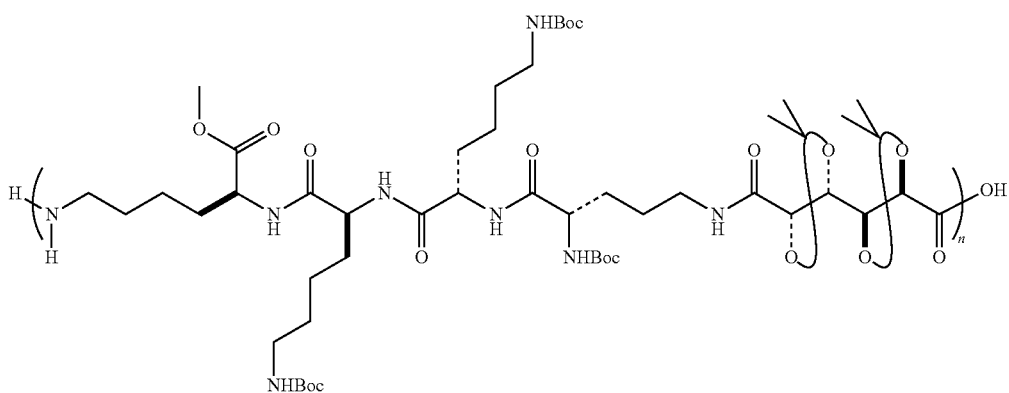

19

Synthesis of the Tetralysine/Carbohydrate Polymer (19).

Compound 16 (0.349 g, 0.413 mmol) along with Na$_2$CO$_3$ (0.0963) was stirred in 3 mL of H$_2$O cooled to 0° C. To this vigorously stirring solution, was added a solution of galactoryl chloride 9 (0.135 g, 0.413 mmol) in 3.5 mL CCl$_4$. This biphasic mixture was stirred for 5 min at 0 OC and 30 min at room temperature. The precipitate was collected by filtration and washed with water to yield a white solid (19, 0.380 g): $^1$H NMR (500 MHz, CDCl$_3$) δ 4.51 (m, 6H), 3.74 (s, 3H), 3.32-3.05 (m, 9H), 2.00-1.62 (br s, 10H), 1.30-1.62 (br s, 62H); $^{13}$C NMR (125 MHz, (CDCl$_3$) δ 174-170 (m), 157-155 (m), 110, 79-74 (m), 54-51 (m), 40-38 (m), 31-22 (m); M$_n$=13213 g/mol, M$_w$=47918 g/mol.

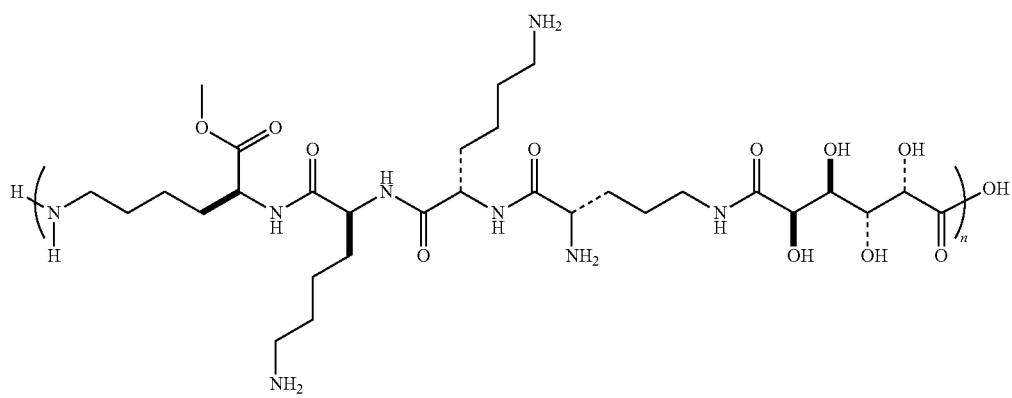

Poly 3

Synthesis of Deprotected Tetralysine Polymer (Poly 3).

A solution of 30% TFA in THF (1.7 mL) was added to protected polymer 19 (0.050 g). After 1 h, water (0.4 mL) was added and the reaction was allowed to proceed for 5 h. At this time the solution was concentrated providing the deprotected polymer (Poly 3, quantitative): $^1$H NMR (500 MHz, CD$_3$OD) δ 4.40 (m, 4H), 4.05 (m, 2H), 3.73 (s, 3H), 3.36 (s, 3H, with solvent peak), 2.97 (br s, 5H), 1.85-1.41 (m, 22H); $^{13}$C NMR (125 MHz, (CDCl$_3$) δ 173-169 (m), 164-160 (m), 71-67 (m), 54-51 (m), 40-39 (m), 31-21 (m).

Alternative Structures for Carbohydrate-Peptide Copolymers

Another alternative route to form saccharide-peptide copolymers is to use acrylate and primary amine based monomers to create polymers via Michael addition reactions as shown in Scheme XII below:

Scheme XII
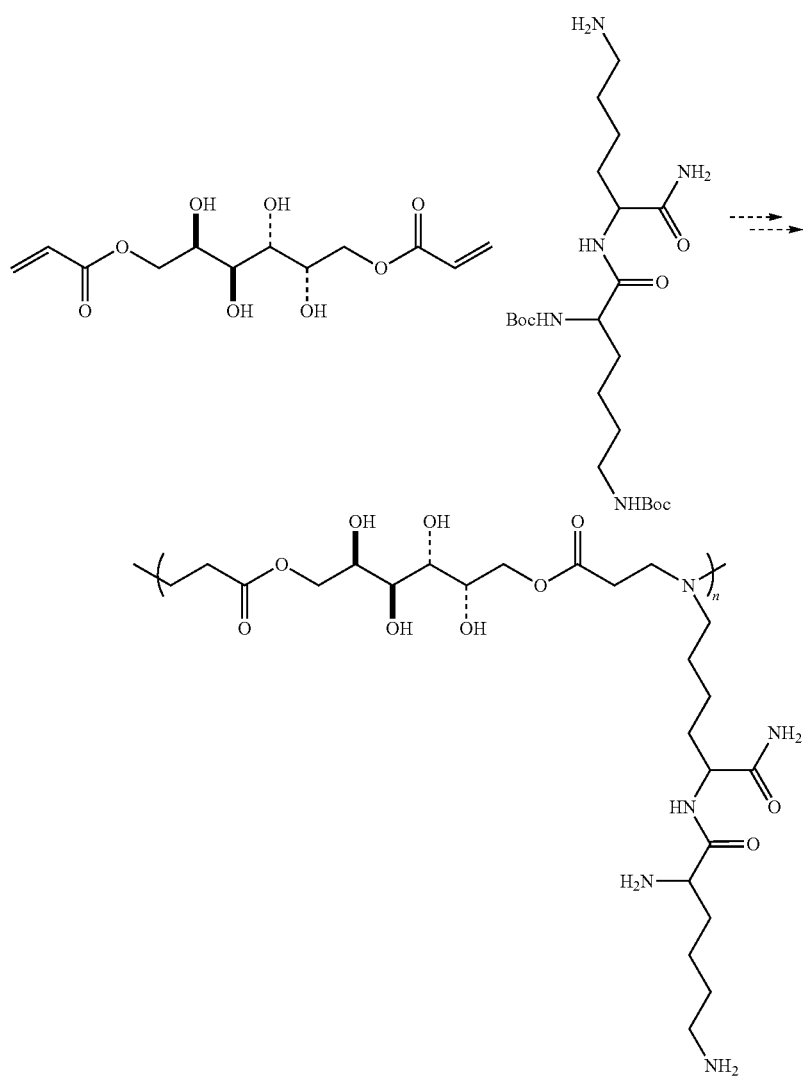
A model reaction with simpler monomers was tested for the feasibility of this route. The synthesis of the test acrylate monomer and polymer is shown in Scheme XIII below
Scheme XIII
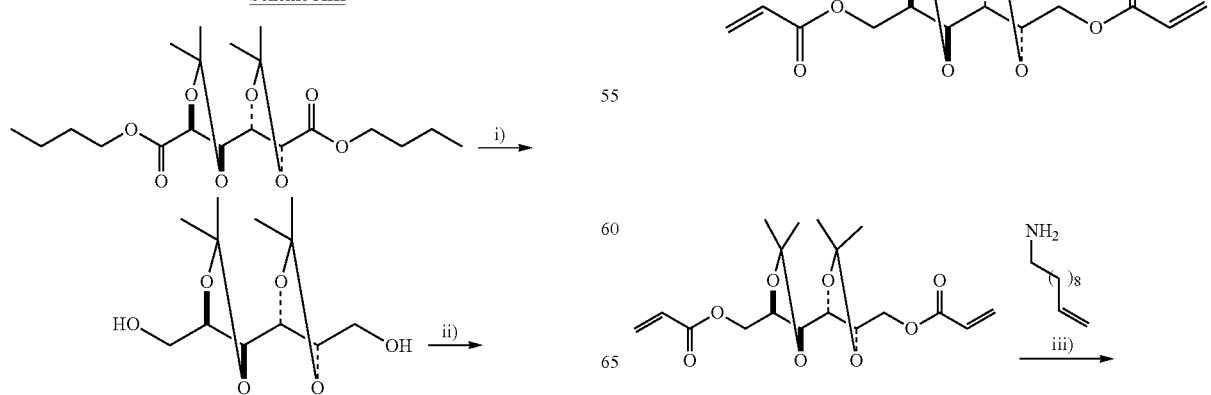

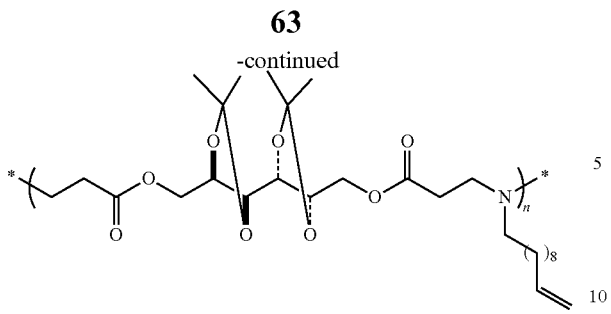

Reaction Conditions:
I) 4 eq. LAH, Et₂O, 4 h (Yield 72.1%)
ii) 4 eq. Acryloyl chloride, 4 eq. DIPEA, DCM, 0.5 h (Yield 60%)
iii) 1 eq. 22, 1 eq. 23, 1M in DCM A polymer was obtained from the model reaction. Following the same strategy, the following syntheses was contemplated by the inventor to make a new biomaterial as shown in Scheme XIV below:

This solution became brown and was allowed to stir for 45 minutes at which time H₂O (15 mL) was added. The product was extracted with Et₂O (100 mL) then separated and dried over MgSO₄. Column chromatography in 20% Et₂O/Hexane afforded the product (60% yield).

Scheme XIV

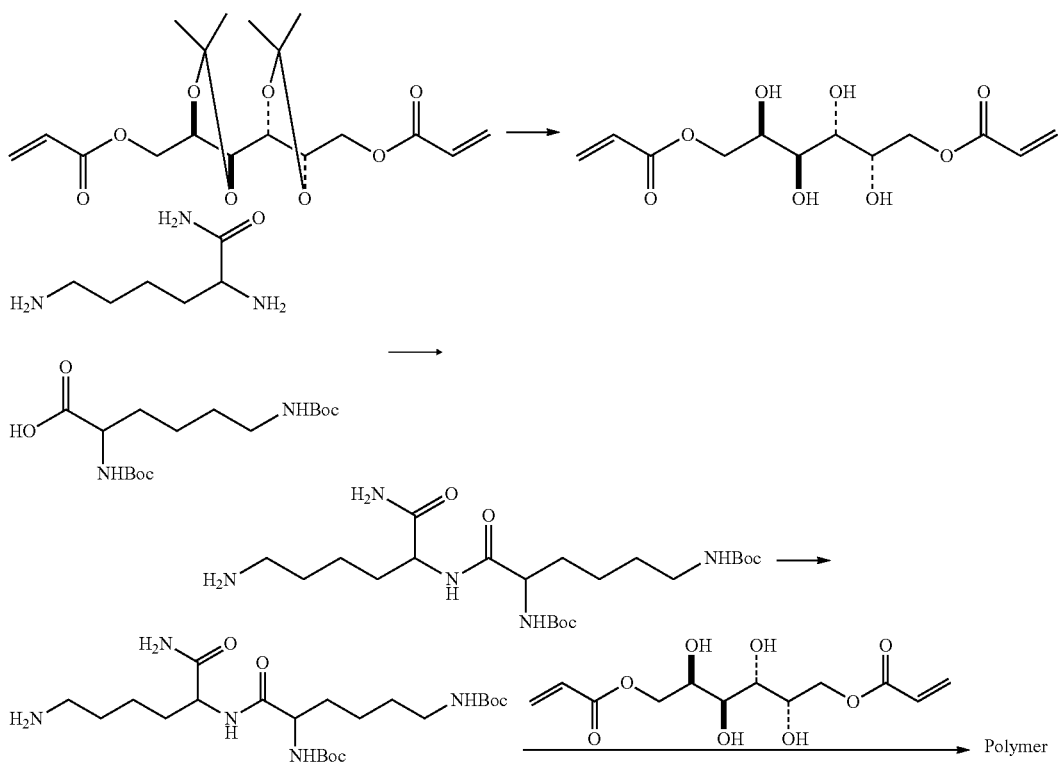

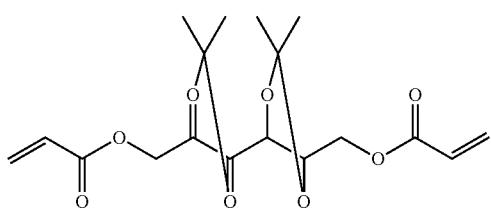

Synthesis of the Diacrylate Sugar Monomer:
To a stirred solution of the diacetinide protected sugar diol (0.50 g, 1.91 mmol) in DCM (19 mL) and DIPEA (4 mL) was added dropwise acryloyl chloride (0.93 mL, 11.44 mmol).

Polymerization of the Diacrylate Sugar Monomer and 11-Aminoundecene:
To a solution of 11-aminoundecene (0.1211 g, 0.7153 mmol) and DCM (0.25 mL), was added the diacrylate sugar monomer (0.2648 g, 0.7153 mmol). This was sealed under N₂ and stirred at 45° C. for 4 days to form the polymer.

Transfection Experiments

As examples, galactaro-dilysine, trilysine and tetralysine hybrid copolymers (Poly 1-3 respectively) were synthesized through interfacial polymerization of L-lysine derived monomers and a corresponding galactose-derived monomer. EMSA tests showed that these polymers effectively bound and retarded DNA at N/P ratios as low as 1.5. AFM imaging provided evidence for DNA compaction to a size suitable for gene transfection application, with 86.0-90.6% of the particles being below 200 nm in diameter. Luciferase assays showed that this class of polymers effectively transfects DNA under serum-free, chloroquine-assisted conditions. The transfection levels exceeded those of control experiments, which was likely due in part to the decrease in cytotoxicity of contemplated polymers. Cell viability tests showed that the copolymers presented herein have strikingly low cytotoxicity. It is contemplated that this decreased toxicity stems from lowering the continuous charge density on polymer backbone and the charge shielding effects by the hydrophilic carbohydrate spacers. Both factors decrease charge interactions with cell membrane, thus mitigating membrane disruption. This new class of carbohydrate-peptide copolymers may be further optimized to improve the transfection efficiency while maintaining biocompatibility, for example, by using alternative lengths of amino-acid residues, substituting different amino acid residues into the chain, as well as by lengthening or shortening the carbohydrate spacers.

Materials:

Reagents were used as received from Aldrich (Milwaukee, Wis.), with the exception of the amino acids which were purchased from NovaBiochem (San Diego, Calif.) and coupling reagents and additives [N-hydroxybenzotriazole (HOBt) and 1-ethyl-3-3'-dimethylaminopropylcarbodiimide.HCl (EDC.HCl)], which were purchased from GL Biochem (Shanghai, China). Monkey kidney fibroblasts (COS-7 cells) used in transfection studies were purchased from ATCC and incubated at 37° C., 5% $CO_2$ in MEM medium purchased from Sigma (Saint Louis, Miss.). Luciferase detection kits (reporter genes included), MTT kits, and pSV-β-gal plasmid DNA (6821 bp) were purchased from Promega (Madison, Wis.). All reactions were performed under a nitrogen atmosphere with the use of flame-dried glassware. All solvents used in water-sensitive reactions were dried and purified via distillation or from an alumina filtration system. Extraction solvents were commercial grade. Flash chromatography was performed using forced flow of indicated solvent systems over Fisher silica gel 60 (230-400 mesh).

General Considerations:

Any manipulations involving the use of living cells were performed using standard sterile techniques in a laminar flow hood. Gel Permeation Chromatography (GPC) was carried out using an Agilent 1100 Series GPC-SEC Analysis System along with a mixed bed Plgel Mixed-C column from Polymer Labs. The eluent was THF, and a flow rate of 0.5 mL/min was used. The calibration was performed using Aldrich polystyrenes as standards. $^1$H NMR spectra were acquired using 500 MHz Bruker instruments and $^{13}$C NMR with 125 MHz Bruker instruments. NMR chemical shifts were reported as δ values in ppm relative to TMS or deuterated solvent. Data are presented as follows: chemical shift, multiplicity (s=singlet, d=doublet, t=triplet, q=quartet, m=multiplet), coupling constant(s) in Hz and integrations. Multiplets are reported over the range (in ppm) in which they appear. Carbon NMR data were recorded relative to solvent signals. High resolution mass spectral (HRMS) data was obtained on a Micromass autospec spectrometer. Combustion analyses were performed by Atlantic Microlab (Norcross, Ga.).

Electrophoresis of Galactara-Lysine Polymer/DNA Complexes.

Carbohydrate-peptide copolymer/pSV-β-gal plasmid DNA complexes were formed at varying charge ratios in solutions of Hepes buffered saline (HBS, 20 mM Hepes, 150 mM NaCl, pH 7.4). The complexes were formed by mixing DNA solutions (10 μL, 0.1 μg/μL) with equal volumes of solutions containing the test polymers at varying primary amine to phosphate (N/P) ratios. The polymer/DNA solutions were allowed to stand at room temperature for 0.5 h, at which time 8 μL of the complex solution was removed and mixed with 2 μL of 6× loading dye. The complex/loading dye solutions were transferred to an agarose gel (0.6% w/v agarose, containing 0.5 μg/mL ethidium bromide) and the gel was developed (30 min, 90V). The location of the DNA in the gel was determined using a UV illuminator. The gel results are shown in FIG. 1.

Imaging Polyplexes by Atomic Force Microscopy (AFM):

Polyplexes were formulated as done in the electrophoresis experiments. After 30 minutes of incubation, 20 μL samples were taken from the polyplex solutions, and added to a fresh mica surface. The mica surface was then spun at 2000 RPM for 15 seconds. This was performed at 20 and 40 N/P for each polymer. A CP Research atomic force microscope equipped with 100 μm scanner from Park Scientific Instruments was used to carry out the polyplex visualization. ProScan software (version 1.6) was used for all of the data acquisition. The data are summarized below.

Cell Transfection Assays.

COS-7 cells were seeded at a density of 16,000 cells/well in a 24-well plate, 24 h prior to the start of the transfection study. Four hours prior to the addition of the polyplexes the cells were treated with chloroquine by adding 25 μL of a 2 mM solution of chloroquine in PBS buffer to each well. DNA/polymer complexes were prepared at the appropriate charge ratios by adding 50 μL of a polymer solution to 50 μL of a 0.7 μg/μL DNA solution and vortexing. The complexes were allowed to incubate for 30 min. The complex solution was then added to the cells and incubated for 5 hours under serum-free medium conditions. At this time, 50 μL of fetal calf serum was added to each well (making a total of 550 μL of medium) and the cells were incubated for 24 hours. The medium was then removed from the cells, which were then washed with PBS buffer (2=500 μL). To the cells was then added 250 μL lysis buffer and the cells were incubated for 10 min. At this time 50 μL of cell lysate and 50 μL of luciferase assay reagent were mixed and their luminescence was immediately read using a luminometer. The total protein content of the remaining lysate was then measured using a commercially available assay (n≥3). The transfection efficiency data obtained without and with chloroquine are summarized in FIG. 3.

Cell Proliferation Testing:

Cell proliferation testing was done with a non-radioactive MTT test. COS-7 cells were seeded at a density of 16,000 cells/well in a 24-well plate, 24 h prior to the start of the proliferation study. To these cells were added control and experimental polymers along with a blank solution (as a negative control) at the same concentration used in the transfection studies for each charge ratio under serum-free conditions. The cells were incubated for 5 hours and 50 μL of fetal calf serum was added to each well (making a total of 550 μL of medium). The cells were incubated for 24 hours, at which time 75 μL of a tetrazolium salt solution was added. After 4 h of incubation a stop solution was added and the cells were incubated an additional hour. The contents of each well were mixed and their absorbance was measured at 570 nm. The absorbance relative to control cells that were not treated with polymer was then calculated to give the % viable cells.

L-lysine-derived peptide residues were chosen to introduce cationic moieties from their α and ε primary amino groups. Although PLL is not the most efficient synthetic vector for gene delivery, it is one of the most studied synthetic vectors and has abundant data in literature for comparison, which makes it a good model peptide for demonstrating the currently presented carbohydrate-peptide design concept. Among other advantages, it was contemplated that introduction of carbohydrate spacers can reduce the cytotoxicity for PLL. Whereas PLL can effectively complex DNA and transport DNA into cells, it has relatively high cytotoxicity. Modifications of PLL with certain hydrophilic moieties have been shown to increase the solubility of the polyplexes and reduce its cytotoxicity. In the presently contemplated compounds, copolymerization of L-lysine-derived peptides with a carbohydrate-derived monomer introduced multiple polar hydroxyl groups is thought to give the polymers excellent water solubility. The carbohydrate spacers also lower the polymers' cationic charge density, which is expected to lower cytotoxicity. Condensation polymerization was employed between carbohydrate and peptide comonomers to construct the hybrid copolymers. For this purpose the required carbohydrate and peptide comonomers were prepared as discussed below.

Synthesis of Peptide and Carbohydrate Monomers and Copolymers.

Galactaric acid was chosen as an easily available carbohydrate derivative as the starting material for making the carbohydrate monomer. A simple four-step synthesis was employed for making diacid chloride monomer 4 as depicted in Scheme XV below:

Scheme XV

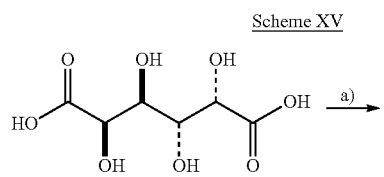

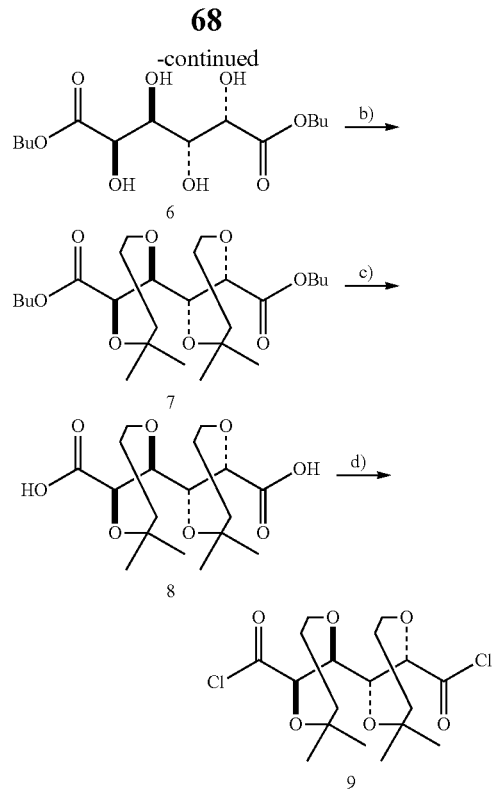

Esterification with 1-butanol, followed by acetonide protection of the hydroxyl functionalities afforded 2. Ester saponification was then carried out in basic medium to afford diacid 3. The diacid chloride monomer was then synthesized quantitatively using $SOCl_2$. For the synthesis of peptide monomers, simple solution phase peptide synthesis was employed as shown in Scheme XVI:

Scheme XVI

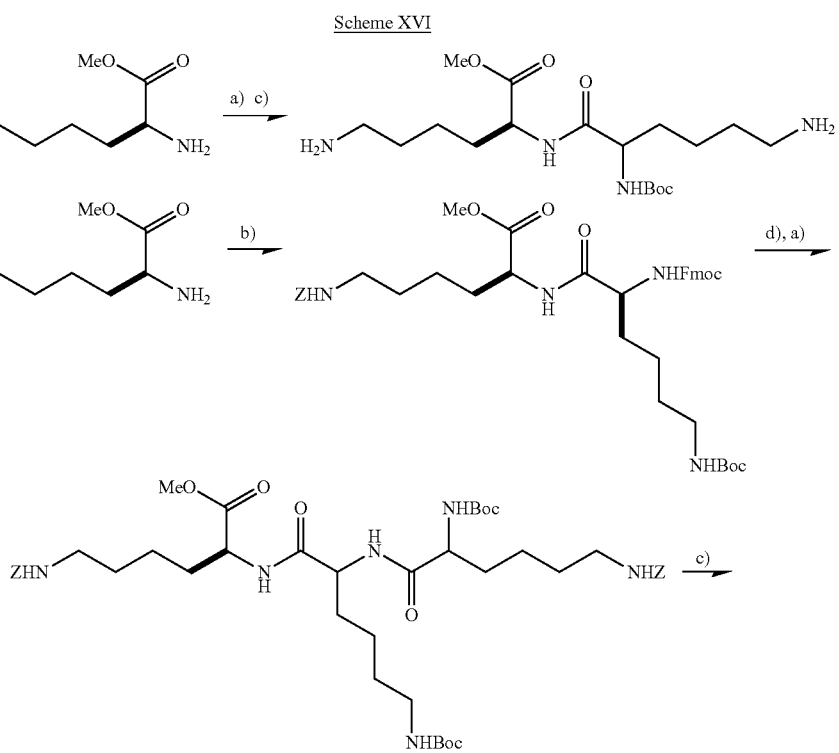

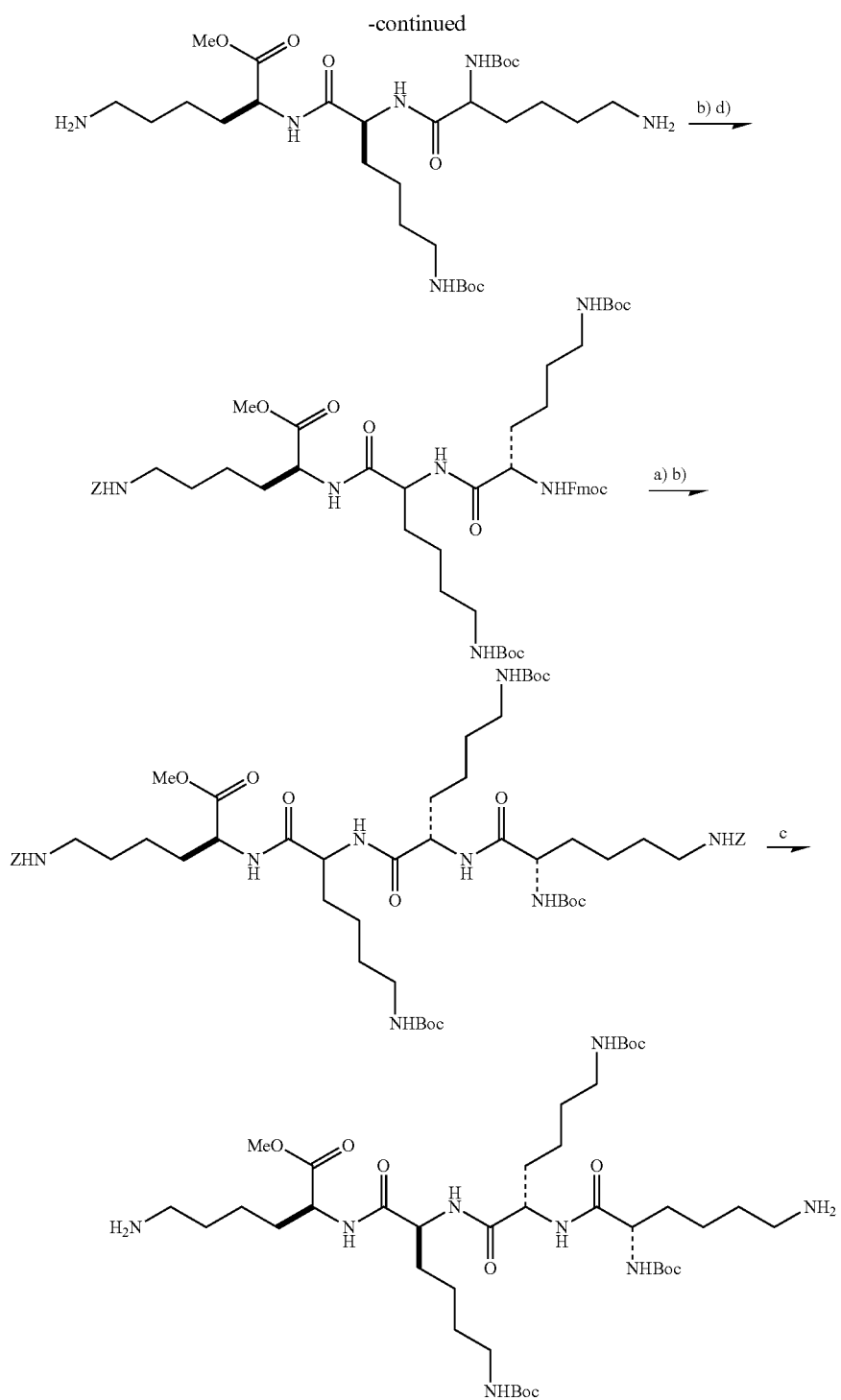

In each coupling reaction, EDC.HCl was used as a coupling agent in the presence of HOBt. Following each peptide coupling, 9-fluorenylmethyl carbamate (Fmoc) deprotection was performed using dimethyl amine in THF, which was then removed from the reaction mixture in vacuo and the next coupling reaction was carried out. The final step in each monomer synthesis was the quantitative removal of benzyloxycarbonyl (Z) protecting groups by standard hydrogenolysis. After testing various polymerization conditions, interfacial polymerization afforded the best results and was used for synthesizing each copolymer. Both $^1$H and $^{13}$C NMR spectra confirm the correct chemical structures of each polymer. The number-averaged molecular weights ($M_n$) of the three prepolymers (still Boc and acetonide protected) were measured to be 15,000, 9085, and 13,200 g/mol, respectively. A global deprotection of acetonide and t-butyl carbamate (Boc) protecting groups using TFA/H$_2$O/THF afforded the final copolymers, Poly 1-3 (Scheme XVII).

Scheme XVII
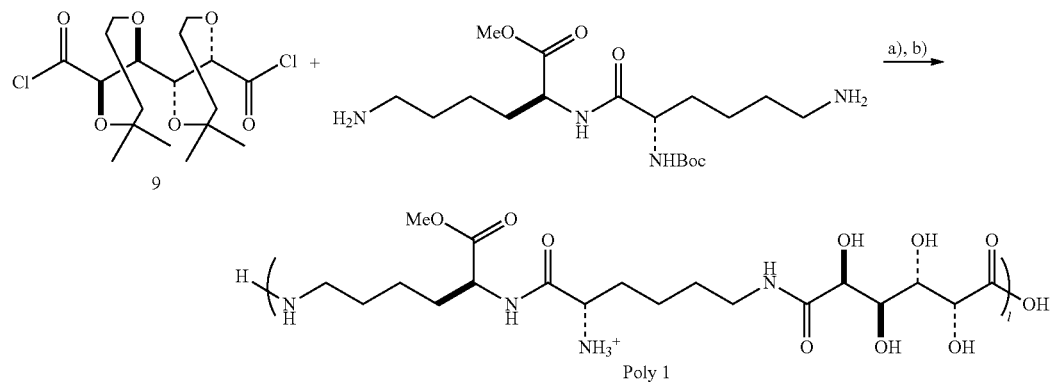
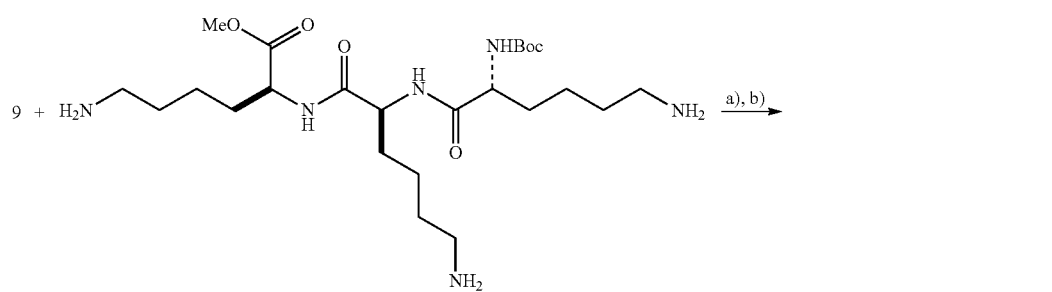
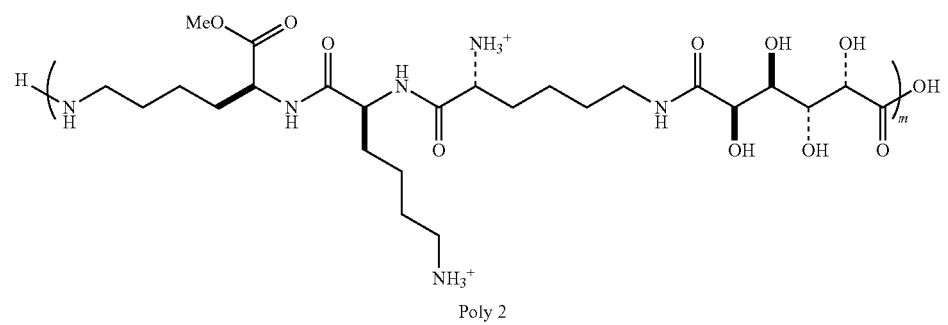
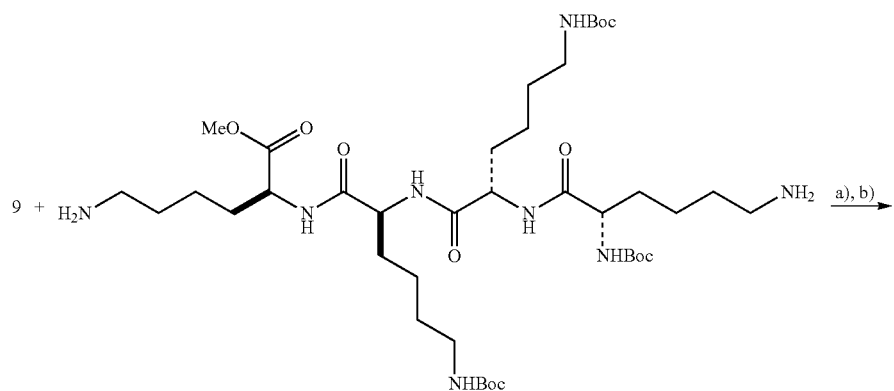

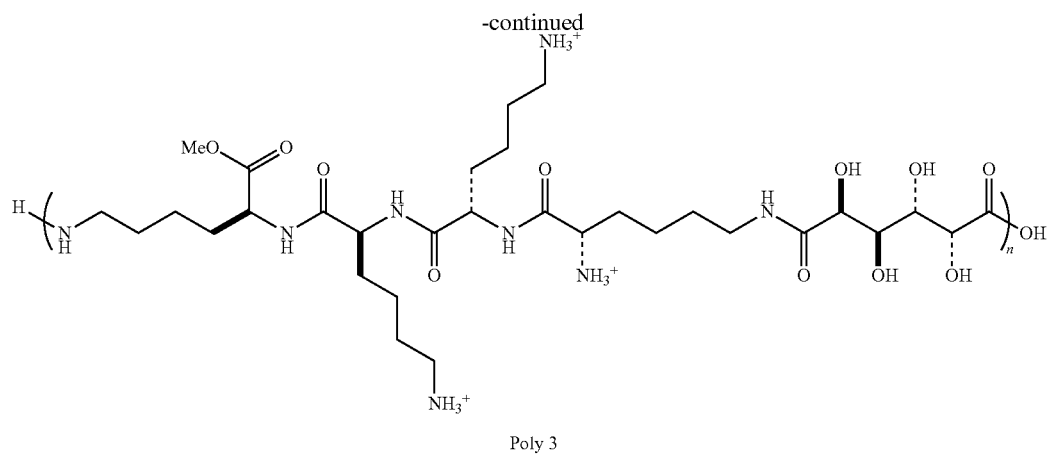

Poly 3

In Scheme 3 the free amines for Poly 1-3 are shown in their cationic form. The DNA complexation and gene transfection experiments with the hybrid copolymers were performed in aqueous solution buffered to a pH of 7.4, under which the amine groups would be protonated ($\alpha$-NH$_2$ pK$_a$~9, $\epsilon$-NH$_2$ pK$_a$~10.8).

In alternative route, a dilactone was first prepared by dehydration cyclization of a saccharic acid as exemplarily depicted below. Upon mixing a dilysine monomer with the dilactone in polar solvents such as methanol or water or mixed solvents, the terminal amino groups open the lactone rings and form hybrid copolymers. Other monomers carrying amino or other nucleophilic groups can be used to ring open dilactone for formation of hybrid copolymers with other structures as shown in Structure XI. More detailed experimental examples are described further below.

Dilactone Ring-Opening Polymerization

As illustrated previously in Scheme I, the inventor contemplated a more efficient route to make the disclosed polymers in which peptide portions and carbohydrate portions can be covalently coupled to each other using a ring-opening polymerization of a dilactone with a peptide having two terminal amino groups. To find out the good conditions for this direct ring-opening polymerization route, a model polymerization between ethylenediamine and glucaric acid 1,4:6,3-dilactone (A) was used to screen catalytic conditions in protic solvents that would form high polymers (Table 1). A series of catalysts that are known to catalyze nucleophilic addition to esters were screened. Simple nucleophilic catalysts such as dimethylaminopyridine (DMAP) and 2-hydroxylpyridine (HOPy) did not result in significant improvement. The inventor discovered that a series of Lewis acid catalysts, such as Sc(OTf)$_3$ and Yb(OTf)$_3$ were very effective for catalyzing the ring opening polymerization. As shown in Table 1, the model Structure XI

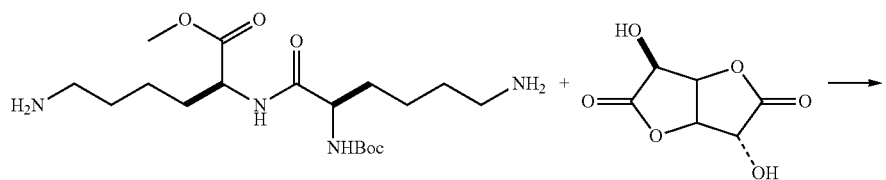

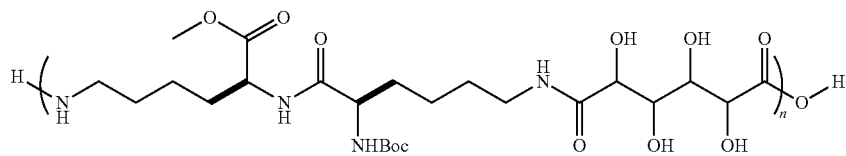

polymerization in pure water at room temperature can afford the polyamide with a number of repeat units of 27. This level of chain length would be sufficient for many applications.

TABLE 1

Model ring-opening polymerization using ethylenediamine and the dilactone as monomers.

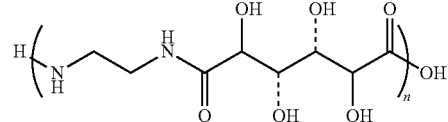

| Solvent | Catalyst | n[a] |
|---|---|---|
| H$_2$O | Sc(OTf)$_3$ | 27 |
| 1:1 MeOH/H$_2$O | Sc(OTf)$_3$ | 18 |
| 1:1 MeOH/H$_2$O | Yb(OTf)$_3$ | 19 |
| H$_2$O | DMAP | <5 |
| H$_2$O | HOPy | <5 |

Note:
[a] n = number of repeat unit.

Glucaramide, N,N'-Diaminoethane Copolymer:

To a stirred solution of glucaric acid 1,4:6,3-dilactone (A) (0.1508 g, 0.8666 mmol, 1 equiv.) in H$_2$O (0.45 mL), was added dropwise a solution of ethylene diamine (2M) in H$_2$O (0.434 mL, 0.8666 mmol) then TEA (0.015 mL, 0.2 equiv.) was added immediately. To this solution, was added a solution of Sc(OTf)$_3$ (0.084 g, 0.2 equiv.) in H$_2$O (0.2 mL). A white precipitate formed in the solution immediately with the addition of Sc(OTf)$_3$ and persisted throughout the reaction. This mixture was allowed to stir for an additional 24 hours at which time the resulting polymer was precipitated from acetone as an off-white solid. The polymer has a Mn=5.3K, Mw=6.53K and an average number of repeat unit of 27.

Ring-Opening Polymerization of Dilactone with Dilysine Monomer

Following the Lewis acid catalyzed ring-opening polymerization conditions identified from model system studies, the polymerization a dilysine monomer with the dilactone were carried out and polymers were obtained (Scheme XVIII)

Scheme XVIII

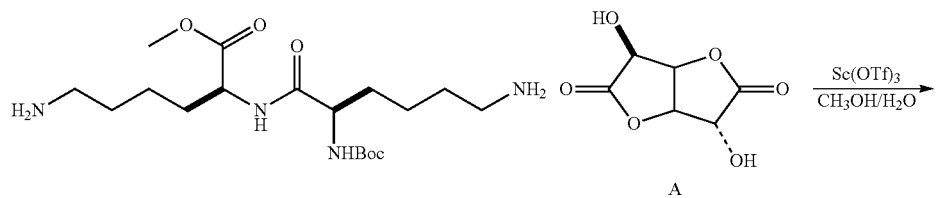

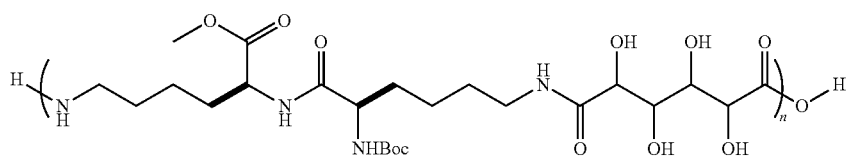

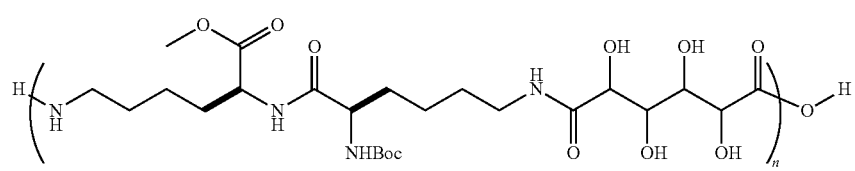

Dilysine-Dilactone Copolymer:

To a stirred solution of glucaric acid 1,4:6,3-dilactone (A) (0.1280 g, 0.7358 mmol, 1 equiv.) in MeOH (0.45 mL), was added dropwise a solution of the dilysine monomer (0.2858 g, 0.7358 mmol, 1 equiv.) in $H_2O$ (0.45 mL) then TEA (0.015 mL, 0.2 equiv.) was added immediately. To this solution, was added a solution of $Sc(OTf)_3$ (0.089 g, 0.2 equiv.) in $H_2O$ (0.2 mL). A precipitate formed and quickly redissolved on the addition of the $Sc(OTf)_3$. This mixture was allowed to stir for an additional 24 hours at which time the resulting polymer was precipitated from acetone as an off-white solid. The polymer characterizations: Mn 4.58K, Mw=8.93K, n=8.70.

Following successful synthesis and characterization of these new cationic polymers, DNA complexation and gene transfection studies were carried out using them as gene carriers. The polyplexes formed between these novel cationic polymers with plasmid DNA were then characterized using EMSA's and AFM visualization. Luciferase assays were performed to examine transfection efficiency. Finally, cell viability experiments were performed to test the hypothesis on the effectiveness of adding carbohydrate spacers to the peptide chain to thereby reduce cytotoxicity of the polymer system.

Polyplex Formation and EMSA's:

The formation of stable polymer/DNA complexes is prerequisite in efficient gene delivery. Following standard protocols, gel electrophoresis was used to characterize the polyplexes. Polyplexes were formed in HEPES buffered saline at pH 7.4 with a salt concentration of 150 mM imitating in vivo ionic strength conditions. The plasmid and the polymer samples were mixed at various N/P ratios and allowed to incubate and complex for 0.5 h. Electrophoresis of the polymer/DNA complexes was then performed in a gel containing ethidium bromide for DNA visualization. An appropriate cationic polymer can bind to DNA causing charge neutralization, which prevents DNA movement down the current gradient of the gel. Each cationic-polymer (Poly 1-3) was shown to effectively retard the movement of pSV-β-gal plasmid DNA at N/P ratios of less than 2.0 (see FIG. 1).

Both Poly 1 and Poly 3 effectively retarded the plasmid DNA at an N/P ratio of 1.5 and Poly 2 retarded the plasmid DNA at a ratio of 2.0 N/P. It is important to note that the polymer/DNA complexes formed at various N/P ratios all remained homogeneous in aqueous solution, which is in contrast to PLL/DNA complexes that were shown to be inhomogeneous. This increased solubility is attributed to the enhanced hydrophilicity introduced by the carbohydrate spacers.

The charge neutralization occurs at relatively low N/P ratios, indicating that these polymers are quite effective at masking DNA charge. The data show that this charge shielding also occurred in aqueous solutions having a high ionic strength (150 mM). Because high salt concentration decreases charge attraction, this observation further supports the binding efficacy of these polymers to plasmid DNA. This ability to neutralize the negative charge on the DNA strand allows compaction of the polyplex, which allows transportation through the cell membrane for gene transfection.

AFM Visualization of the Polyplexes:

The entrance of polyplexes into cells normally occurs through active endocytosis through the cell membrane, which requires initial binding to the cell membrane, envelopment into an endosome, and release from that endosome after internalization. The efficiency with which polyplexes are endocytosed is largely dependent on the physical characteristics of the polyplex, including the particle size. The normal size range for active transport through the cell membrane is 50-200 nm. Above this range cell internalization by endocytosis is less likely. The size and shape of the polymer/DNA complexes were investigated using AFM.

AFM samples were prepared by spin-coating mica slides with 20 µL of polymer/DNA polyplex solutions (as prepared in the EMSA assays). Each polymer condensed DNA into spherical nanoparticles with sizes typically between 50-200 nm in diameter. The following size distributions were observed for the polyplexes having 20 and 40 N/P ratios: For Poly 1, at the 20 and 40 N/P ratios, 87.4% of the particles where 50-200 nm in diameter. For Poly 2, at the same N/P ratios, 90.2% of the particles were 50-200 nm in diameter. Finally, for Poly 3, 95.3% of the polyplexes were 50-200 nm in diameter.

The EMSA and AFM studies demonstrated the carbohydrate-peptide copolymers could effectively compact plasmid DNA to form nanoparticles with sizes primarily below 200 nm. These data suggested that the carbohydrate-peptide cationic polymers were suitable for further study in gene delivery applications.

Gene Transfection Results.

The transfection efficiency of the three hybrid polymers was tested and compared with PLL. PLL was selected as a control because it is one of the most studied polymeric gene transfection vectors, and as the remaining polymers comprised L-lysine. Transfection studies were carried out using a commercially available COS-7 cells and a luciferase assay kit.

Following known literature procedures, gene transfection studies were conducted in serum free conditions with the addition of chloroquine, an additive base known to disrupt the membrane of endosomes and aid endosomal escape for the polyplexes. After internalization by endocytosis, if the polyplexes are unable to efficiently escape from endosomes, they will pass into highly acidic lysosomes, which causes degradation of the DNA. An effective mechanism to enhance the endosomal release of polyplexes is the use of proton sponge effect, in which the polymer carrier becomes more highly protonated while in the acidic endosomes. This triggers chloride influx across the endosomal membrane and water follows to counter the high ion concentration inside the endosome. The osmotic pressure eventually leads to endosomal rupture and release of the entrapped DNA. Because the L-lysine and other primary amino groups have relatively high $pK_a$'s and should not have any proton sponge effects, the addition of chloroquine was commonly employed to enhance the endosomal release and, hence, increase the gene transfection efficiency. For gene transfection studies of new synthetic nonviral vectors, serum free conditions were also commonly used in previous reports.

Figure 2A:
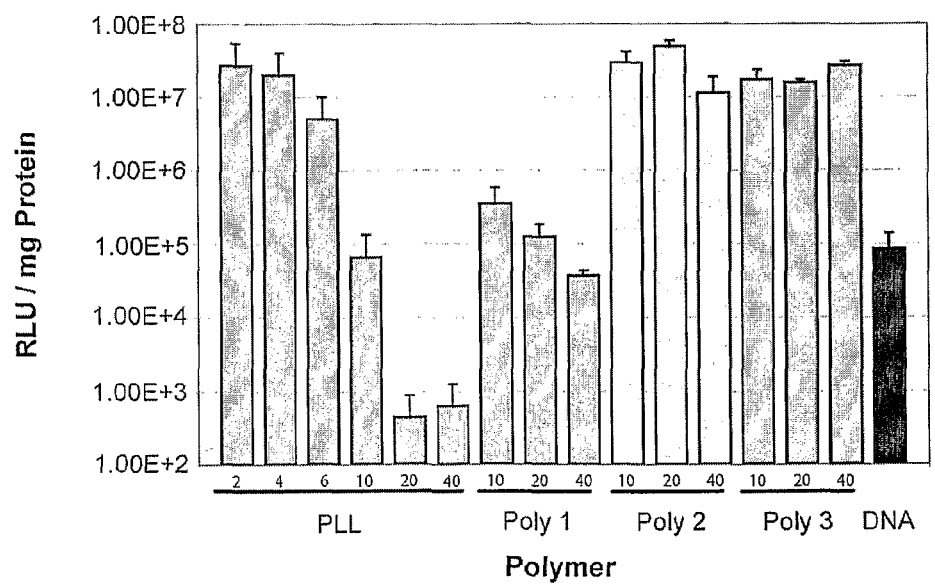
FIG. 2A is a graph depicting transfection efficiency of cells contacted with control and various of the chimeric polymer DNA preparations presented herein.

Cells were pre-incubated with chloroquine for 4 h prior to addition of experimental and control polyplexes which were then incubated for 5 h under serum-free conditions. Serum was then added and an additional 24 h incubation time elapsed. The cells were then lysed and their relative light units (RLU) normalized to total cellular protein/well was measured. The results of this experiment are depicted in the Graph of FIG. 2A. As can be seen, both Poly 2 and Poly 3 surpass PLL in gene transfection with transfection levels approaching the 1.00 E+08 RLU/mg protein mark.

These results show that Poly 2 and Poly 3 can efficiently deliver genes across the cell membrane. Poly 1 has significantly lower transfection efficiency, which is thought to be attributable to its structure: Poly 1 has only one $\alpha$-$NH_2$ group per repeat unit. The cationic charge density on this polymer is the lowest among the three polymers, which may lead to weaker binding to DNA. The difference in $pK_a$ values and binding geometry between the $\alpha$-$NH_2$ and $\epsilon$-$NH_2$ cationic sites in Poly 1 compared to Poly 2 or 3 may also contribute to the different gene transfection efficiency. Several systems have shown that very subtle structural changes can result in significant differences in DNA binding and the subsequent gene delivery properties. One study showed that the distance of side chain cationic charges from a polymer backbone had a significant influence on the complexes formed with DNA.

The transfection levels are competitive with PLL at several concentrations and charge ratios, but are slightly lower than some of the most efficient synthetic polymeric systems such as PEI, which was shown to have higher transfection efficiency than PLL. However, because of the ease with which structural permutations can be performed using the polymer system of the inventive subject matter, the efficiency of that hybrid system could be further modified. For example, because endosomal escape is a problem for some of the current polymers, adding amino groups with a lower $pK_a$'s (such as histidine residues $pK_a$~5.2) that only become protonated at lower pH's (such as the environment in the endosome) could potentially improve the transfection efficiency.

Cell Proliferation Studies.

Figure 2B:
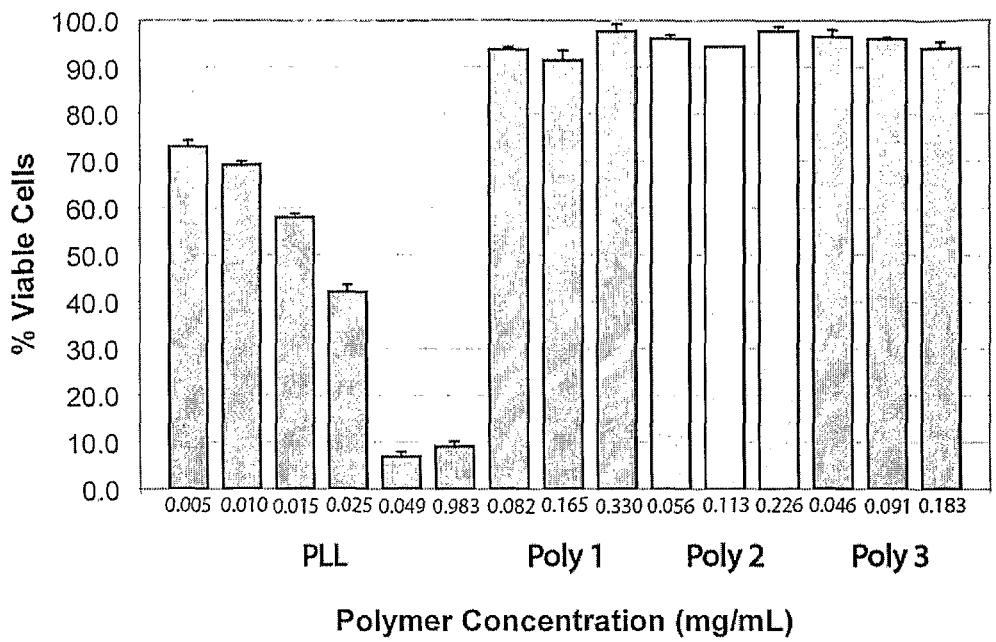
FIG. 2B is a graph depicting viability of cells incubated with control and various of the chimeric polymers presented herein.

A critical issue for synthetic gene delivery vectors is that the highly efficient synthetic vectors, such as PEI, usually have high cytotoxicity. This significantly hinders their development into clinical trials for gene therapy. In developing new carriers, it is critical to find out their cytotoxicity levels. The inventor tested the cytotoxicity of the carbohydrate-peptide polymers using the standard tetrazolium-based MTT test. The testing was done at polymer concentrations corresponding to those used in the transfection experiments. The difference in toxicity between the hybrid copolymers and the control PLL (of a similar $M_n$, 8500 g/mol) was unexpected. As can be taken from FIG. 2B, even at high concentrations of the hybrid polymers, the cytotoxicity approaches that of negative controls, with cell viability of 92-98% after a 24 h incubation time. In contrast, PLL showed much higher toxicity at every concentration used in the studies.

These test results with pure copolymers should represent the maximum cytotoxicity because previous studies indicate that complexation with DNA usually reduces the cytotoxicity for cationic polymers. In cationic polymers, cytotoxicity often stems from interaction of the cationic polymer with the cell membrane, which causes lysis of the membrane and cell death. Cell membrane disruption by cationic polymers can be influenced by three major factors: Amino functionality type (primary amine being the most toxic and tertiary amine the least), polymer concentration, and cationic charge density (increased charge density of polymer chains causes improved interactions with the cell membrane resulting in cytoplasmic leakage). If the cationic polymer has high charge density and is able to interact readily with the cell membrane, having many proximal attachment points, it is more likely to be cytotoxic.

The cell viability results further show that the galactara-peptide copolymers exhibit essentially no cytotoxicity even at high polymer concentrations. While the exact mechanism for this dramatic reduction of cytotoxicity is unclear, the working hypothesis is as follows. First, separating cationic peptides into short segments decreases the continuous charge density, leading to lower cytotoxicity. In oligo-L-lysine studies, it has been shown that the cytotoxicity increases with the length of the oligomers, which indicates high continuous charge density has disruptive effects on cell membrane. Second, the hydrophilic carbohydrate fragments can shield the surface charges of the DNA-polymer complexes, reducing their ζ-potential, and therefore, mitigating membrane disruption. Moreover, when the cationic peptide segments bind to plasmid DNA in the carbohydrate-peptide hybrid copolymers, it is thought that the flexible carbohydrate spacers may bulge out and shield the polyplex surface charges. As a consequence, cytoxicity may be reduced.

Immunological Studies on Carbohydrate-Peptide Polymer

Besides low cytotoxicity, low immunogenicity is another important criterion for a safe gene delivery vector. Early studies found that random linear homopolymers of amino acids were rarely antigenic. However, since contemplated carbohydrate-peptide copolymers are new compounds, it is important to find out if they generate any immune response in animals. A tetralysine copolymer (Poly A) was chosen with a $M_n$ of 9000 g/mol to conduct various immunological evaluations using Fisher 344 rats as animal models. Since the copolymer is a polydispersed sample which contains a distribution of species having different molecular weight, the test results should be representative for both high and low molecular weight species.

Individual Fisher 344 rats underwent saphenous vein phlebotomy and serum was stored at −20° C. until use as pre-immune serum. Cohorts of rats received 100 μg of Poly A, without adjuvant, as 50 μL subcutaneous (SC) injections in the footpad or 100 μL intravenous (IV) tail vein injections. Poly A was administrated at the first, third and sixth weeks, respectively. Animals underwent phlebotomy 21 days following each additional administration of the polymer. Serum was obtained at the sixth and ninth week and stored at 4° C. until use.

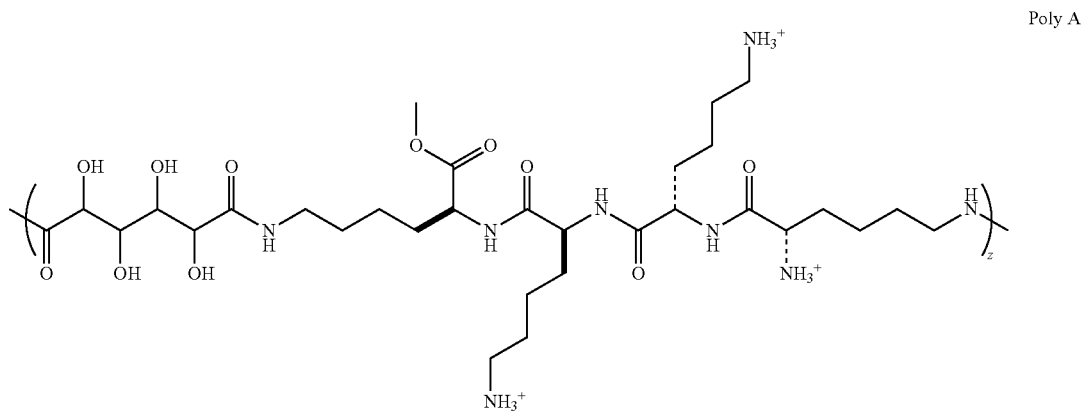

Individual wells of a 96 well Immulon MaxiSorb microtiter plate were coated with 100 μL of either Poly A at a concentration of 3 μg/mL or normal rat serum (positive control) and incubated overnight at 4° C. Rat serum samples from normal, IV administered, and SC injected Poly A rats were added to the wells (50 μL/well), without dilution, and incubated for 1 hour at RT. Wells were washed with 200 μL of 0.1% tween-20 1×PBS 4 times. Anti-rat IgG (H+L) HRP was diluted 1:3000 in 1% BSA 1λPBS and added to the wells (100 μL/well) for 1 hr at RT. Wells were washed with 200 μL of 0.1% tween-20 1λPBS 4 times. TMB (75 μL/well) was added and incubated for 15 minutes. After the reaction was arrested by adding 25 μL of 2N HCl, the plate was read at 490 nm in a microplate reader.

Figure 3:
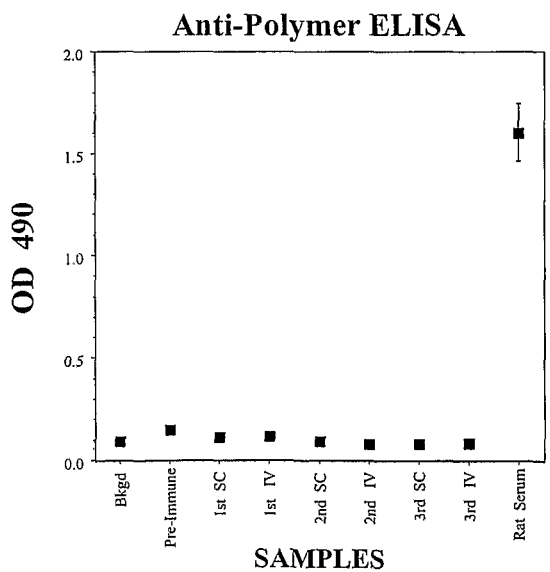
FIG. 3 is a plot depicting ELISA results for various time points of immune reaction against certain chimeric polymers.

The graph in FIG. 3 presents the average and SD of OD for individual cohorts from these ELISA. Here, anti-polymer ELISA data are depicted, which include the results for background, pre-immune serum, subcutaneous (SC), intravenous (IV), and normal rat serum (positive control). The 1st, 2nd and 3rd sera were taken at the 3rd, 6th and 9th weeks, respectively. The ELISA data demonstrate that there is no detectable antibody response over background after three administrations of the polymer A by either SC or IV routes. There is no evidence of any antibody response and all rats are healthy (no weight loss, normal activity, good hygiene/quality fur), suggesting that there is no other adverse immune response or toxicity. These data demonstrate that the carbohydrate-peptide polymers of the present invention are neither immunogenic nor toxic.

Enzymatic Degradation of Saccharide-Peptide Hybrid Copolymers

Enzymatic degradation studies were performed on Poly 1-3 for which the structures were shown in Structure V. As monitored by MALDI-TOF mass spectrometry, the molecular weights of the polymers decrease with incubation time which indicates that the polymers were degraded by the enzymes.

Figure 4A:
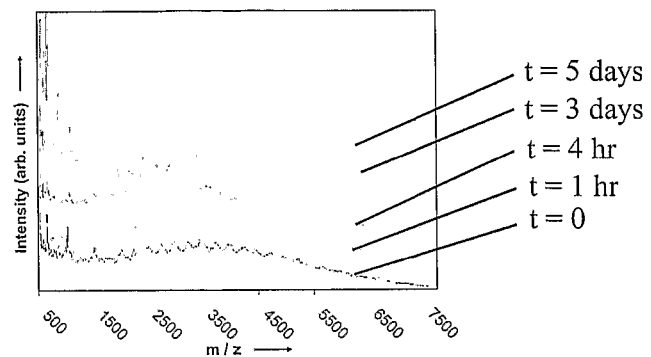
FIG. 4A is a graph depicting the results of the degradation study using subtilisin A and the dilysine polymer (Poly 1).

Biodegradation Study Using Subtilisin A as a Catalyst for Poly 1:

To a solution of phosphate buffered saline (1.38 mL, PBS, 120 mM NaCl, 2.7 mM KCl, 10 mM phosphate buffer) and subtilisin A (0.138 mg, 11 U/mg, from *bacillius globigii*), was added Poly 1 (13.8 mg). This solution was allowed to stir at 38° C. for the duration of the experiment. Aliquots (100 μL) were taken at appropriate time intervals and diluted with MeOH (200 μL). Aliquots (1 μL) of a saturated solution of α-cyano-4-hydroxy cinnamic acid in H$_2$O/MeOH (1:2) were spotted to a MALDI sample plate as a matrix. These samples were allowed to air dry at which time different dilutions of the MeOH diluted degradation solutions were added to the matrix. MALDI data was exported to Excel™ and plotted using a tread line smoothed using a running average of 100 points. FIG. 4A depicts the results of the degradation study using subtilisin A and the dilysine polymer (Poly 1).

Figure 4B:
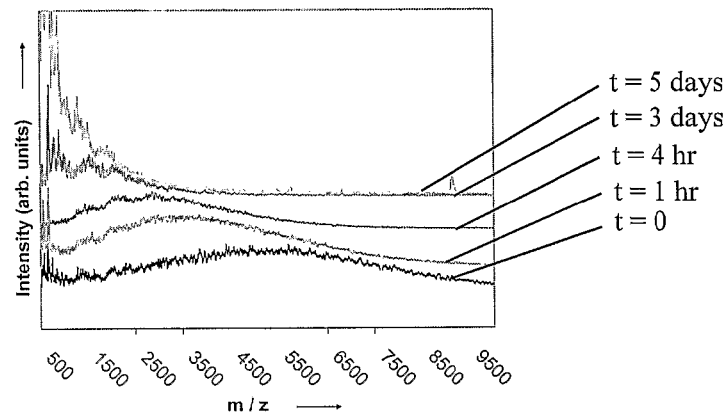
FIG. 4B is a graph depicting the results of the degradation study using subtilisin A and the trilysine polymer (Poly 2).

Biodegradation Study Using Subtilisin A as a Catalyst for Poly 2:

To a solution of phosphate buffered saline (2.6 mL, PBS, 120 mM NaCl, 2.7 mM KCl, 10 mM phosphate buffer) and subtilisin A (0.26 mg, 11 U/mg, from *bacillius globigii*), was added Poly 2 (12.9 mg). This solution was allowed to stir at 38° C. for the duration of the experiment. Aliquots (100 μL) were taken at appropriate time intervals and diluted with MeOH (200 μL). Aliquots (1 μL) of a saturated solution of α-cyano-4-hydroxy cinnamic acid in H$_2$O/MeOH (1:2) were spotted to a MALDI sample plate as a matrix. These samples were allowed to air dry at which time different dilutions of the MeOH diluted degradation solutions were added to the matrix. MALDI data was exported to Excel™ and plotted using a tread line smoothed using a running average of 100 points. FIG. 4B depicts the results of the degradation study using subtilisin A and the trilysine polymer (Poly 2).

Figure 4C:
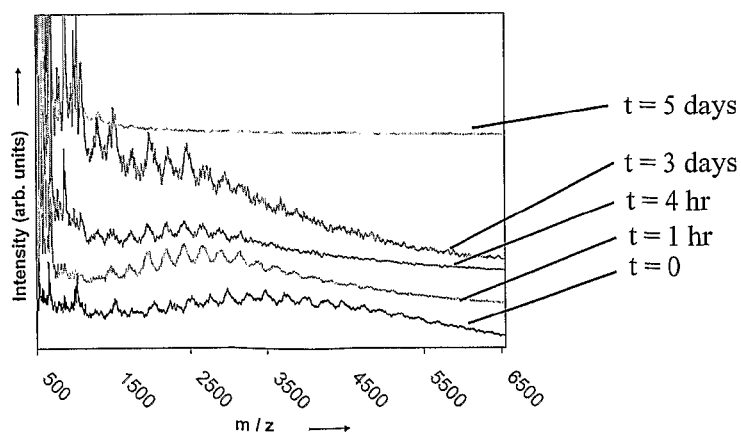
FIG. 4C is a graph depicting the results of the degradation study using trypsin and dilysine polymer (Poly 1).

Degradation Study Using Trypsin as a Catalyst for Poly 1:

To a solution of phosphate buffered saline (1.07 mL, PBS, 120 mM NaCl, 2.7 mM KCl, 10 mM phosphate buffer) and trypsin (0.0011 mg, 10.2 U/mL from bovine pancreas), was added Poly 1 (10.7 mg). This solution was allowed to stir at 38° C. for the duration of the experiment. Aliquots (50 μL) were taken at appropriate time intervals and diluted with MeOH (100 μL). Aliquots (1 μL) of a saturated solution of α-cyano-4-hydroxy cinnamic acid in H$_2$O/MeOH (1:2) were spotted to a MALDI sample plate as a matrix. The samples were allowed to air dry at which time different dilutions of the MeOH diluted degradation solutions were added to the matrix. MALDI data was exported to Excel™ and plotted using a tread line smoothed using a running average. FIG. 4C depicts the results of the degradation study using trypsin and dilysine polymer (Poly 1).

Synthesis of Tyrosine-Containing Sacchride-Peptide Copolymers

The inventor contemplated to use tyrosine oxidative coupling as one means to cross-link the invented polymers for formation of hydrogels. This cross-linking method should proceed rapidly with visible light as a photo-initiator, or with a peroxidase enzymes as catalysts (in the biosynthetic pathway). For this purpose, a tyrosine-containing comonomer was synthesized as outlined in the following Scheme XIX:

Scheme XIX

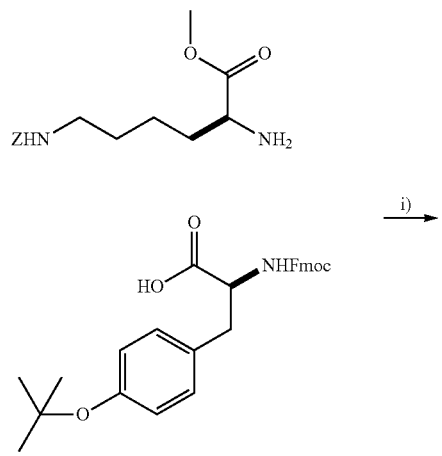

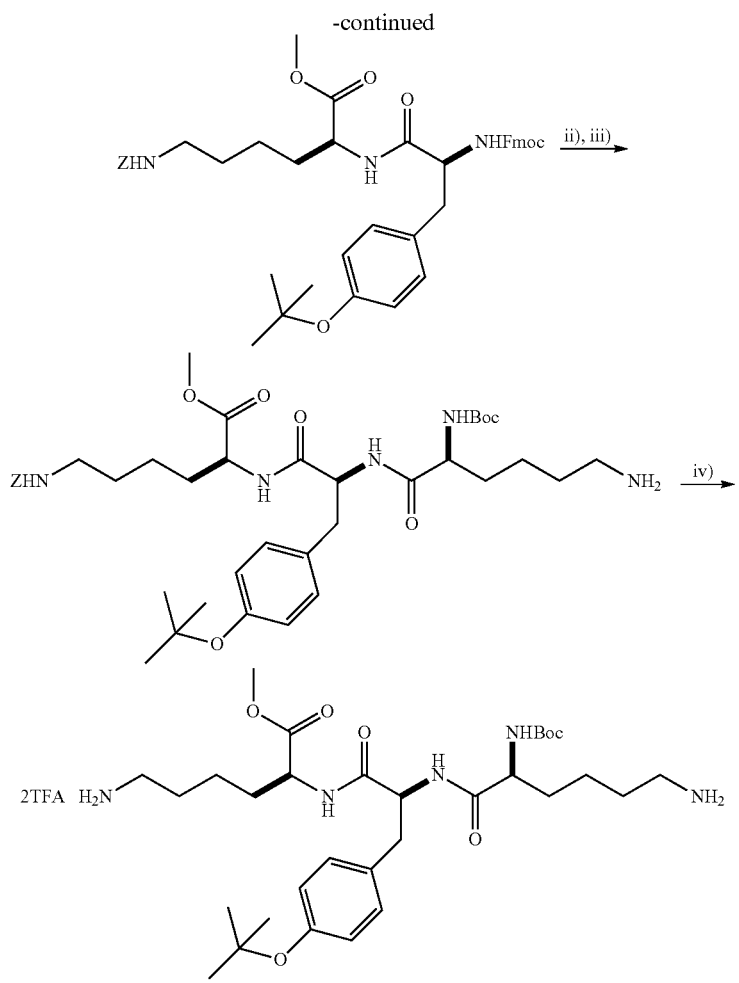

Reaction Conditions: i) EDC, HOBt, DIPEA, 12 h, 90% yield.
ii) DMA (2M), THF.
iii) BocLys(Z)OH, EDC, HOBt, DIPEA, 12 h, 60% yield.
iv) Pd/C, 2 equiv. TFA, 12 h, 95% yield

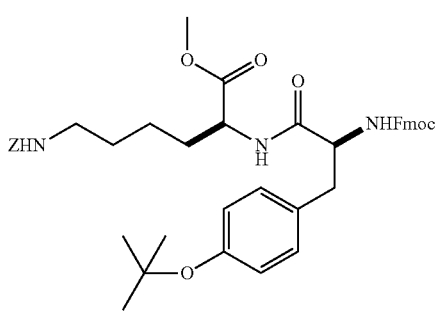

Synthesis of Fmoc-Tyr(tBu)-Lys(Z)-OMe:

To a solution of diisopropylethyl amine (1.19 mL, 3.43 mmol) in DCM (50 mL), was added Lys(Z)OMe (1.13 g, 3.43 mmol). To this solution was added FmocTyr(tBu)OH (1.50 g, 3.26 mmol), then HOBt (0.463 g, 3.43 mmol), and finally EDC.HCl (0.6571 g, 3.43 mmol). This solution was allowed to stir for 8 h at which time the organic solution was washed with 1N HCl (2×20 mL), then saturated NaHCO$_3$ (2×20 mL), and finally H$_2$O (2×20 mL). The organic layer was concentrated in vacuo to yield a white solid (2.34 g, 97.5% yield): $^1$H NMR (500 MHz, CDCl$_3$) δ 7.77 (d, J=7.53, 2H), 7.55 (m, 2H), 7.40 (t, J=7.45, 2H), 7.38-7.29 (m, 7H), 7.08 (m, 2H), 6.88 (d, J=8.25, 2H), 6.43 (br s, 1H), 5.52 (br s, 1H), 5.15-5.07 (br m, 3H), 4.50 (m, 1H), 4.42 (m, 1H), 4.30 (m, 1H), 4.18 (t, J=6.92, 1H), 3.70 (s, 3H), 3.18-2.95 (m, 4H), 1.85-1.35 (m, 4H), 1.30 (s, 10H), 1.20 (br s, 2H); $^{13}$C NMR (125 MHz, CDCl$_3$) δ 163.0, 154.6, 143.9-143.8 (3), 141.46, 136.6, 130.0, 128.7, 128.2, 127.9, 127.3, 125.2, 124.5, 120.2 (2), 67.13, 66.8, 53.6, 52.6, 47.3, 41.0, 37.8, 32.6, 29.4, 29.0 (3), 22.17; HRMS (FAB) m/z calcd for C$_{43}$H$_{49}$N$_3$O$_8$ (M+H)$^+$ 736.3598, found 736.3623.

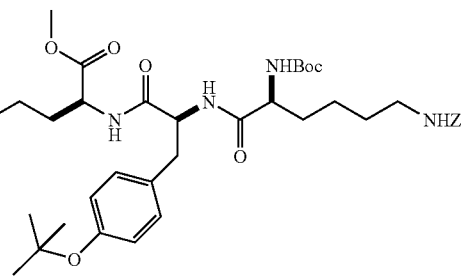

Synthesis of Boc-Lys(Z)-Tyr(tBu)-Lys(Z)-Ome:

To a solution of Fmoc-Tyr(tBu)-Lys(Z)-OMe (7.72 g, 10.49 mmol) in THF (105 mL), was added dimethyl amine (52.5 mL, 2 M, 104.9 mmol). This reaction was allowed to reach room temperature and stirred for 1.5 h. At this time, the reaction mixture was concentrated in vacuo. To the yellowish solid, was added DCM (225 mL) and DMF (45 mL). To this solution, was added Boc-Lys(Z)—OH (4.19 g, 11.01 mmol), then HOBt (1.488 g, 11.01 mmol), then EDC.HCl (2.112 g, 11.01 mmol). This solution was allowed to stir for 8 h at which time the organic solution was washed with 1 N HCl (3×100 mL), then saturated NaHCO$_3$ (3×100 mL), and finally H$_2$O (3×100 mL). The organic layer became jelly like and MeOH was added to break the gel. The organic layer was dried over MgSO$_4$ and concentrated in vacuo to yield a white solid. Column chromatography (0-1% MeOH, CHCl$_3$) afforded the product (5.51 g, 65% yield).

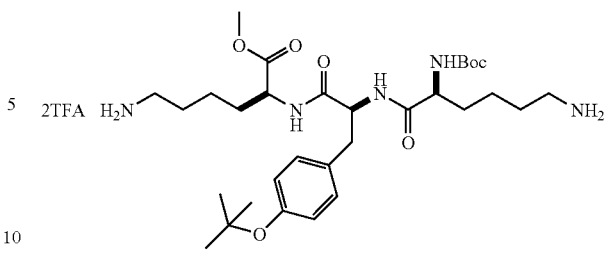

Synthesis of Boc-Lys-Tyr(tBu)-Ly-OMe (KYK):

To a solution of BocLys(Z)Tyr(tBu)Lys(Z)OMe (1.79 g, 2.04 mmol) in MeOH (113 mL) and TFA (0.304 mL, 2 equiv.), was added Pd/C (catalytic). This solution was flushed with H$_2$ for 30 min. and then fitted with a H$_2$ balloon. The reaction was allowed to proceed for 8 h at which time the mixture was filtered through celite, and conc. in vacuo to yield pure clear product (1.63 g, 95% yield). The tyrosine-containing monomer was then copolymerized with galactoryl chloride to form a tyrosine-containing copolymer:

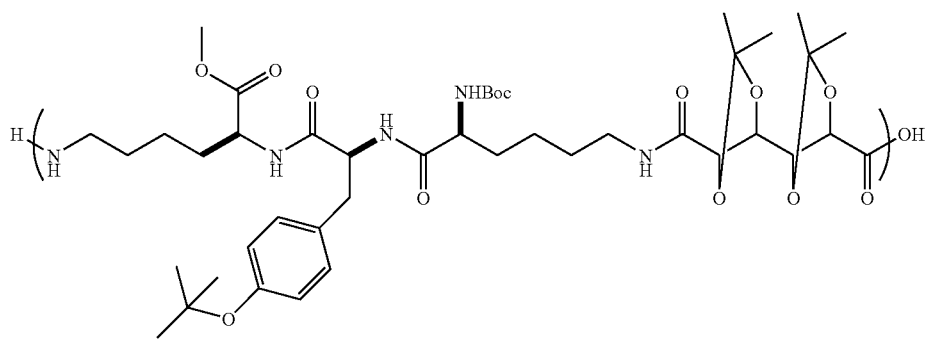

Synthesis of the Protected Galactara-KYK Copolymer:

Boc-Lys-Tyr(tBu)-Lys-OMe (0.881 g, 1.05 mmol) along with Na$_2$CO$_3$ (0.369 g) was stirred in 30.0 mL of H$_2$O. To this vigorously swirling solution, was added a solution of galactoryl chloride (0.345 g, 1.05 mmol) in 10 mL CCl$_4$. This biphasic mixture was stirred for 30 min at room temperature. The precipitate was collected by filtration and washed with water to yield a white solid. The polymer was characterized: M$_n$=4.9 kg/mol, M$_w$=8.9 kg/mol.

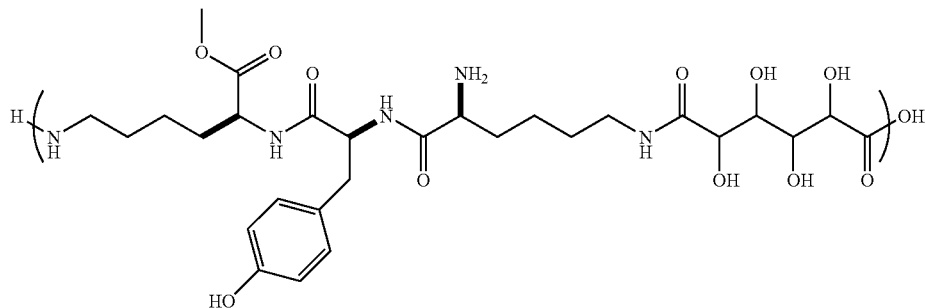

Deprotection of the fully protected galactara-trilysine copolymer: To a solution of 50% TFA in $H_2O$ (15.0 mL) was added to protected polymer (0.600 g). After 4 h, the solution was concentrated providing the deprotected polymer (quantitative). To increase the copolymer's water solubility, the following terpolymer was also synthesized through copolymerization of a dilysine monomer (KK), a tyrosine-containing comonomer (KYK), and a carbohydrate diacid chloride monomer. As one example shown in the Scheme XX, the synthesis of one such a polymer was performed using 0.3 equivalents of the KYK monomer and 0.7 equivalents of the KK monomer.

Scheme XX

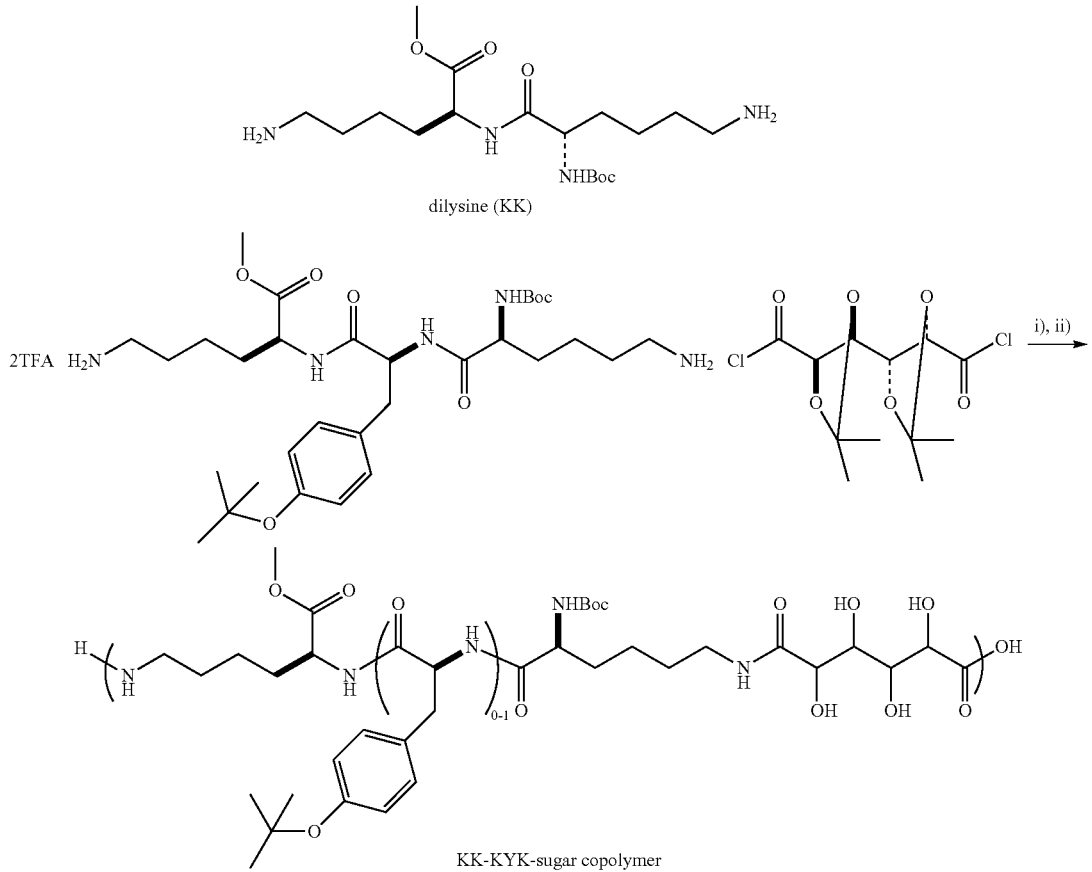

Reaction Conditions:
i) 0.3 equiv. KYK, 0.7 equiv. KK, 1.0 equiv sugar diacid chloride, $H_2O/CCl_4$, $M_n$ = 13K, $M_w$ = 21K
ii) TFA/Water NMR showed about 50:50 molar ratio of the KK and KYK monomer units in the polymer chain. This means that the KYK monomer was somewhat more reactive than the KK monomer. The $M_n$ of the KK-KYK-sugar copolymer is higher than the copolymer of the KYK comonomer and the sugar diacid chloride. The synthetic details are described as follows.

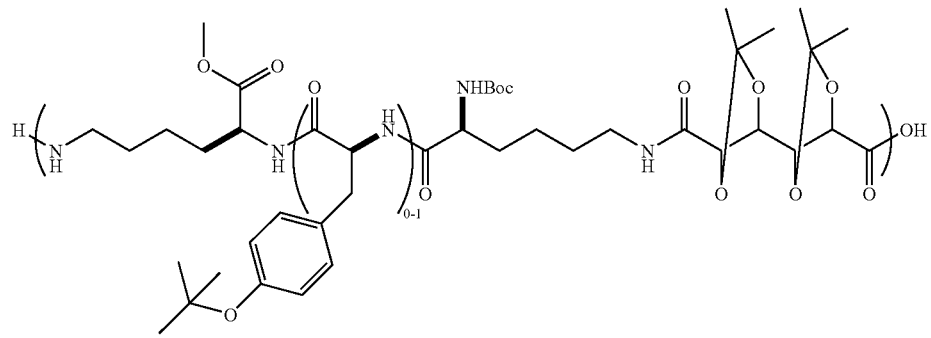

KK-KYK-sugar copolymer

Synthesis of the Protected KK-KYK-Sugar Copolymer:

Boc-Lys-Tyr(tBu)-Lys-OMe (0.332 g, 0.386 mmol), Boc-Lys-Lys-OMe (0.528 g, 0.856 mmol) along with $Na_2CO_3$ (0.434 g) was stirred in a beaker containing 28.0 mL of $H_2O$. To this swirling solution, was added a solution of galactoryl chloride 4 (0.406 g, 1.24 mmol) in 12 mL $CCl_4$. This biphasic mixture was stirred for 30 min at room temperature. The precipitate was collected by filtration and washed with water to yield a white solid (0.380 g yield): $M_n$=12.9 kg/mol, $M_w$=20.4 kg/mol.

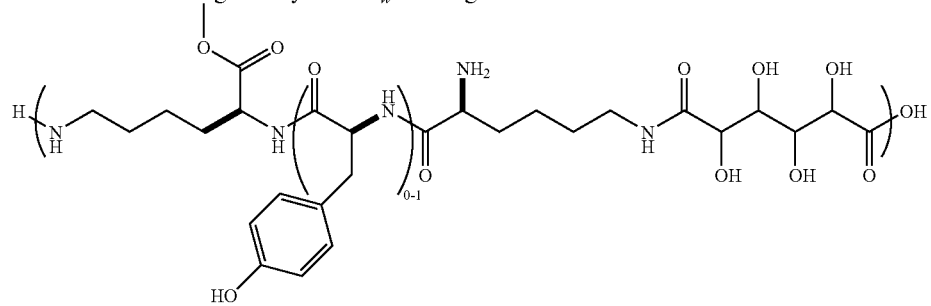

Deprotection of the Fully Protected KK-KYK-Sugar Copolymer:

To a solution of 50% TFA in $H_2O$ (10.0 mL) was added to protected polymer (0.380 g). After 4 h, the solution was concentrated providing the deprotected polymer (quantitative).

Cross-Linking the Tyrosine-Containing Copolymers to Form Hydrogels

As illustrated previously in Scheme IV, the inventor contemplated two methods for cross-linking tyrosine-containing copolymers in aqueous solution. The first uses $Ru(III)(bpy)_3$ as an oxidant (generated from $Ru(II)(bpy)_3$, ammonium persulfate and light). The second uses a peroxidase and hydrogen peroxide in the presence of superoxide dismutase. It was demonstrated here that both chemical and enzymatic routes were efficient to cross-link the tyrosine-containing copolymers into hydrogels (Scheme XXI)

Scheme XXI

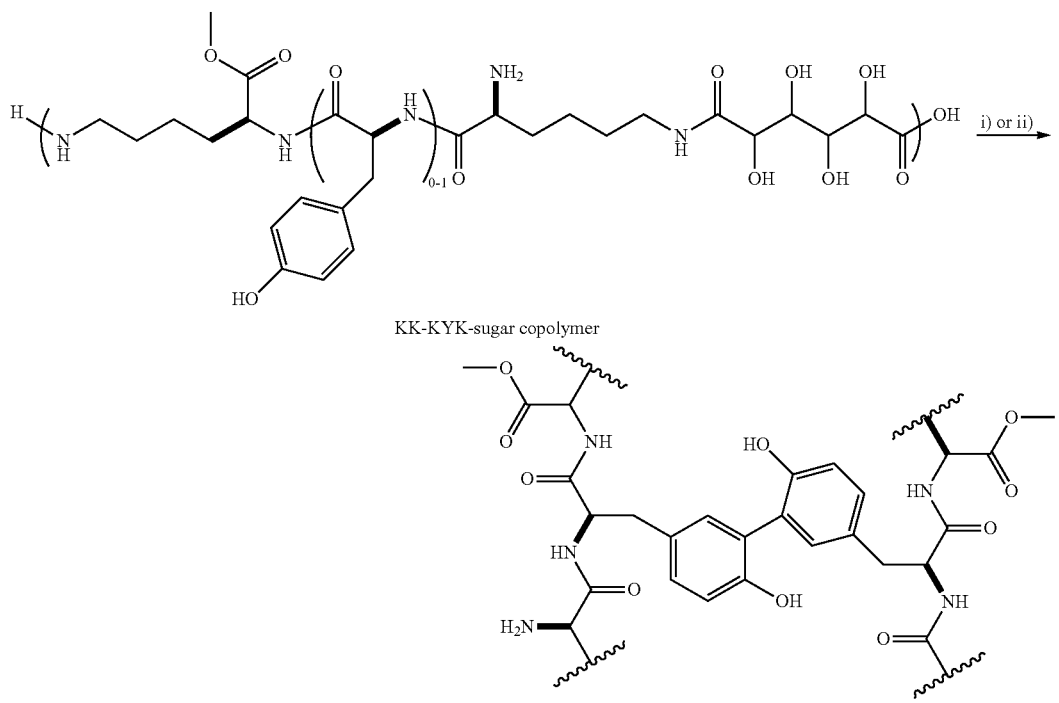

Reaction Conditions: i) $Ru(II)(bpy)3Cl2$, Ammonium Persulfate, Visible Light, 180-120 s.
ii) HOOH, superoxide dismutase, Horse Radish Peroxidase (HRP)

Detailed conditions for hydrogel formation is described as follows:

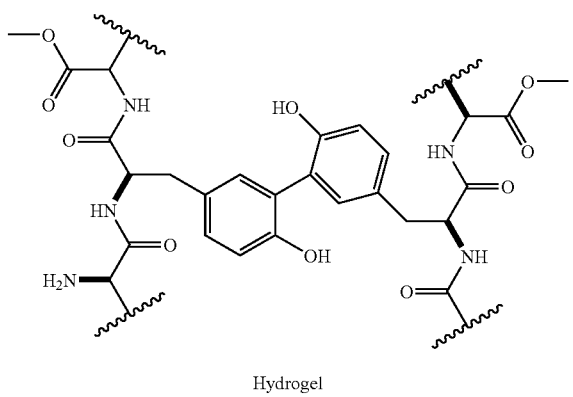

Hydrogel

Hydrogel formation using Ru(II) catalyst: To a solution of KK-KYK-sugar copolymer (70.0 mg) in PBS (0.250 mL) was added enough NaOH (2.5 M, 3 drops), to precipitate the polymer. The polymer was brought back into solution with a minimum amount of HCl (0.1 M, 8 drops). Then, to this solution was added Ru(II)(bpy)$_3$Cl$_2$.2H$_2$O (1.5 mg, 0.002 mmol) and a solution of ammonium persulfate (1.55 mg, 0.00679 mmol) in PBS (0.100 mL). This solution was mixed thoroughly and irradiation for 180 s. A translucent orange gel formed.

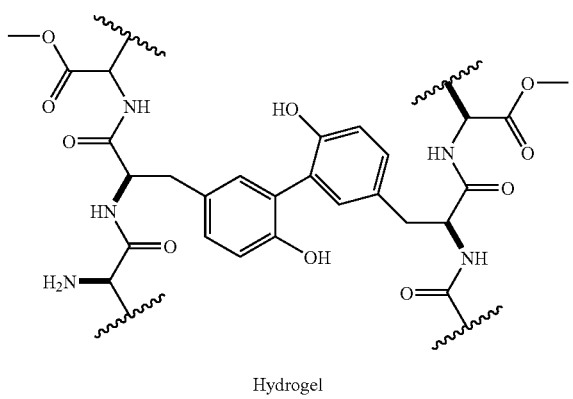

Hydrogel

Hydrogel formation using HOOH and HRP: To a solution of KK-KYK-sugar copolymer (70.0 mg) in boric acid/borate buffer (0.25 M, 0.250 mL) was added enough NaOH (2.5 M, 2 drops), to precipitate the polymer. The polymer was brought almost completely back into solution with a minimum amount of HCl (0.10 M, 8 drops). Then, to this solution was added HRP (1.75 mg) and SOD (1.75 mg). This solution was mixed thoroughly, then to it was added a solution of HOOH (28 μL, 0.03% solution). A slightly tan colored gel formed within 5 minutes.

Cell Culture on KK-KYK-Sugar Copolymer Hydrogels

Several hydrogels using the conditions as described were prepared for cell growth studies. The as formed hydrogels were washed with PBS buffer a few times until they were not acidic. As one example for cell culture experiment, smooth muscle cells (SMC's) were seeded onto the gels and their growth was monitored. The cells were growing healthily after 5 days.

New Tyrosine-Containing Copolymer Synthesis

To improve the solubility of the copolymers at higher pH, acidic moieties were included in the following hydrophilic polymer design. For this purpose, Scheme XXII below shows the synthesis of a KK monomer that has a cleavable acid group:

Scheme XXII

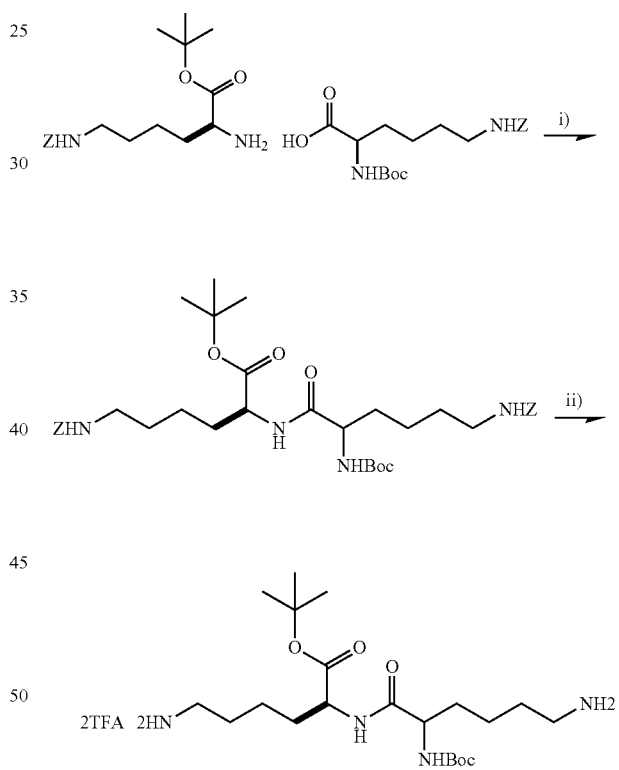

Reaction Conditions: i) EDC, HOBt, DIPEA, 12 h, 90% yield.
ii) Pd/C, 2 equiv. TFA, 12 h, 95% yield This monomer was then used in interfacial polymerizations as test conditions for copolymerization with the KYK monomer as outlined in Scheme XXIII below. The polymerization proceeded well with an Mn of 9118 and an Mw of 14.390 g/mol. The TFA deprotection of the t-butyl ester took 24 hours compared to the deprotection of the acetonide and Boc protecting groups which only takes around 3 hours.

Scheme XXIII

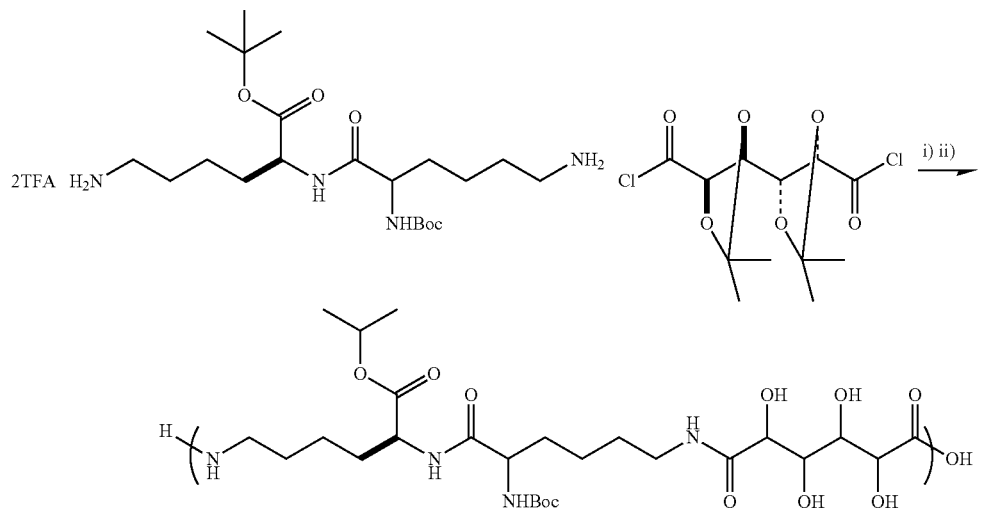

Reaction Conditions: i) 1.0 equiv. KK, 1.0 equiv diacid chloride, $H_2O/CCl_4$, $M_n$ = 9.1K, $M_w$ = 14.5K;
ii) 1:1 TFA/Water 24 hours This new monomer and the KYK monomer were also copolymerized with a sugar diacid chloride to form the following terpolymer (Scheme XXIV). The molecular weight of this polymer was comparable to that of the previous KK-KYK-sugar copolymer system, with an Mn of 8.6K and an Mw of 13.5K.

Scheme XXIV

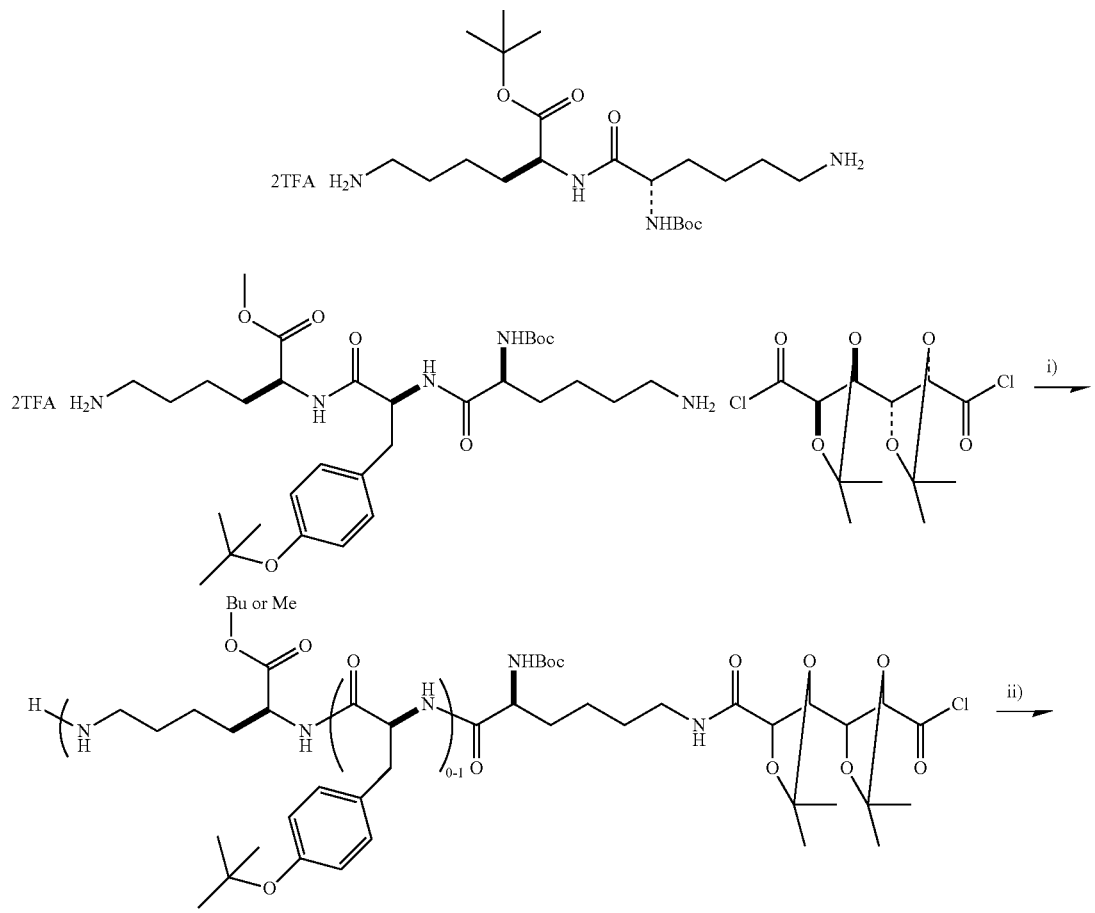

-continued

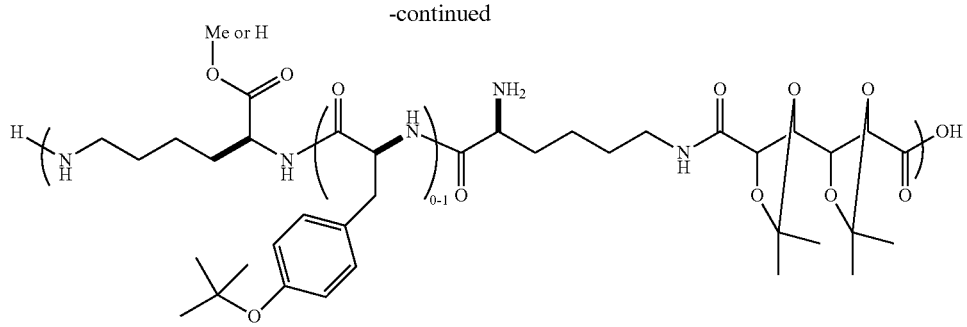

Reaction Conditions: i) 0.70 equiv. KKOtBu, 0.30 equiv KYK, 1.0 equiv diacid chloride, $H_2O/CCl_4$, $M_n$ = 8.6K, $M_w$ = 13.5K;
ii) 1:1 TFA/Water 24 hours.

Still further data, experiments, and considerations are described in Angew. Chem. Int. Ed. 2005, 44, 6529-6533, along with the supporting information (e.g., electronically available at www.angewnadte.org), which are expressly incorporated by reference herein.

REFERENCES (1) Luo, D., and Saltzmann, W. M. (2000) *Nat. Biotechnol.* 18, 33-37.
(2) Wolff, J. A. (2002) *Nat. Biotechno* 20, 768-769.
(3) Zhu, J., Grace, M., Casale, J., Chang, A., Musco, M. L, Bordens, R., Greenberg, R., Schaefer, E., and Indelicato, S. (1999) *Human Gene Therepy* 10, 113-121.
(4) Felgner, P. L. (1997) *Sci. Am.* 276, 102-106.
(5) Friedmann, T. (1997) *Sci. Am.* 276, 96-101.
(6) De Smedt, S. C., Demeester, J., and Hennink, W. E. (2000) *Pharmaceutical Res.* 17, 113-126 and references therein.
(7) Kakizawa, Y., and Kataoka, K. (2002) *Adv. Drug Deliv. Rev.* 54, 203-222.
(8) Zauner, W., Ogris, M., and Wagner, E. (1998) *Adv. Drug. Deliv. Rev.* 30, 97-113.
(9) Fischer, D., Li, Y., Ahlemeyer, B., Krieglstein, J., and Kissel, T. (2003) *Biomaterials* 24, 1121-1131.
(10) Akinc, A., Lynn, D. M., Anderson, D. G., and Langer, R. (2003) *J. Am. Chem. Soc.* 125, 5316-5323.
(11) Reineke, T. M., and Davis, M. E. (2003) *Bioconjugate Chem.* 14, 247-254.
(12) Lim, Y., Kim, C., Kim, K., Kim, S. W., and Park, J. (2000) *J. Am. Chem. Soc.* 122, 6524-6525.
(13) Putnam, D., Gentry, C. A., Pack, D. W., and Langer, R. (2001) *Proc. Natl. Acad. Sci. USA* 98, 1200-1205.
(14) Wang, J., Mao, H.-Q., and Leong, K. W. (2001) *J. Am. Chem. Soc.* 123, 9480-9481.
(15) Forrest, M. L., Koerber, J. T., and Pack, D. W. (2003) *Bioconjugate Chem.* 14, 934-940.
(16) Thomas, M., and Klibanov, A. M. (2002) *Proc. Natl. Acad Sci. USA* 99, 14640-14645.
(17) Zanta, M. A., Belguise-Valladier, P., and Behr, J. P. (1999) *Proc. Natl. Acad. Sci. USA* 96, 91-96.
(18) McAllister, K., Sazani, P., Adam, M., Cho, M., Rubinstein, M., Samulski, R. J., and DeSimone, J. M. (2002) *J. Am. Chem. Soc.* 124, 15198-15207.
(19) Liu, Y., Wenning, L., Lynch, M., and Reineke, T. M. (2004) *J. Am. Chem. Soc.* 126, 7422-7423.
(20) Malik, N., Wiwattanapatapee, R., Klopsch, R., Lorenz, K., Frey, H., Weener, J. W., Meijer, E. W., Paulus, W., and Duncan, R. (2000) *J. Controlled Release.* 65, 133-148.
(21) Howard, K. A., Dash, P. R., Read, M. L., Ward, K., Tomkins, L. M., Nazarova, O., Ulbrich, K., and Seymour, L. W. (2000) *Biochimica et Biophysica Acta.* 1475, 245-255.
(22) Anwer, K., Rhee, B. G., and Mendiratta, S. K. (2003) *Crit. Rev. Ther. Drug Carrier System* 20, 249-293.
(23) Choi, Y. H., Liu, F., Kim, J.-S., Choi, Y. K., Park, J. S., and Kim, S. W. (1998) *J. Controlled Release* 54, 39-48.
(24) Ellenbogen, E. (1952) *J. Am. Chem. Soc.* 74, 5198.
(25) Gonzalez, H., Hwang, S. J., and Davis, M. E. (1999) *Bioconjugate Chem.* 10, 1068-1074.
(26) Hwang, S. J., Bellocq, N. C., and Davis, M. E. (2001) *Bioconjugate Chem.* 12, 280-290.
(27) Reineke, T. M. and Davis, M. E. (2003) *Bioconjugate Chem.* 14, 255-261.
(28) Wolfert, M. A., Dash, P. R., Nazarova, O., Oupicky, D., Seymour, L. W., Smart, S., Strohalm, J., and Ulbrich, K. (1999) *Bioconjugate Chem.* 10, 993-1004.
(29) Bruice, T. C., and Schmir. G. L. (1958) *J. Am. Chem. Soc.* 80, 148.
(30) Plank, C., Tang, M. X., Wolfe, A. R., and Szoka, F. C., Jr. (1999) *Human Gene Therapy* 10, 319-332.
(31) Kabanov, A. V., and Kabanov, V. A. (1995) *Bioconjugate Chem.* 6, 7-20.

Thus, specific embodiments and applications of polymeric materials have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Furthermore, where a definition or use of a term in a reference, which is incorporated by reference herein is inconsistent or contrary to the definition of that term provided herein, the definition of that term provided herein applies and the definition of that term in the reference does not apply.

The invention claimed is:
1. A chimeric polymer, comprising: a carbohydrate moiety M,
wherein M is independently selected from the group consisting of a monosaccharide, an oligosaccharide, and a polysaccharide; an amino acid moiety N, wherein N comprises one amino acid or a plurality of amino acids that are covalently coupled to each via an amide bond; wherein the carbohydrate moiety M and the amino acid moiety N are covalently bonded together to form a molecule having a structure according to Formula I, Formula I' or Formula I":

$$[(M)_{x1}(N)_{y1}]_{z1}[(M)_{x2}(N)_{y2}]_{z2} \quad \text{Formula I}$$

$$[(M)_{x1}(N)_{y1}]_{z1}[(M)_{x2}]_{z2} \quad \text{Formula I'}$$

$$[(N)_{y1}]_{z1}[(M)_{x2}(N)_{y2}]_{z2} \quad \text{Formula I''}$$

wherein y2, z1, and z2 are independently an integer between 1 and 10000, inclusive, x1, x2 and y1 are independently an integer between 2 and 10000, inclusive; and wherein the carbohydrate moiety M and the amino acid moiety N are coupled to each other via amide bonds, wherein the carbonyl groups of the amide bonds are directly derived from the carbon atom of the carbohydrate moieties, and the amide bonds form a backbone of the polymer.

2. The chimeric polymer of claim 1 wherein at least one of x1 and x2 is an integer between 2 and 20.

3. The chimeric polymer of claim 1 wherein at least one of y1 and y2 is an integer between 2 and 20.

4. The chimeric polymer of claim 1 wherein a plurality of N form a peptide backbone, and wherein the peptide backbone is formed via a covalent bond between one of an alpha, beta, gamma, or epsilon amino group of an amino acid and one of an alpha, beta, and gamma carboxylate group of a second amino acid.

5. The chimeric polymer of claim 1 wherein at least one of the carbohydrate moieties is a cyclic carbohydrate.

6. The chimeric polymer of claim 1 wherein at least one of the carbohydrate moieties is an acyclic carbohydrate.

7. The chimeric polymer of claim 1 wherein at least one of the amino acids is a non-naturally occurring amino acid.

8. The chimeric polymer of claim 1 wherein at least one of M and N further comprises a crosslinking functionality, and wherein the crosslinking functionality is covalently bound to another crosslinking functionality of another chimeric polymer to thereby form a crosslinked polymer.

9. The chimeric polymer of claim 1 wherein at least one of M and N further comprises a crosslinking functionality, and wherein the crosslinking functionality is bound to another crosslinking functionality of another chimeric polymer through at least one of an ionic bond, a hydrogen bond, a disulfide bond, and a hydrophobic interaction to thereby form a crosslinked polymer.

10. The chimeric polymer of any one of claim 8 or claim 9 wherein the crosslinked polymer further comprises an aqueous medium to thereby form a hydrogel and wherein the hydrogen optionally includes at least one of a pharmaceutical agent and a cell.

11. The chimeric polymer of claim 1 wherein the polymer is formulated in a formulation suitable for at least one of implantation, injection, topical, mucosal, and oral administration.

12. A pharmaceutical composition comprising the chimeric polymer of claim 1 and a pharmaceutically active agent, wherein the pharmaceutically active agent is optionally covalently attached to the polymer.

13. The pharmaceutical composition of claim 12 wherein the pharmaceutically active agent is encapsulated in a matrix formed by the polymer.

14. The pharmaceutical composition of claim 12 wherein the pharmaceutically active agent is a peptide, and wherein at least one of $(N)_{y1}$ and $(N)_{y2}$ comprises the pharmaceutically active agent.

15. The pharmaceutical composition of claim 12 wherein the polymer has a composition that is suitable for biodegradation to thereby release the pharmacologically active agent.

* * * * *